United States Patent
Asano et al.

(10) Patent No.: US 11,344,475 B2
(45) Date of Patent: May 31, 2022

(54) CONNECTION EQUIPMENT AND EQUIPMENT CONNECTOR

(71) Applicant: DAIWA CAN COMPANY, Tokyo (JP)

(72) Inventors: Toshihiro Asano, Sagamihara (JP); Toshio Iino, Sagamihara (JP); Mio Hattori, Sagamihara (JP); Naoyuki Takahashi, Sagamihara (JP); Kousuke Kuwahara, Sagamihara (JP); Naoki Sunaga, Sagamihara (JP); Masanori Okabayashi, Sagamihara (JP)

(73) Assignee: Daiwa Can Company

( * ) Notice: Subject to any disclaimer, the term of this patent is extended or adjusted under 35 U.S.C. 154(b) by 293 days.

(21) Appl. No.: 16/590,486

(22) Filed: Oct. 2, 2019

(65) Prior Publication Data

US 2020/0038289 A1    Feb. 6, 2020

Related U.S. Application Data

(63) Continuation of application No. PCT/JP2018/014151, filed on Apr. 2, 2018.

(30) Foreign Application Priority Data

Apr. 3, 2017 (JP) .............................. JP2017-073898
Jul. 31, 2017 (JP) .............................. JP2017-148173

(51) Int. Cl.
    *A61M 5/178*        (2006.01)
    *A61J 1/20*          (2006.01)

(52) U.S. Cl.
CPC .............. *A61J 1/2072* (2015.05); *A61J 1/201* (2015.05); *A61J 1/2037* (2015.05); *A61J 1/2096* (2013.01); *A61M 5/1782* (2013.01); *A61J 1/2055* (2015.05)

(58) Field of Classification Search
CPC ........ A61J 1/2072; A61J 1/201; A61J 1/2037; A61J 1/2096; A61J 1/2055; A61J 1/2017; A61M 5/1782
See application file for complete search history.

(56) References Cited

U.S. PATENT DOCUMENTS 8,196,614 B2 * 6/2012 Kriheli ................. A61M 5/162
                                                                                                      141/5
9,731,083 B2     8/2017 Asano et al.
(Continued)

FOREIGN PATENT DOCUMENTS

CN       101466344 A     6/2009
CN       102307556 A     1/2012
(Continued)

OTHER PUBLICATIONS

International Search Report for Application No. PCT/JP2018/014151 dated Jun. 5, 2018 (with English translation) (10 pages).
(Continued)

*Primary Examiner* — Jason K Niesz
(74) *Attorney, Agent, or Firm* — Harness, Dickey & Pierce, P.L.C.

(57) ABSTRACT

Connection equipment includes an equipment connector comprising a first connecting section, a first liquid flow path that communicates with a equipment, and a first valve that is to open and close the first liquid flow path, a container connector comprising a second connecting section, a second liquid flow path that communicates with the container, and a second valve that is to open and close the second liquid flow path, and a lock mechanism that locks the equipment connector and the container connector in a state where the first liquid flow path is in communication with the second liquid flow path, and that unlocks the connectors in a state where the first valve and the second valve are closed.

14 Claims, 38 Drawing Sheets

(56) References Cited

U.S. PATENT DOCUMENTS

| | | | |
|---|---|---|---|
| 9,999,569 B2* | 6/2018 | Kriheli | A61J 1/201 |
| 2010/0218846 A1 | 9/2010 | Kriheli | |
| 2014/0261876 A1 | 9/2014 | Mansour et al. | |
| 2014/0261877 A1 | 9/2014 | Ivosevic et al. | |
| 2014/0276649 A1 | 9/2014 | Ivosevic et al. | |
| 2016/0058667 A1 | 3/2016 | Kriheli | |
| 2016/0158104 A1 | 6/2016 | Ali et al. | |
| 2016/0369922 A1 | 12/2016 | Blake et al. | |
| 2019/0248090 A1 | 8/2019 | Fujishige et al. | |

FOREIGN PATENT DOCUMENTS

| | | |
|---|---|---|
| CN | 104474611 A | 4/2015 |
| CN | 105008227 A | 10/2015 |
| CN | 105050565 A | 11/2015 |
| CN | 105392463 A | 3/2016 |
| CN | 105722493 A | 6/2016 |
| EP | 2358327 B1 | 11/2013 |
| JP | 690993 | 4/1994 |
| JP | 2006212084 A | 8/2006 |
| JP | 2012511940 A | 5/2012 |
| JP | 2013006748 A1 | 1/2013 |
| JP | 2016521176 A | 7/2016 |
| JP | 201735618 A | 2/2017 |
| WO | WO-2010/069359 A1 | 6/2010 |
| WO | 2014181320 A1 | 11/2014 |
| WO | 2015009746 A2 | 1/2015 |

OTHER PUBLICATIONS

International Preliminary Report on Patentability for PCT/JP2018/014151, dated Oct. 8, 2019 (13 pages).

Singapore Written Opinion for Application No. 11201908927T (In English) dated Dec. 10, 2020 (7 pages).

Extended European Search Report for Application No. 18781021.3 dated Apr. 16, 2021 (9 pages).

Taiwanese Office Action for corresponding Application No. 107111784 dated Jul. 28, 2021 with English translation (11 Pages).

Chinese Office Action dated Aug. 10, 2021 (with English translation) for Application No. 201880023386.4 (26 pages).

Japanese Office Action dated Apr. 12, 2022 for Japanese Application No. 2019-511237 (with English translation) 10 pages.

* cited by examiner

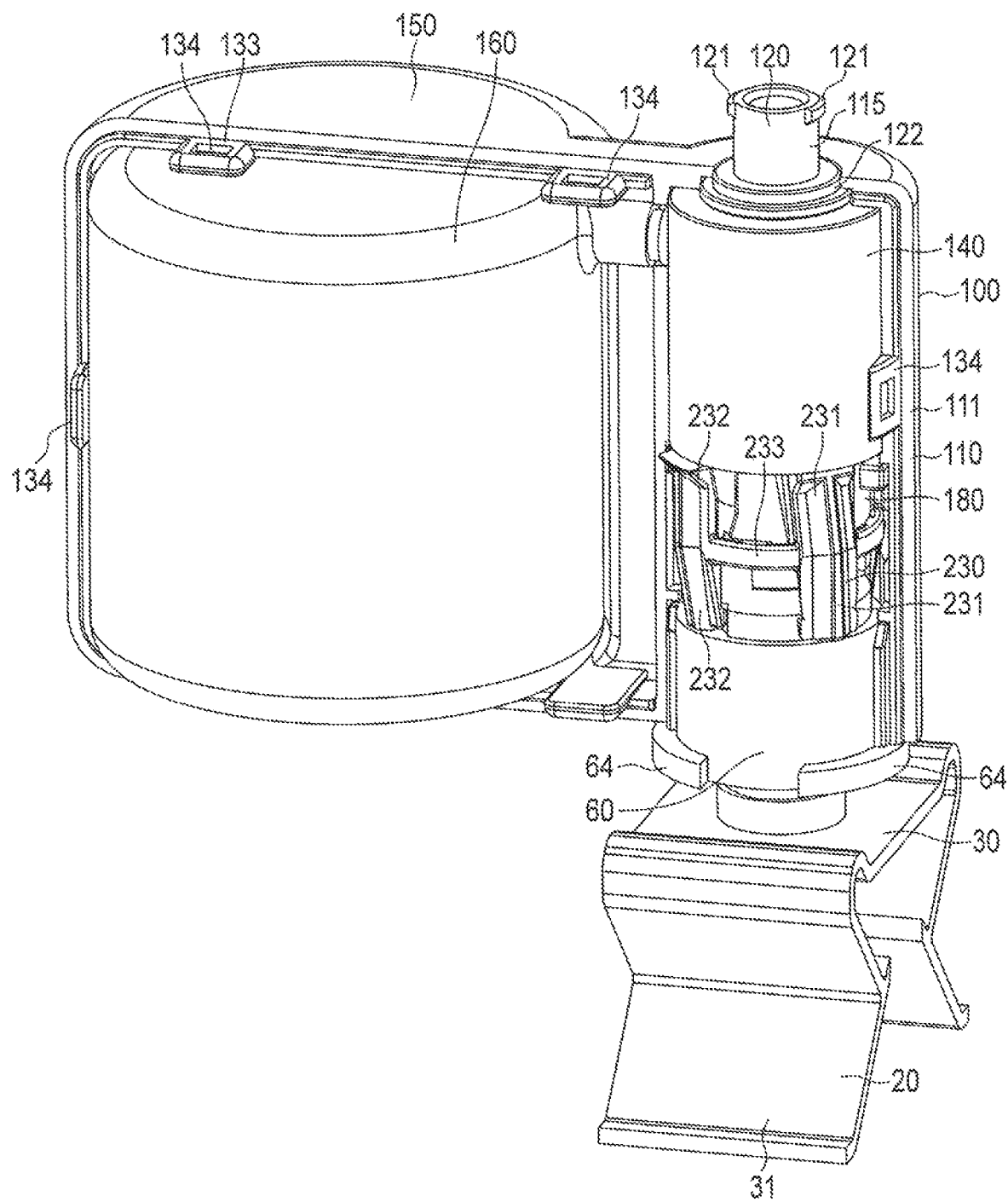
F I G. 6

CONNECTION EQUIPMENT AND EQUIPMENT CONNECTOR

CROSS-REFERENCE TO RELATED APPLICATIONS

This is a Continuation Application of PCT Application NO. PCT/JP2018/014151, filed on Apr. 2, 2018 and based upon and claiming the benefit of priority from prior Japanese Patent Application No. 2017-073898, filed Apr. 3, 2017; and Japanese Patent Application No. 2017-148173, filed Jul. 31, 2017, the entire contents all of which are incorporated herein by reference.

BACKGROUND OF THE INVENTION

1. Field of the Invention

Embodiments described herein relate generally to closed type connection equipment that connects equipment to a container and forms a flow path between the container and the equipment, and an equipment connector for use in the closed type connection equipment.

2. Description of the Related Art

There is known connection equipment that connects a syringe to a container and forms, between the container and the syringe, a flow path through which a chemical solution flows, when the chemical solution is collected to the syringe from a container such as a vial in which the chemical solution, such as an anti-cancer agent, is contained. Such connection equipment has a syringe connector fixed to the syringe, and a container connector fixed to the vial.

The syringe connector has a part of the flow path in an interior thereof. The container connector has the other part of the flow path in an interior thereof. When the syringe connector is connected to the container connector, the part of the flow path is continuous with the other part thereof, and the flow path from the container to the syringe is formed. Such a technique is disclosed, for example, in Jpn. Pat. Appln. KOKAI Publication No. H06-90993.

An operator such as a pharmacist connects the syringe connector to the container connector to form the flow path, and then pulls a plunger of the syringe, thereby collecting the chemical solution in the container to the syringe.

In this connection equipment, when the collection of the chemical solution to the syringe is completed and then the syringe connector is disconnected from the container connector before each of the part of the flow path in the syringe connector and the other part of the flow path in the container connector is sealed, the chemical solution might leak outwardly from the flow path.

To solve this problem, as the connection equipment, there is known connection equipment having a lock mechanism that regulates disconnection of a syringe connector from a container connector before a part of a flow path in the syringe connector and the other part of the flow path in the container connector are sealed. As the lock mechanism, there is known a lock mechanism that locks the syringe connector and the container connector by operating, e.g., relatively rotating the syringe connector and the container connector after the syringe connector is connected to the container connector.

Connection equipment having the above described lock mechanism has the following problem. Specifically, an operator needs to perform an operation of connecting a syringe connector to a container connector and an operation of locking the syringe connector and the container connector, before collecting a chemical solution from a container to a syringe. When these operations require different movements of the operator, the operations become complicated.

BRIEF SUMMARY OF THE INVENTION

According to an aspect of embodiments, a connection equipment includes an equipment connector, a container connector, and a lock mechanism. The equipment connector includes a first connecting section that is connectable to equipment through which a fluid moves, a first liquid flow path that communicates with an interior of the equipment when the equipment is connected to the first connecting section, and a first valve that is to open and close the first liquid flow path and that opens when pressed.

The container connector includes a second connecting section that is connectable to a container, a second liquid flow path that communicates with an interior of the container when the container is connected to the second connecting section, and a second valve that is to open and close the second liquid flow path and that opens when pressed by the first valve. The lock mechanism locks the equipment connector and the container connector in a state where the first valve is pressed by the second valve, the first valve and the second valve are opened and the first liquid flow path is in communication with the second liquid flow path, and that unlocks the connectors in a state where the first valve and the second valve are closed.

According to an aspect of embodiments, an equipment connector includes a first connecting section that is connectable to equipment through which a fluid moves, a first liquid flow path that communicates with an interior of the equipment when the equipment is connected to the first connecting section, a first valve that is to open and close the first liquid flow path and that opens when pressed, and a lock mechanism that locks a container connector in a state where the first valve is pressed by a second valve of the container connector, the first valve and the second valve are opened and the first liquid flow path is in communication with a second liquid flow path of the container connector, and that unlocks the container connector in a state where the first valve and the second valve are closed.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 6 is a perspective view showing the state where the container connector and the syringe connector are connected and the liquid flow path and the gas flow path are formed, while one of outer shell constituting members of the syringe connector is removed.

DETAILED DESCRIPTION OF THE INVENTION

Connection equipment 10 according to an embodiment of the present invention will be described with reference to FIG. 1 to FIG. 20. The connection equipment 10 is for use in collecting a chemical solution from a container 5 such as a vial to a syringe 6, connects the container 5 to the syringe 6, and forms a liquid flow path L1 through which the chemical solution flows between an interior of the container 5 and an interior of the syringe 6, and a gas flow path L2 via which the interior of the container 5 communicates with an interior of an after-mentioned air bag 160. The container 5 has a mouth. The mouth is sealed with a plug. The plug is made of a material such as a rubber.

Figure 1:
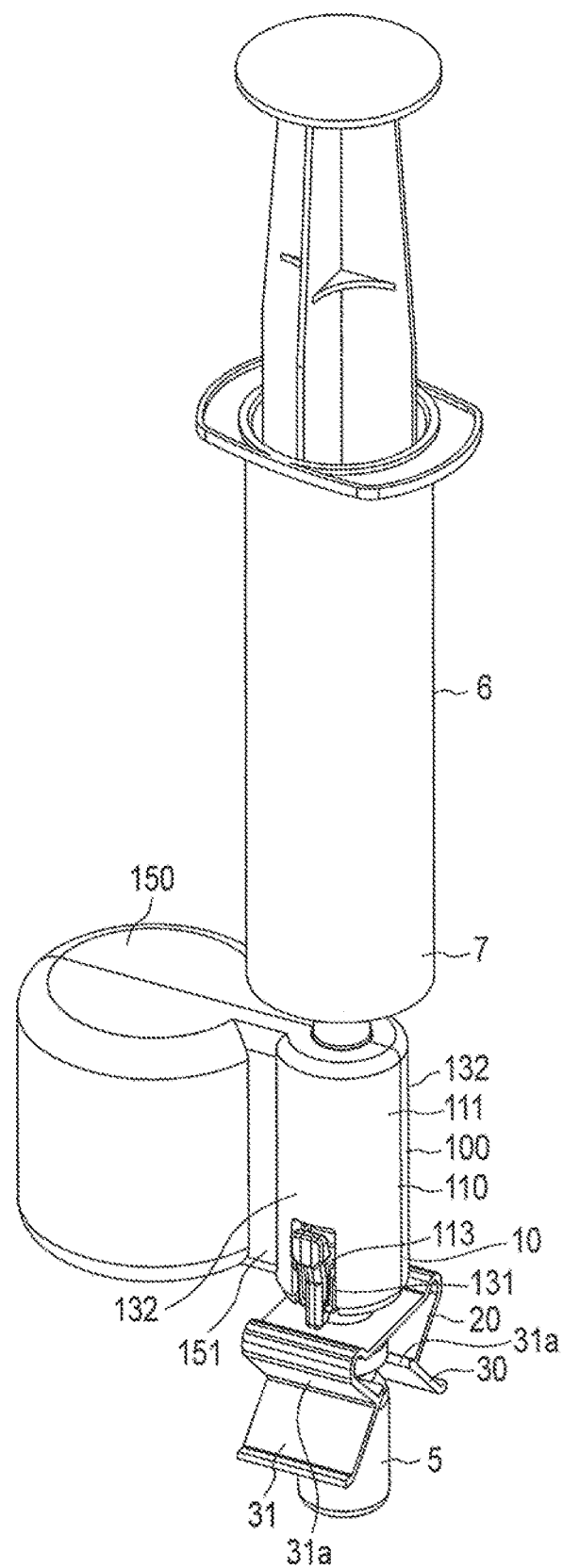
FIG. 1 is a perspective view showing a state where a container and a syringe are connected by connection equipment according to an embodiment of the present invention.
Figure 2:
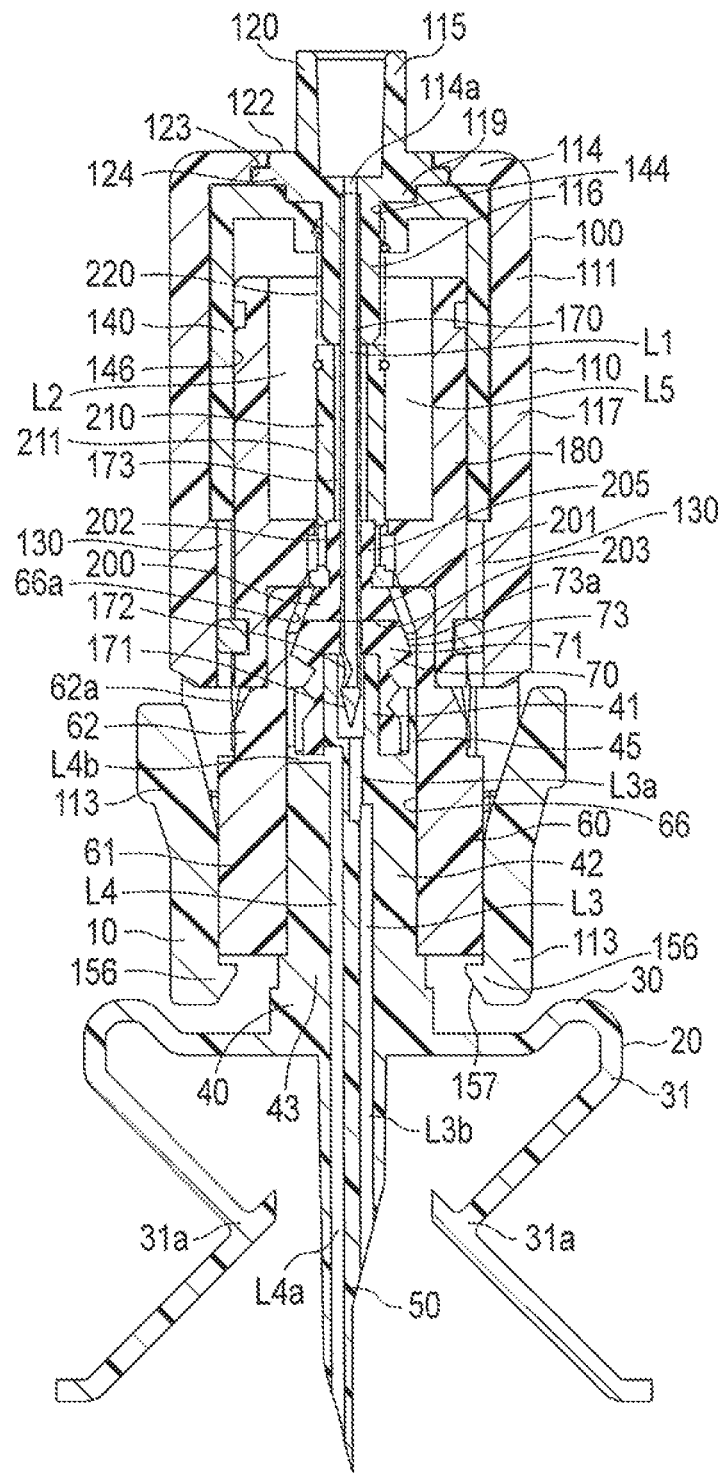
FIG. 2 is a cross-sectional view showing a state where a container connector of the connection equipment and a syringe connector are connected and a liquid flow path and a gas flow path are formed.
Figure 3:
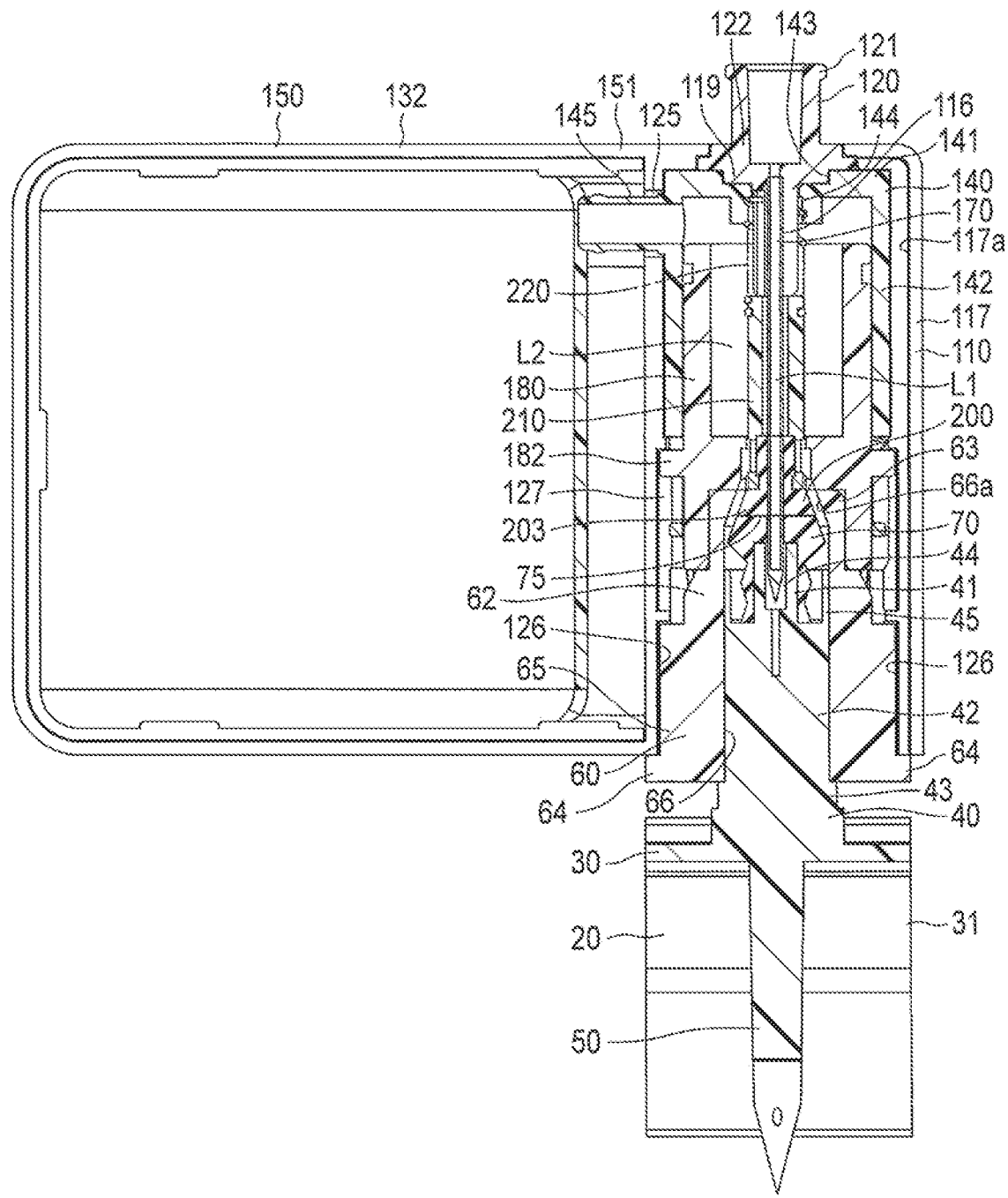
FIG. 3 is a cross-sectional view showing the state where the container connector and the syringe connector are connected and the liquid flow path and the gas flow path are formed.

FIG. 1 is a perspective view showing a state where the container 5 and the syringe 6 are connected by the connection equipment 10. FIG. 2 is a cross-sectional view showing a state where a container connector 20 of the connection equipment 10 and a syringe connector 100 are connected and the liquid flow path L1 and the gas flow path L2 are formed. FIG. 3 is a cross-sectional view showing the state where the container connector 20 and the syringe connector 100 are connected and the liquid flow path L1 and the gas flow path L2 are formed. FIG. 3 is a cross-sectional view showing the connection equipment 10 along a cut plane rotated by 90 degrees from a cross section shown in FIG. 2 about an axis of an outer shell main body 111.

Figure 4:
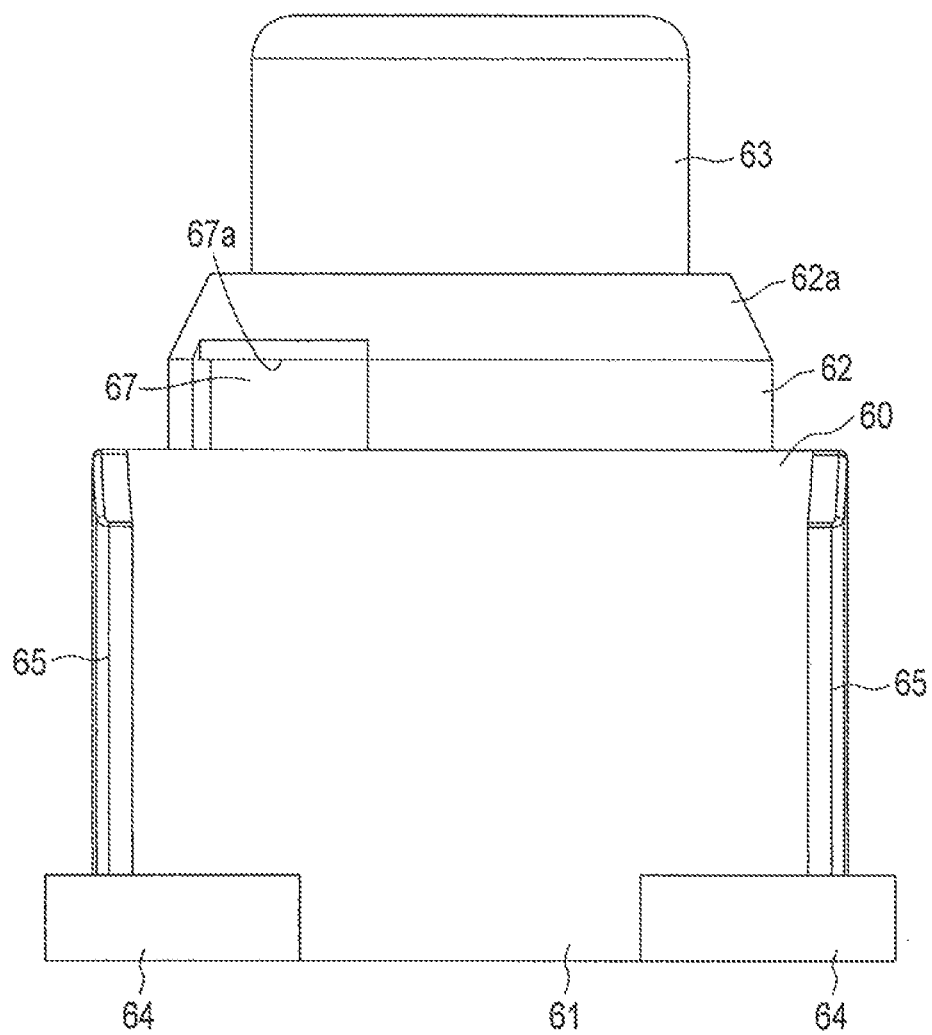
FIG. 4 is a side view showing a seal cap of the container connector.
Figure 5:
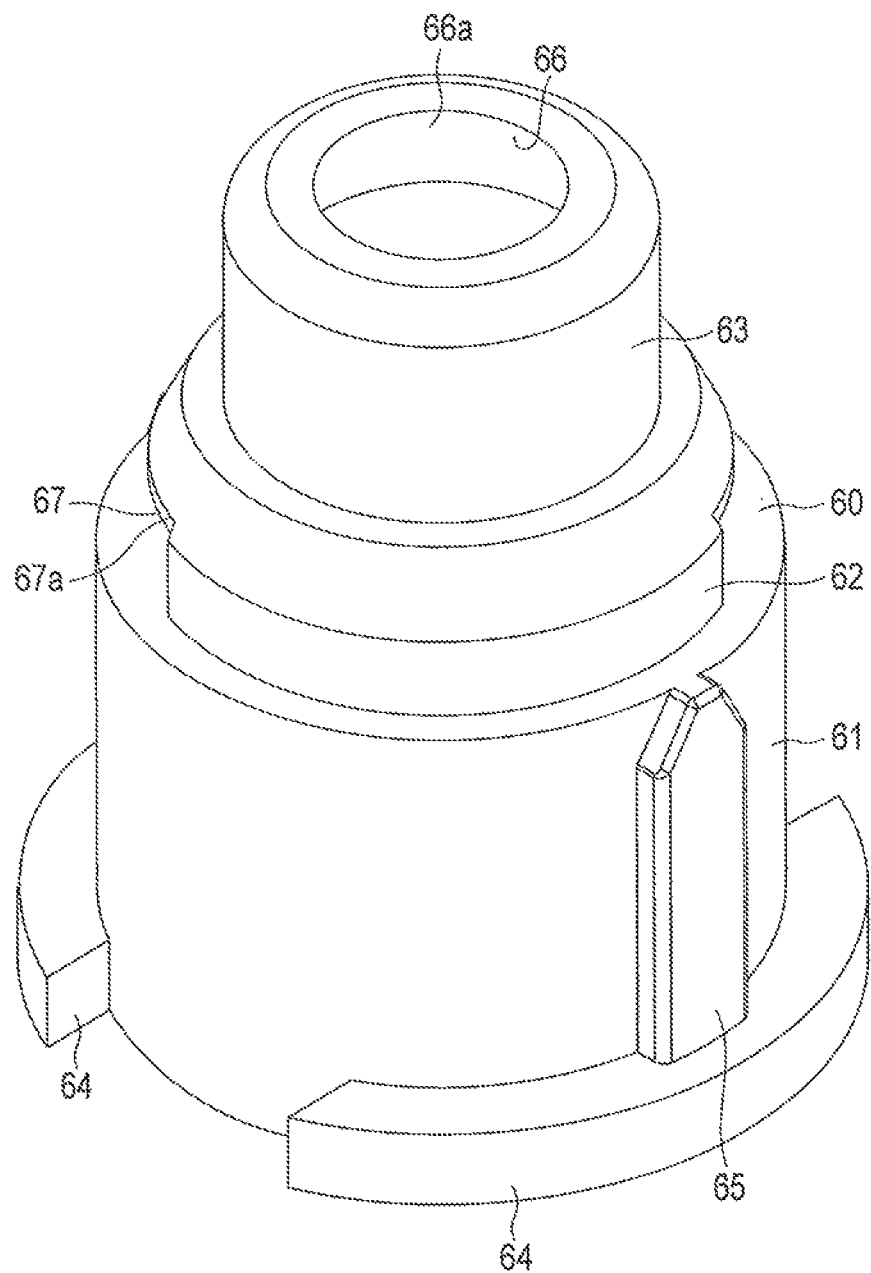
FIG. 5 is a perspective view showing the seal cap.

FIG. 4 is a side view showing a seal cap 60 of the container connector 20. FIG. 5 is a perspective view showing the seal cap 60. FIG. 6 is a perspective view showing the state where the container connector 20 and the syringe connector 100 are connected and the liquid flow path L1 and the gas flow path L2 are formed, while one of outer shell constituting members 132 of the syringe connector 100 is removed.

Figure 7:
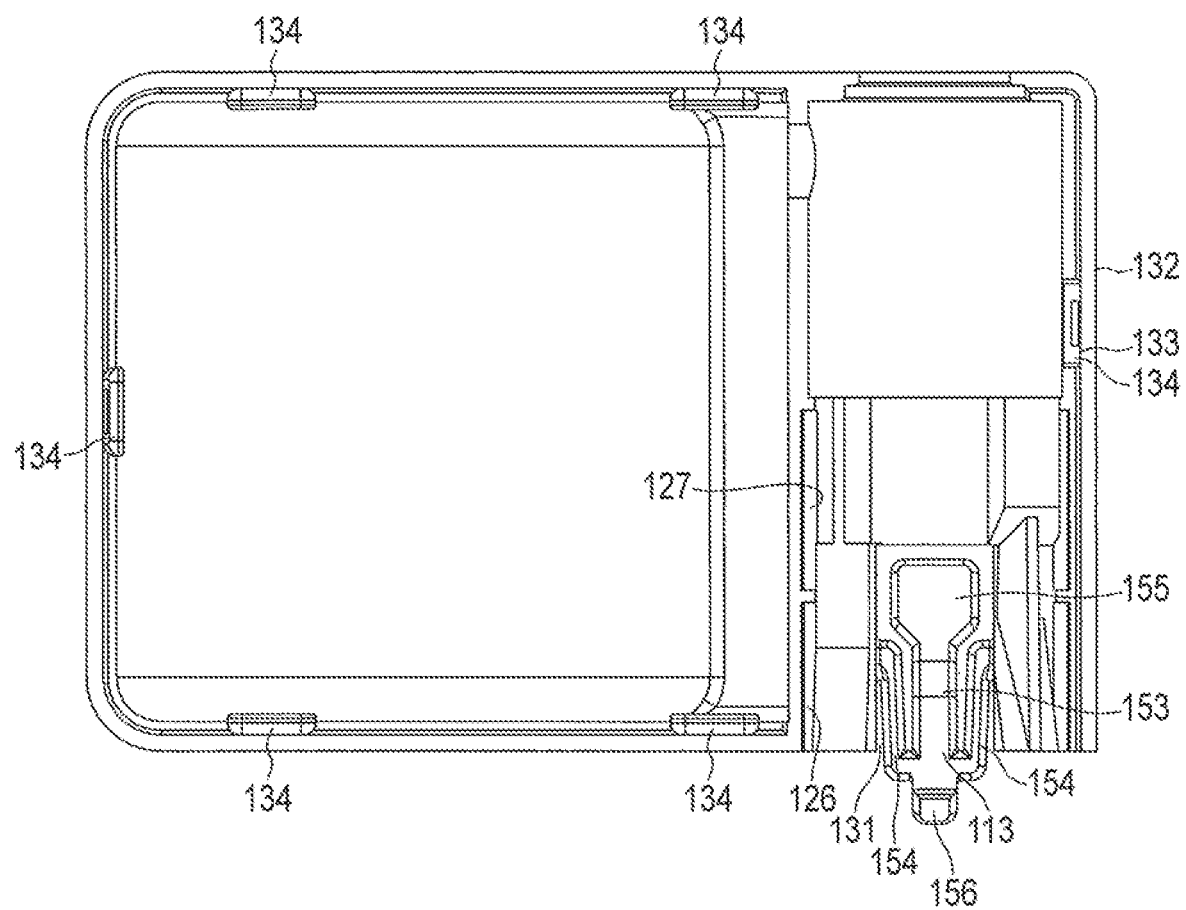
FIG. 7 is a front view showing the outer shell constituting member.
Figure 8:
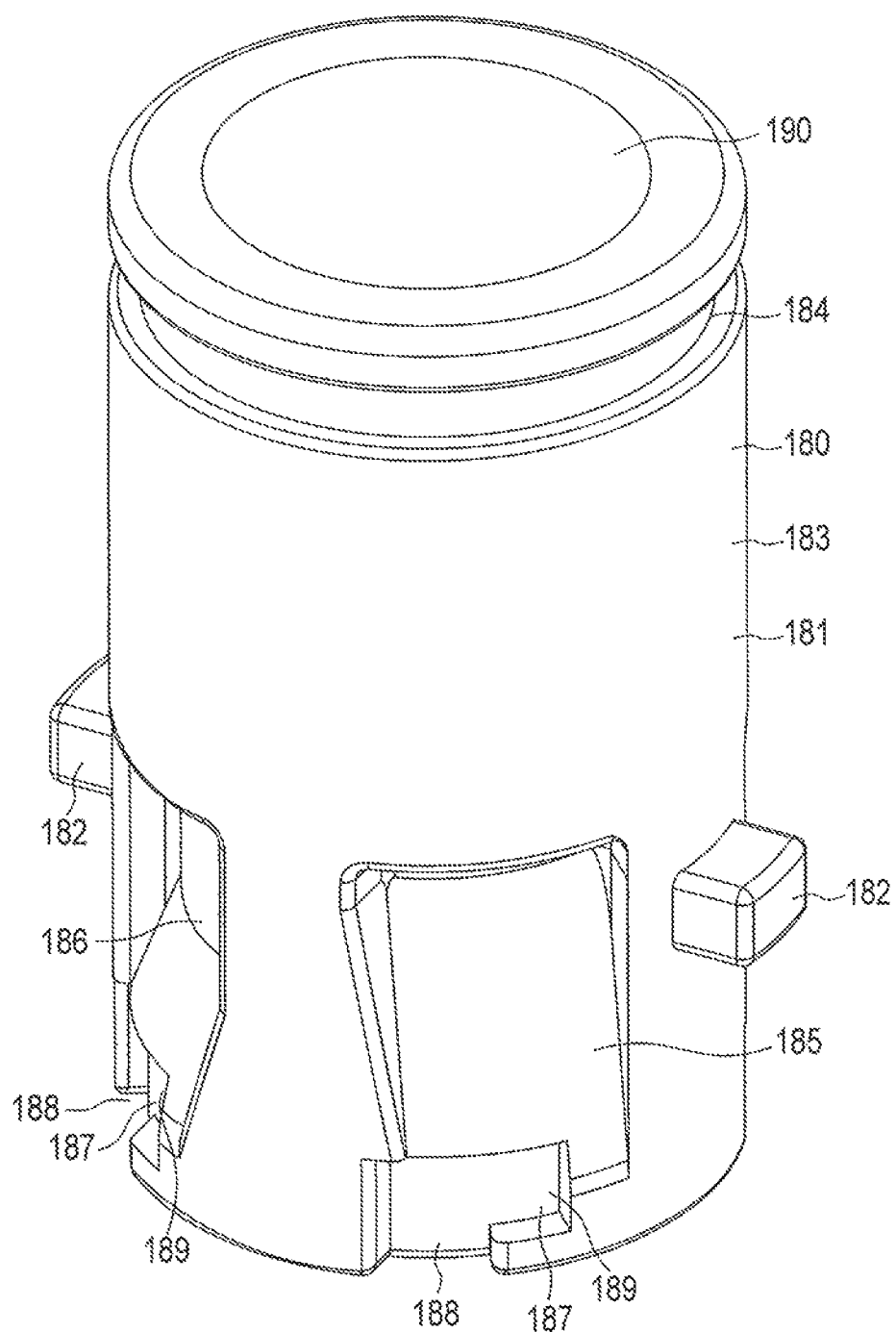
FIG. 8 is a perspective view showing a head sleeve of the syringe connector.
Figure 9:
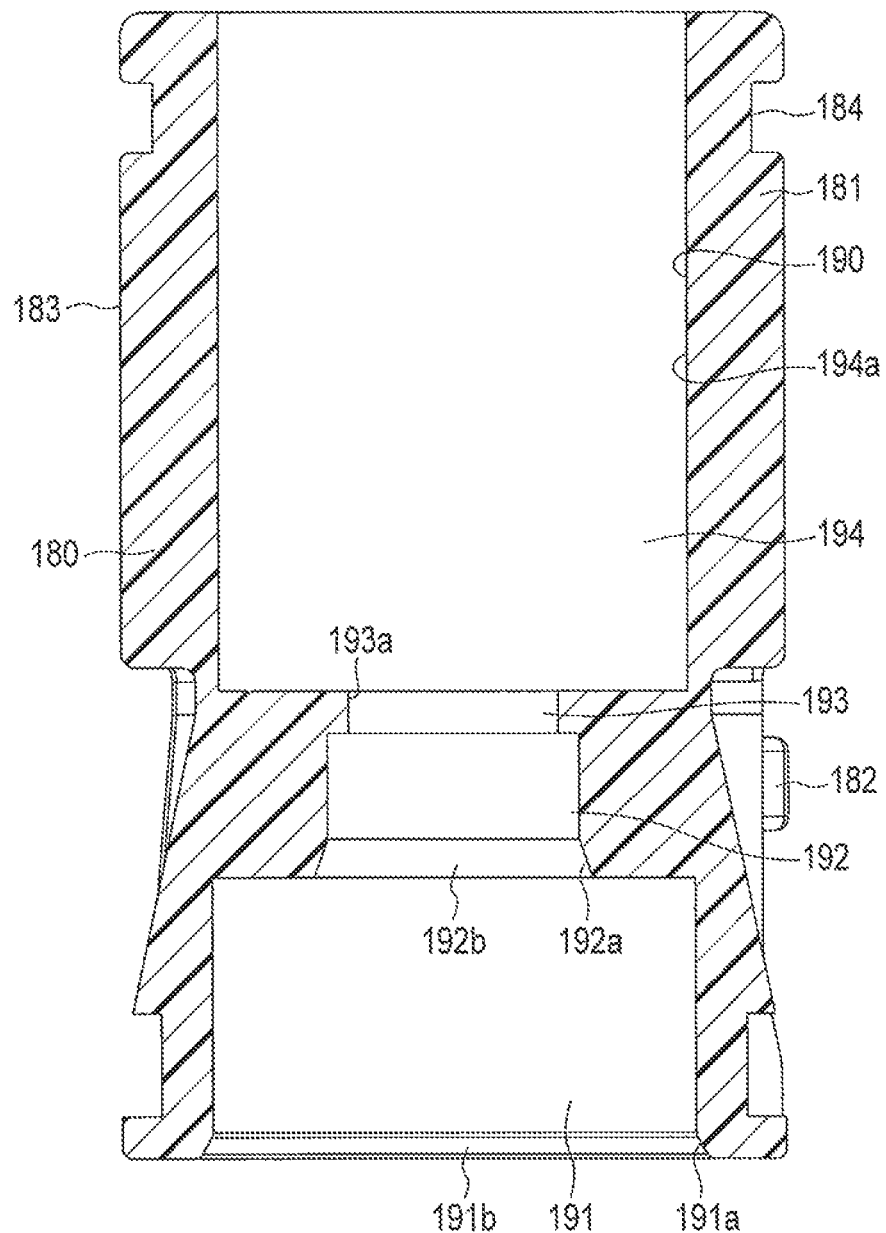
FIG. 9 is a cross-sectional view showing the head sleeve.
Figure 10:
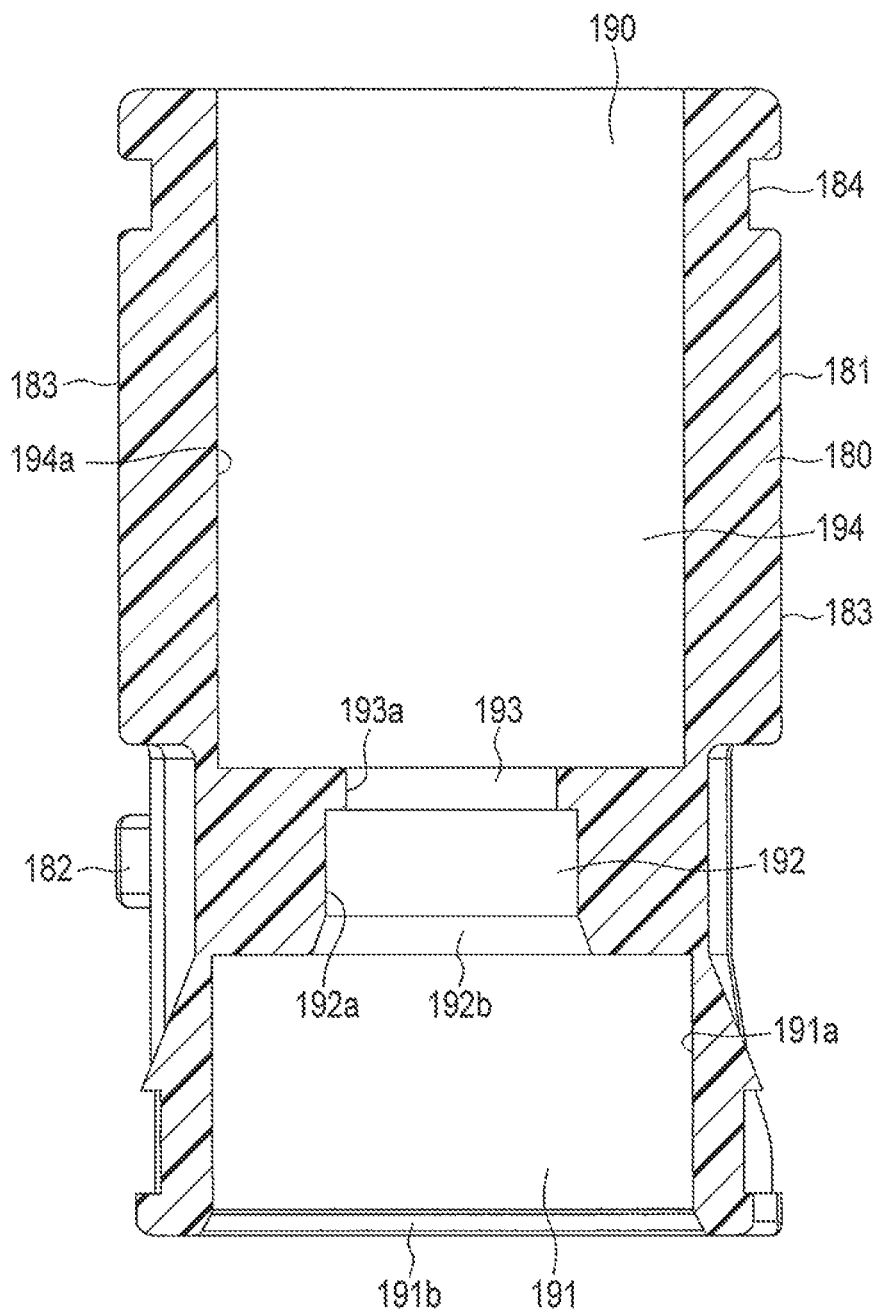
FIG. 10 is a cross-sectional view showing the head sleeve.

FIG. 7 is a front view showing the outer shell constituting member 132 of an outer shell 110. FIG. 8 is a perspective view showing a head sleeve 180 of the syringe connector 100. FIG. 9 is a cross-sectional view showing the head sleeve 180. FIG. 10 is a cross-sectional view showing the head sleeve 180. FIG. 10 is a cross-sectional view showing the head sleeve 180 along a cut plane rotated by 90 degrees from a cross section shown in FIG. 9 about an axis of the head sleeve 180.

Figure 11:
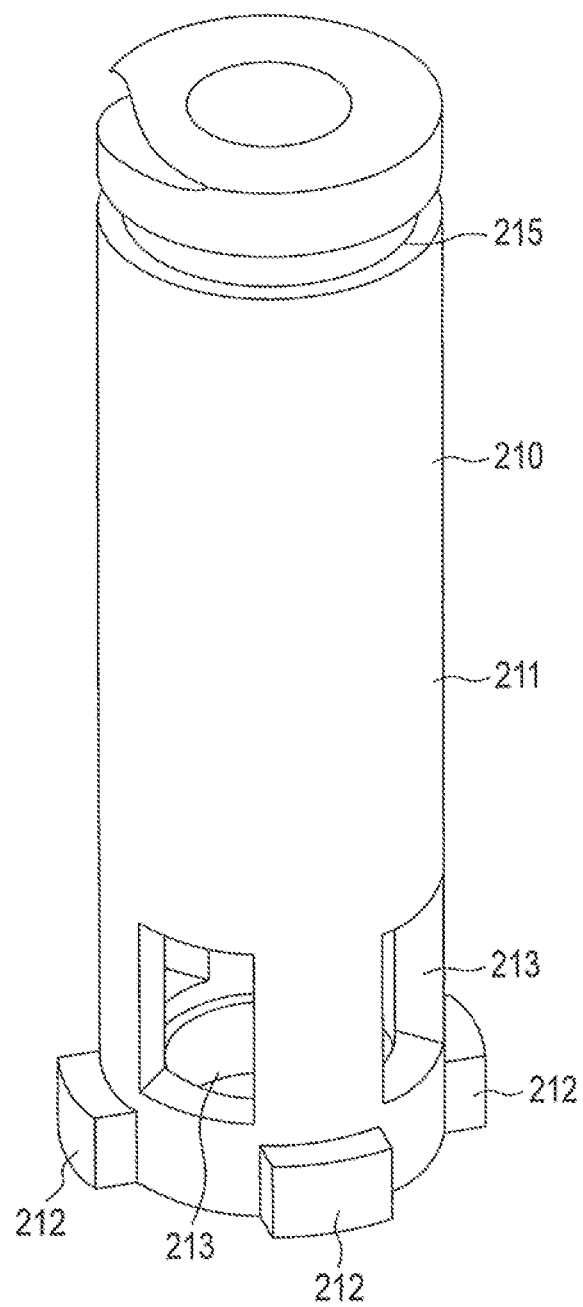
FIG. 11 is a perspective view showing a needle seal holder of the syringe connector.
Figure 12:
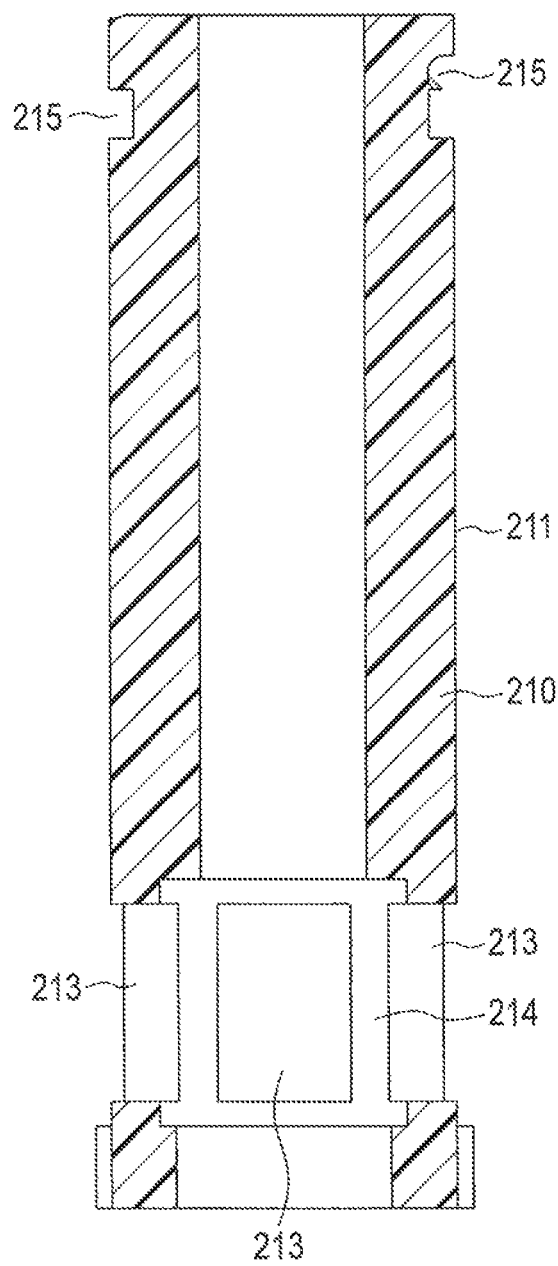
FIG. 12 is a cross-sectional view showing the needle seal holder.
Figure 13:
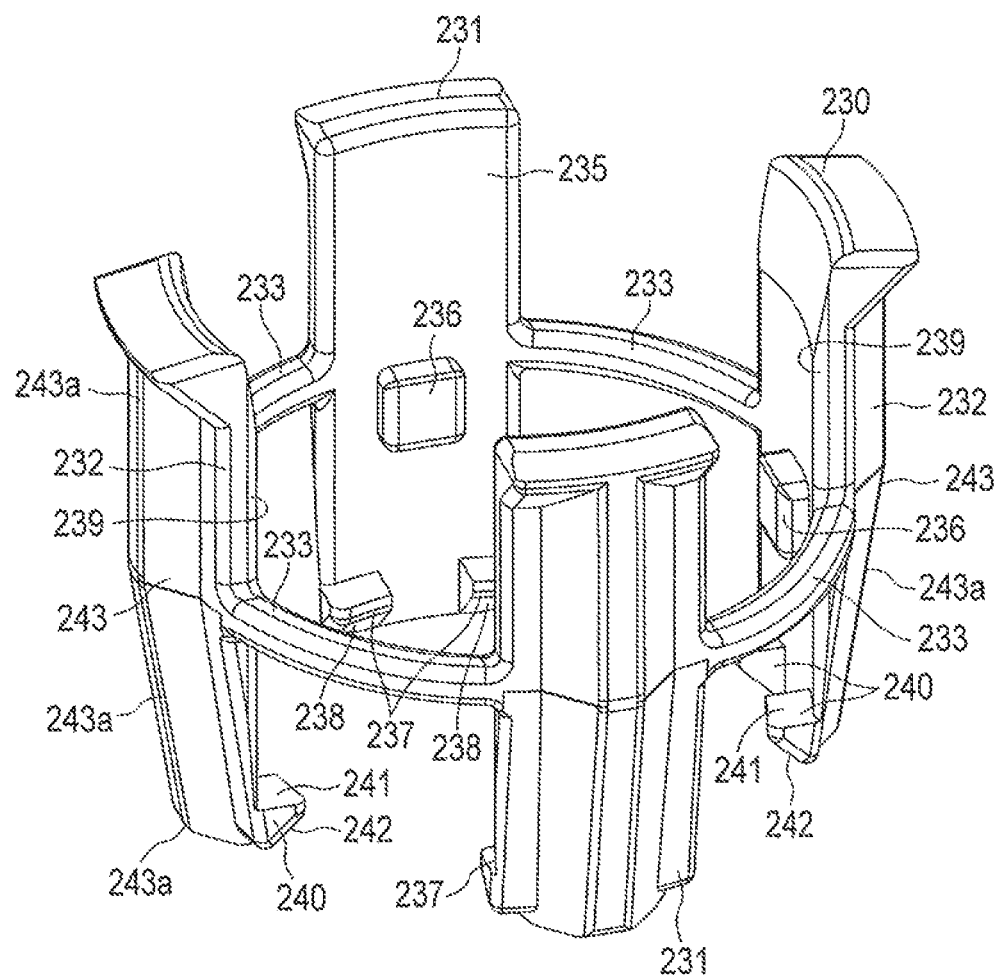
FIG. 13 is a perspective view showing a stopper sleeve of the syringe connector.
Figure 14:
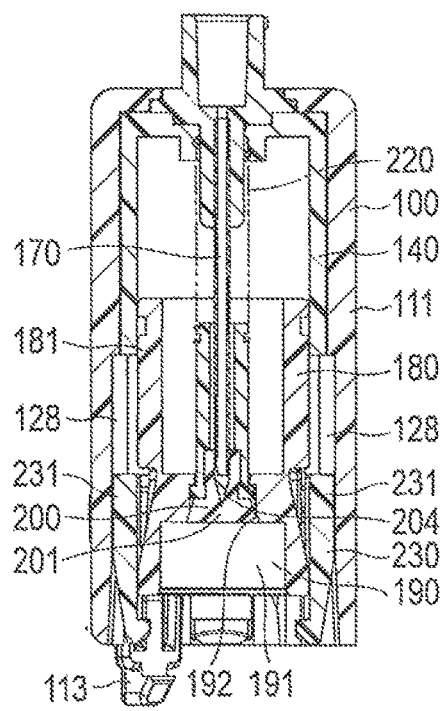
FIG. 14 is a cross-sectional view showing the container connector and the syringe connector before connected.
Figure 14:
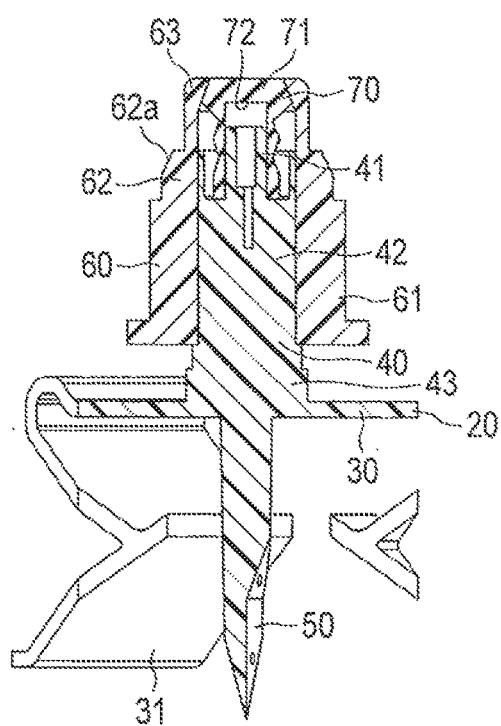
Figure 15:
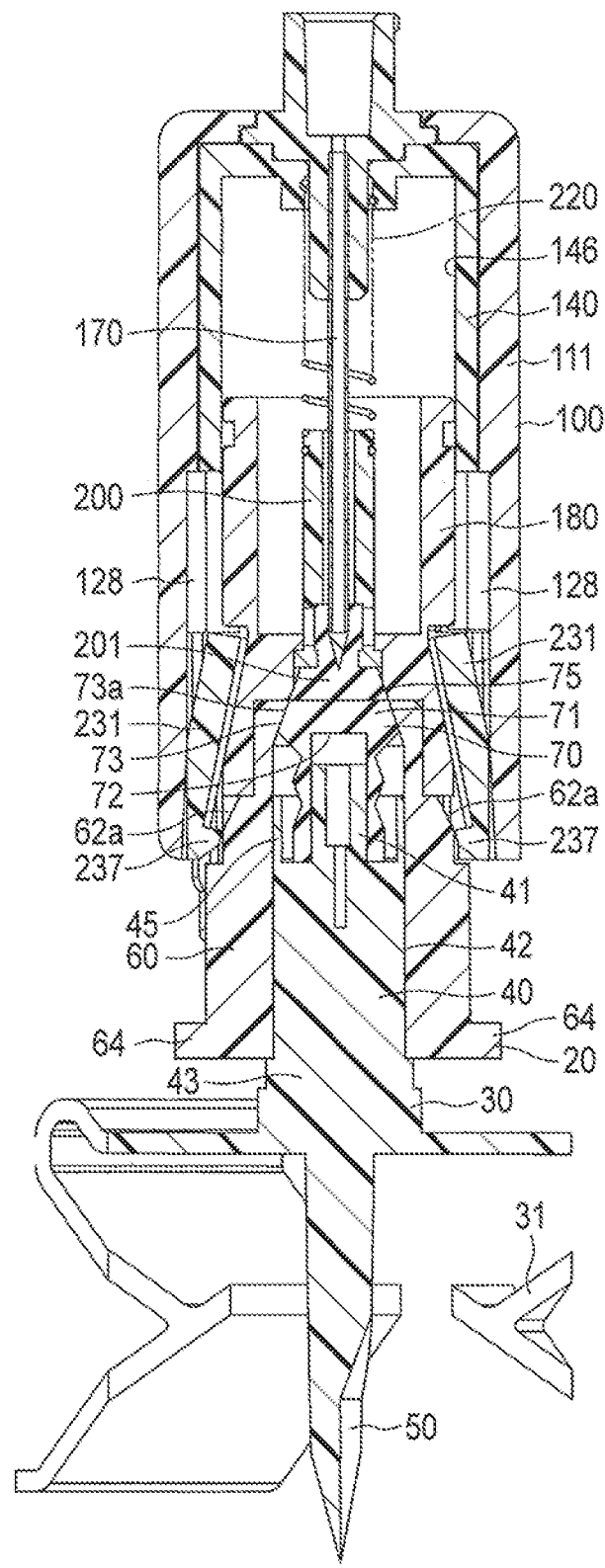
FIG. 15 is a cross-sectional view showing the container connector and the syringe connector that are connected in a state where the liquid flow path and the gas flow path are not formed.

FIG. 11 is a perspective view showing a needle seal holder 210 of the syringe connector 100. FIG. 12 is a cross-sectional view showing the needle seal holder 210. FIG. 13 is a perspective view showing a stopper sleeve 230 of the syringe connector 100. FIG. 14 is a cross-sectional view showing the container connector 20 and the syringe connector 100 before connected. FIG. 15 is a cross-sectional view showing the container connector 20 and the syringe connector 100 that are connected in a state where the liquid flow path L1 and the gas flow path L2 are not formed.

Figure 16:
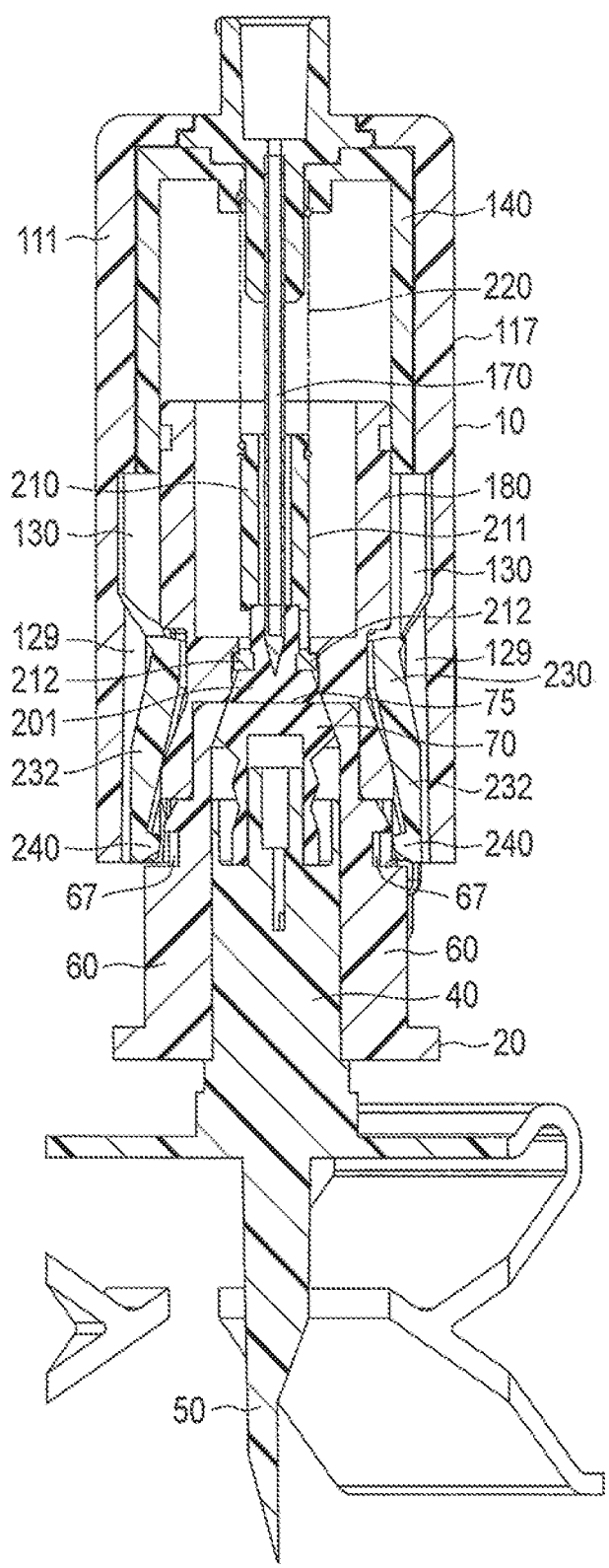
FIG. 16 is a cross-sectional view showing the container connector and the syringe connector that are connected in the state where the liquid flow path and the gas flow path are not formed.

FIG. 16 is a cross-sectional view showing the container connector 20 and the syringe connector 100 that are connected in the state where the liquid flow path L1 and the gas flow path L2 are not formed. FIG. 16 is a cross-sectional view showing the state where the container connector 20 and the syringe connector 100 are cut along a cut plane rotated by 90 degrees from a cross section shown in FIG. 15 about the axis of the outer shell main body 111.

Figure 17:
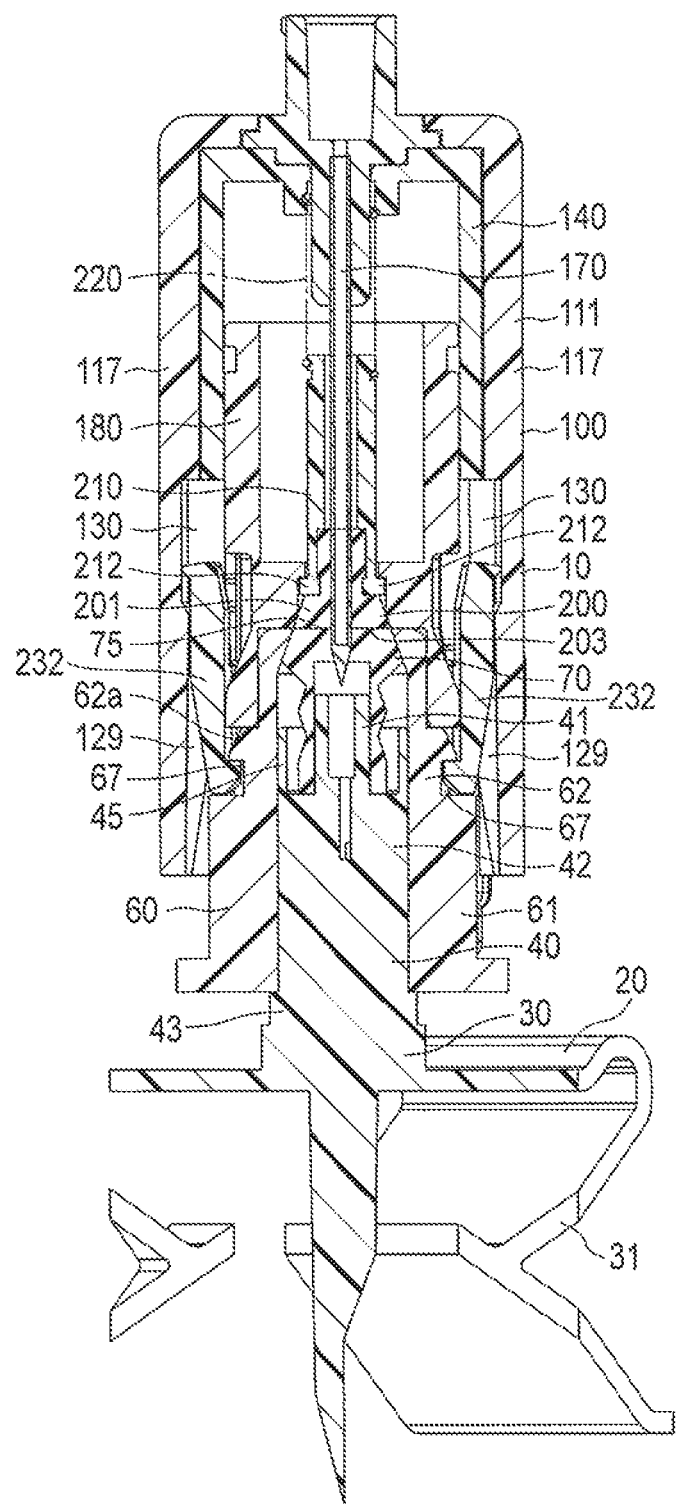
FIG. 17 is a cross-sectional view showing the container connector and the syringe connector that are connected in the state where the liquid flow path and the gas flow path are not formed.
Figure 18:
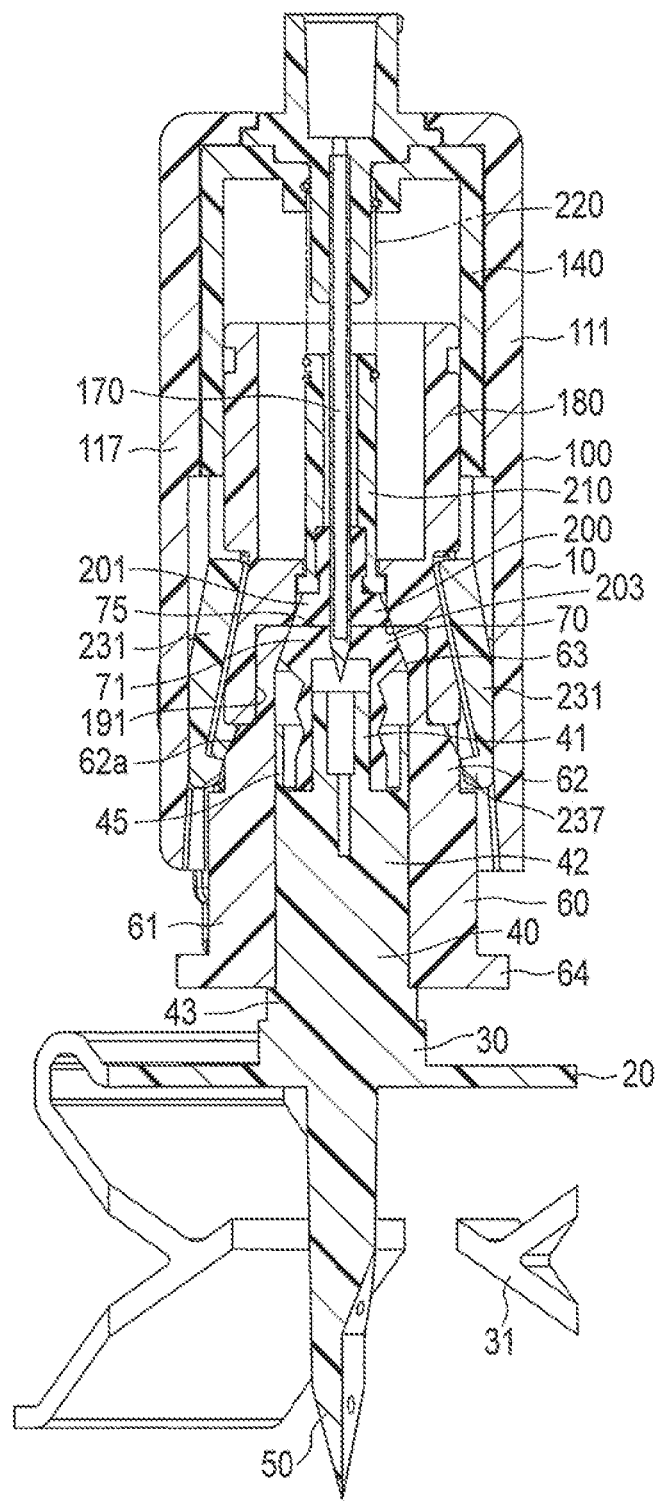
FIG. 18 is a cross-sectional view showing the container connector and the syringe connector that are connected in the state where the liquid flow path and the gas flow path are not formed.

FIG. 17 is a cross-sectional view showing the container connector 20 and the syringe connector 100 that are connected in the state where the liquid flow path L1 and the gas flow path L2 are not formed. FIG. 18 is a cross-sectional view showing the container connector 20 and the syringe connector 100 that are connected in the state where the liquid flow path L1 and the gas flow path L2 are not formed. FIG. 18 is a cross-sectional view showing the state where the container connector 20 and the syringe connector 100 are cut along a cut plane rotated by 90 degrees from a cross section shown in FIG. 17 about the axis of the outer shell main body 111.

Figure 19:
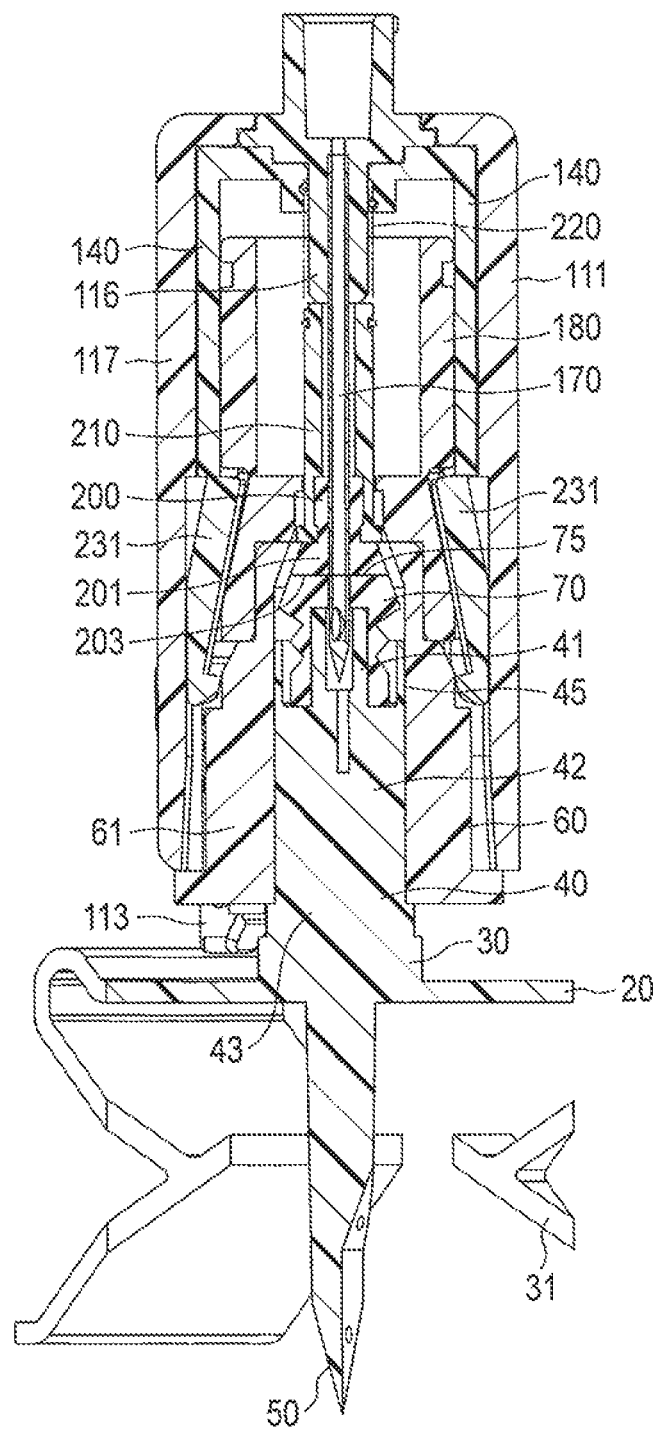
FIG. 19 is a cross-sectional view showing the container connector and the syringe connector that are connected in a state where the liquid flow path and the gas flow path are formed.
Figure 20:
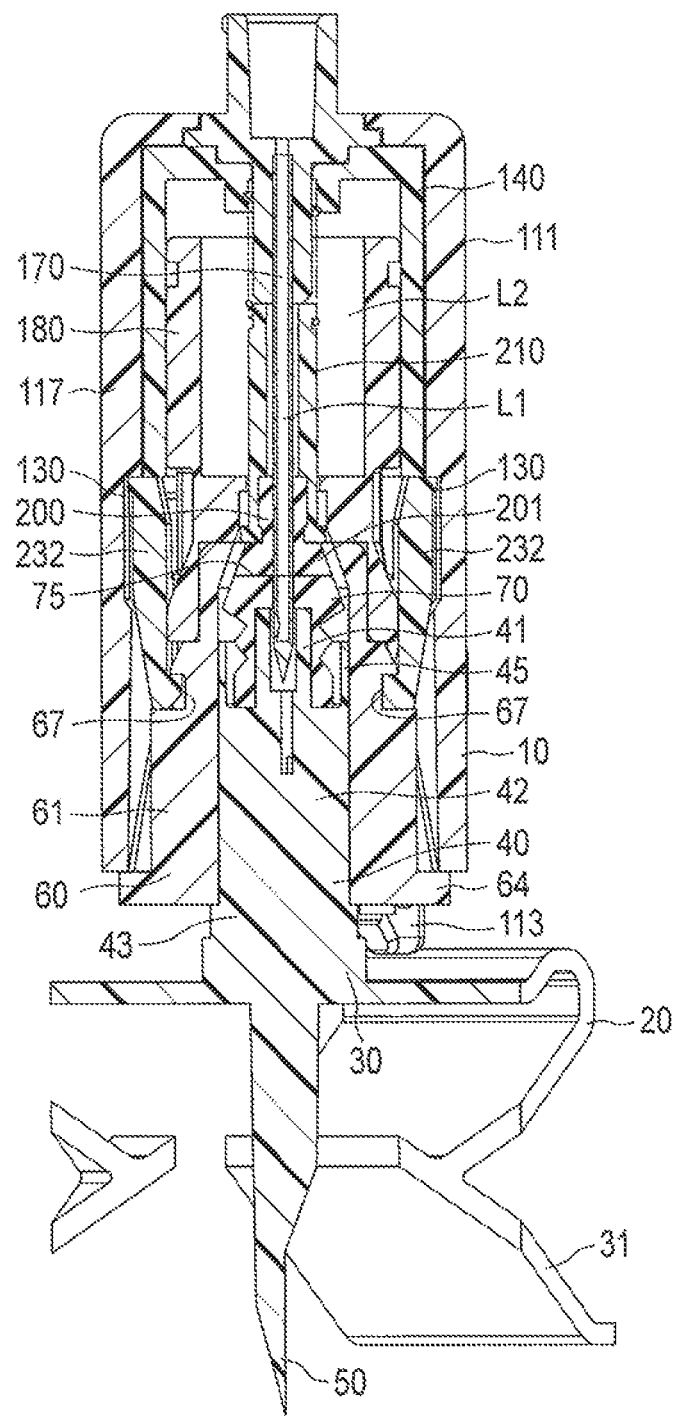
FIG. 20 is a cross-sectional view showing the container connector and the syringe connector that are connected in the state where the liquid flow path and the gas flow path are formed.

FIG. 19 is a cross-sectional view showing the container connector 20 and the syringe connector 100 that are connected in a state where the liquid flow path L1 and the gas flow path L2 are formed. FIG. 20 is a cross-sectional view showing the container connector 20 and the syringe connector 100 that are connected in the state where the liquid flow path L1 and the gas flow path L2 are formed. FIG. 20 is a cross-sectional view showing the state where the container connector 20 and the syringe connector 100 are cut along a cut plane rotated by 90 degrees from a cross section shown in FIG. 19 about the axis of the outer shell main body 111.

As shown in FIG. 1 to FIG. 3, the connection equipment 10 has the container connector 20 formed to be fixable to the container 5, and the syringe connector 100 formed to be fixable to a barrel 7 of the syringe 6 and removably fixed to the container connector 20.

In the present embodiment, as an example, an up-down direction is set to the connection equipment 10 based on a state where the container 5 is disposed downward and the syringe 6 is disposed upward. Note that an axial direction of an after-mentioned container cap 30 of the container connector 20 and an axial direction of the seal cap 60 are parallel to the up-down direction, and an axial direction of the after-mentioned outer shell main body 111 of the syringe connector 100 is parallel to the up-down direction.

Firstly, description will be made as to the container connector 20. As shown in FIG. 1 to FIG. 5, the container connector 20 has the container cap 30 formed to be fixable to the container 5, the seal cap 60 fixed to the container cap 30, and a container seal 70 provided in the seal cap 60.

The container cap 30 has a liquid flow path forming section L3 that constitutes a part of the liquid flow path L1 via which the interior of the container 5 communicates with an interior of the barrel 7 and through which a liquid (the chemical solution) can flow, and a gas flow path forming section L4 that constitutes a part of the gas flow path L2 via which the interior of the container 5 communicates with the interior of the air bag 160 that is a pressure adjustment section as described later and through which air can flow. Specifically, the container cap 30 has a container fixing section 31 formed to be fixable to the container 5, a container cap main body 40, and a needle section 50 formed to be insertable into the container 5.

The container fixing section 31 is configured to be fixable to the container 5 in a state where the needle section 50 is inserted in the plug of the mouth of the container 5 and the after-mentioned liquid flow path forming section L3 and the gas flow path forming section L4 communicate with the interior of the container 5. By the container fixing section 31, the container cap main body 40 is fixed to the container 5. For example, as shown in FIG. 2, the container fixing section 31 has a pair of holders 31a that hold the mouth of the container 5. The container fixing section 31 holds a neck of the container 5 by the pair of holders 31a and is therefore fixed to the container 5. Note that when the holders 31a are opened, the holding of the neck of the container 5 by the pair of holders 31a is released. Note that a constitution of the container fixing section 31 is not limited to a constitution including the pair of holders 31a.

The container cap main body 40 is formed in a columnar shape having a plurality of outer diameters. Specifically, the container cap main body 40 has a container cap small diameter section 41 formed at an upper end portion of the main body, a container cap intermediate diameter section 42 that is continuous with the container cap small diameter section 41, and a container cap large diameter section 43 that is continuous with the container cap intermediate diameter section 42. The container cap small diameter section 41, the container cap intermediate diameter section and the container cap large diameter section 43 are coaxially arranged.

A recess 44 for the small diameter section is formed in an upper surface of the container cap small diameter section 41. The recess 44 for the small diameter section is formed in a central portion of the upper surface of the container cap small diameter section 41. The recess 44 for the small diameter section constitutes a part of the liquid flow path forming section L3. A cylindrical peripheral wall section 45 is formed at an outer peripheral edge of an upper surface of the container cap intermediate diameter section 42. The peripheral wall section 45 has a gap where a part of the container seal 70 can be disposed, between the peripheral wall section and the container cap small diameter section 41. An upper end of the peripheral wall section 45 is lower than an upper end of the container cap small diameter section 41.

The needle section 50 is located below the container cap main body 40. The needle section 50 is formed in a columnar shape. The needle section 50 is disposed, for example, coaxially with the container cap main body 40. In the needle section 50, a lower end, i.e., a leading end when being inserted into the container 5 is formed as a sharp head.

Furthermore, the liquid flow path forming section L3 and the gas flow path forming section L4 are formed in the container cap main body 40 and the needle section 50. The liquid flow path forming section L3 is open in the leading end portion of the needle section 50 and a bottom surface of the recess 44 for the small diameter section. Specifically, the liquid flow path forming section L3 has a first section L3a that communicates with an interior of the recess 44 for the small diameter section and extends in an axial direction of the container cap main body 40, and a second section L3b that communicates with the first section L3a, is disposed at a position shifted in a radial direction from the first section L3a and extends in the axial direction of the container cap main body 40.

The gas flow path forming section L4 is disposed at a position shifted in the radial direction from the liquid flow path forming section L3, and is open to the leading end portion of the needle section 50. Specifically, the gas flow path forming section L4 has a third section L4a that extends in the axial direction of the container cap main body 40, and a fourth section L4b that communicates with the third section L4a and extends through the container cap small diameter section 41 in the radial direction to communicate with the gap between the section and the peripheral wall section 45.

The seal cap 60 is formed in a tubular shape to store the container cap main body 40 inside, and fixed to the container cap main body 40 at such a position that a lower end of the cap abuts on the container cap large diameter section 43. Furthermore, the seal cap 60 is formed so that the after-mentioned outer shell 110 of the syringe connector 100 can be unlocked from the stopper sleeve 230 and so that the seal cap can be locked with the stopper sleeve 230.

Specifically, the seal cap 60 is formed in the cylindrical shape having a plurality of outer diameters. A seal that can prevent the gas from leaking out of the lower end of the seal cap 60 is formed between an inner peripheral surface of the seal cap 60 and an outer peripheral surface of the container cap main body 40.

In the present embodiment, the seal cap 60 is formed in the cylindrical shape that fits in the container cap intermediate diameter section 42. When the container cap intermediate diameter section 42 fits in the seal cap 60, sealing is achieved. Note that the sealing is not limited to the above sealing. As another example, an O-ring may be provided as a seal.

As shown in FIG. 4 and FIG. 5, the seal cap 60 has a cylindrical seal cap base 61, a seal cap intermediate diameter section 62 formed on the seal cap base 61, and a seal cap small diameter section 63 formed on the seal cap intermediate diameter section 62. The seal cap base 61, the seal cap intermediate diameter section 62 and the seal cap small diameter section 63 are coaxially arranged.

The seal cap base 61 is formed movably in the after-mentioned outer shell 110 of the syringe connector 100. A seal cap protrusion 64 that protrudes outwardly in the radial direction is formed at a lower edge of the seal cap base 61. As shown in FIG. 3, the seal cap protrusion 64 is formed to abut on a lower edge of the outer shell 110 when the container connector 20 is inserted into the syringe connector 100, so that further intrusion of the container connector 20 into the outer shell 110 can be regulated. As an example, a plurality of seal cap protrusions 64 are formed. In the present embodiment, two seal cap protrusions 64 are formed. At the lower edge of the seal cap base 61, an after-mentioned locking section 113 is engaged in a portion between the two seal cap protrusions 64.

In an outer peripheral surface of the seal cap base 61, as shown in FIG. 4 and FIG. 5, there is formed a first guiding protrusion 65 that guides movement of the container connector 20 in the up-down direction in the outer shell 110 of the syringe connector 100. The first guiding protrusion is formed to be storable in a first guide groove 126 formed in the outer shell 110.

For example, a plurality of first guiding protrusions 65 are formed. In the present embodiment, two first guiding protrusions 65 are formed. Each of the first guiding protrusions 65 is disposed on a central portion of the seal cap protrusion 64 in a circumferential direction, and extends in the axial direction. An upper end of the first guiding protrusion 65 is formed substantially in a triangular shape in side view so that the upper end can smoothly intrude into the first guide groove 126 of the outer shell 110.

The seal cap intermediate diameter section 62 is formed to abut on the after-mentioned stopper sleeve 230 of the syringe connector 100 when the container connector 20 is inserted into the syringe connector 100 to reach a predetermined position in the syringe connector 100, so that the stopper sleeve 230 and the outer shell 110 can be unlocked. Specifically, an outer peripheral surface of a portion of the seal cap intermediate diameter section 62 which is above a middle portion of the section in the axial direction is formed in a conical surface 62a having a diameter that gradually decreases as being upward.

Further in the seal cap intermediate diameter section 62, a locking recess 67 is formed to engage with the stopper sleeve 230 when the container connector 20 is inserted into the syringe connector 100 to reach the predetermined position in the syringe connector 100. The locking recess 67 is formed by denting a portion of the outer peripheral surface of the seal cap intermediate diameter section 62 in the circumferential direction inwardly in the radial direction over a region from a lower end to a middle portion in the axial direction. An upper surface 67a that can engage with the stopper sleeve 230 is formed in an upper end portion of the locking recess 67.

The seal cap small diameter section 63 is formed in a diameter smaller than a diameter of an upper end of the seal cap intermediate diameter section 62. The seal cap small diameter section 63 is formed in a cylindrical shape that can fit in the after-mentioned head sleeve 180 of the syringe connector 100. As shown in FIG. 2, an inner peripheral surface 66 of the seal cap 60 is formed as a conical surface so that a diameter of an upper end portion 66a gradually decreases as being upward.

As shown in FIG. 2, the container seal 70 is formed in a bottomed tubular shape that can store therein the container cap small diameter section 41. The container seal 70 is provided on the container cap small diameter section 41 in a state where a bottom of the seal is disposed upward and the container cap small diameter section 41 is stored inside.

The container seal 70 is made of a resin such as a rubber or an elastomer and has flexibility. Furthermore, a hole formed by inserting an after-mentioned needle 170 of the syringe connector 100 into the seal can be liquid-tightly and air-tightly closed by resilience after the needle 170 is moved.

An inner diameter of the container seal 70 is set so that the container cap small diameter section 41 fits in the seal. When an inner peripheral surface of the container seal 70 comes in contact with an outer peripheral surface of the container cap small diameter section 41, a gap between the inner peripheral surface of the container seal 70 and the outer peripheral surface of the container cap small diameter section 41 is sealed.

A depth of the container seal 70 is larger than a length of the container cap small diameter section 41 in the axial direction. Consequently, as shown in FIG. 14, when the container connector 20 is not inserted in the syringe connector 100 and the container seal 70 is not urged downward, a gap is formed between a lower surface 72 of an upper wall section 71 of the container seal 70 and the upper end of the container cap small diameter section 41.

An upper end portion 73a of an outer peripheral surface 73 of the container seal 70 is formed as a conical surface that can fit with the conical surface of the upper end portion 66a of the inner peripheral surface 66 of the seal cap 60. When the upper end portion 73a of the container seal fits with the upper end portion 66a of the inner peripheral surface 66 of the seal cap 60, i.e., the conical surface of the container seal 70 comes in contact with the conical surface of the seal cap 60, an upper end opening of the container cap 30 is air-tightly and liquid-tightly sealed.

A portion below the upper end portion 73a formed as the conical surface in the outer peripheral surface 73 of the container seal 70 is formed in bellows so that the container seal 70 becomes easy to shrink when pressed downwardly. When the container seal 70 shrinks, the lower surface 72 of the upper wall section 71 abuts on the upper end of the container cap small diameter section 41, to liquid-tightly and air-tightly seal the upper end opening.

Next, description will be made as to the syringe connector 100. As shown in FIG. 1 to FIG. 3 and FIG. 6, the syringe connector 100 has the outer shell 110, the air bag 160 stored in the outer shell 110, the needle 170 fixed in the outer shell 110, the tubular head sleeve 180 that is stored movably in the outer shell 110 while storing therein a part of the needle 170, a needle seal 200 stored in the outer shell 110 and formed so that a lower end opening of the head sleeve 180 can be selectively sealed, the needle seal holder 210 stored in the outer shell 110 to hold the needle seal 200, an urging member 220 that urges the needle seal 200 toward the head sleeve 180, and the stopper sleeve 230 formed so that the head sleeve 180 can be selectively fixed to the outer shell 110 and so that the head sleeve 180 can be selectively fixed to the container connector 20.

The outer shell 110 has the outer shell main body 111, an air bag storage section 150 that stores the air bag 160, and the locking section 113 that can removably lock the outer shell main body 111 to the container connector 20.

The outer shell main body 111 has an outer shell ceiling wall 114, a syringe fixing section 115 which is formed in the outer shell ceiling wall 114 and to which the barrel 7 of the syringe 6 can be fixed, a needle fixing section 116 which is formed in the outer shell ceiling wall 114 and to which the needle 170 can be fixed, a tubular outer shell barrel section 117 formed at a rim of the outer shell ceiling wall 114, and a tubular inner sleeve 140 fixed in the outer shell main body 111.

The outer shell ceiling wall 114 is formed, for example, in a disk shape. A hole 114a is formed at a center of the outer shell ceiling wall 114. A ceiling wall protrusion 119 that protrudes downwardly to another region is formed in a lower surface of the outer shell ceiling wall 114. The ceiling wall protrusion 119 is formed in a columnar shape. The ceiling wall protrusion 119 is disposed coaxially with the outer shell ceiling wall 114.

The syringe fixing section 115 is formed in an upper surface of the outer shell ceiling wall 114 and formed in a tubular shape that protrudes upwardly from another region of the upper surface. The syringe fixing section 115 is formed to be fittable in a tip portion of the barrel 7. The syringe fixing section 115 is formed at the center of the outer shell ceiling wall 114, and an interior of the section communicates with the hole 114a of the outer shell ceiling wall 114. The syringe fixing section 115 has a syringe fixing section main body 120 formed in a cylindrical shape, and a syringe fixing section protrusion 121 formed at a rim of an upper end of the syringe fixing section main body 120 to protrude outwardly in the radial direction.

The syringe fixing section main body 120 is disposed, for example, coaxially with the outer shell ceiling wall 114. For example, a plurality of syringe fixing section protrusions 121 are formed. The syringe fixing section protrusion 121 has a predetermined length in a circumferential direction of the syringe fixing section main body 120. The syringe fixing section protrusion 121 is screwed into an internal thread formed at the tip portion of the barrel 7, to fix the syringe 6 to the syringe connector 100. Furthermore, the tubular tip portion of the barrel 7 provided on an inner peripheral side of the internal thread is inserted into the syringe fixing section main body 120, and an inner peripheral surface of the syringe fixing section main body 120 abuts on an outer peripheral surface of the tubular tip portion of the barrel 7, thereby sealing a gap between the tubular tip portion of the barrel 7 and an interior of the syringe fixing section main body 120.

The needle fixing section 116 is formed in a tubular shape that protrudes downwardly from the lower surface of the outer shell ceiling wall 114 so that the needle 170 is fixed inside. The needle fixing section 116 communicates with the hole 114a. The needle fixing section 116 is formed, for example, in a cylindrical shape. The needle fixing section 116 is disposed coaxially with the outer shell ceiling wall 114, i.e., coaxially with the outer shell main body 111.

Note that in the present embodiment, the syringe fixing section 115, a part of the outer shell ceiling wall 114 and the needle fixing section 116 are formed by a member 122 that is a member separate from the other section of the outer shell main body 111. In other words, the member 122 is fixed to the outer shell main body 111, thereby constituting the outer shell ceiling wall 114, the syringe fixing section 115 and the needle fixing section 116.

Specifically, a hole 123 that can store a part of the member 122 is formed in a central portion of the outer shell ceiling wall 114. An inner peripheral surface of the hole 123 has two inner diameters in an axial direction thereof. A lower end portion of the hole 123 is formed in a larger diameter. The member 122 has a base 124 that is partially stored in the hole 123, the syringe fixing section 115, and the needle fixing section 116. The base 124 is formed in a disk shape having three outer diameters. A lower end portion of the base 124 constitutes the ceiling wall protrusion 119 in a state where the member 122 is fixed in the hole 123.

A middle portion of the base 124 in the axial direction is formed in a diameter larger than a diameter of the ceiling wall protrusion 119, and stored in a large diameter section of the hole 123. This middle portion has an outer diameter that is equal to or slightly smaller than an inner diameter of the large diameter section of the hole 123. An upper end portion of the base 124 is formed in a diameter smaller than the diameter of the above described middle portion, and stored in a small diameter section of the hole 123. This upper end portion has an outer diameter that is equal to or slightly smaller than an inner diameter of the small diameter section of the hole 123. The base 124 having such a constitution is fixed to the hole 123, for example, by bonding, so that the hole 123 is air-tightly and liquid-tightly sealed.

The outer shell barrel section 117 is formed in a cylindrical shape with which the seal cap base 61 of the container connector 20 movably fits. The outer shell barrel section 117 is disposed coaxially with the outer shell ceiling wall 114. A communication hole 125 that communicates with an interior of the air bag storage section 150 is formed in an upper end portion of the outer shell barrel section 117.

The first guide groove 126 that movably stores the first guiding protrusion 65 of the seal cap 60 of the container connector 20 is formed in a part of a lower end portion of an inner peripheral surface 117a of the outer shell barrel section 117. The first guide groove 126 is open inwardly in the outer shell main body 111 in the radial direction. The first guide groove 126 is also open in a lower end of the outer shell barrel section 117. Through this lower end opening, the first guiding protrusion 65 can intrude into the first guide groove 126.

The first guide groove 126 has a length along which the groove can guide movement of the container connector 20 to at least a position where the liquid flow path L1 and the gas flow path L2 are formed. In the present embodiment, the first guide groove 126 has such a length that an upper end of the first guide groove 126 abuts on the first guiding protrusion 65 simultaneously when the seal cap protrusion 64 of the container connector 20 abuts on the lower end of the outer shell barrel section 117.

The first guide groove 126 extends in an axial direction of the outer shell 110. A width of the first guide groove 126 along a circumferential direction of the outer shell 110 has such a size that the first guiding protrusion 65 fits in the groove. The first guide groove 126 is formed so that an inner surface of the groove abuts on the first guiding protrusion 65 in the circumferential direction, thereby preventing rotation of the container connector 20. The first guide grooves 126 that correspond in number to the first guiding protrusions 65 are formed. In the present embodiment, two first guide grooves 126 are formed. The two first guide grooves 126 are disposed at 180 degrees away from each other in the circumferential direction.

In a middle portion of the inner peripheral surface of the outer shell barrel section 117 in the axial direction, which is aligned with the first guide groove 126 in the axial direction, there is formed a second guide groove 127 that movably stores an after-mentioned second guiding protrusion 182 of the head sleeve 180. The second guide groove 127 is open inwardly in the outer shell main body 111 in the radial direction. The second guide groove 127 extends in the axial direction of the outer shell main body 111. The second guide groove 127 has a length along which the groove can guide the movement of the container connector 20 to at least the position where the liquid flow path L1 and the gas flow path L2 are formed. In the present embodiment, the second guide groove 127 has such a length that an upper end of the second guide groove 127 abuts on the second guiding protrusion 182 simultaneously when the seal cap protrusion 64 of the container connector 20 abuts on the lower end of the outer shell barrel section 117.

A width of the second guide groove 127 along a circumferential direction of the outer shell main body 111 has such a size that the second guiding protrusion 182 fits in the groove. The second guide groove 127 is formed so that an inner surface of the groove abuts on the second guiding protrusion 182 in the circumferential direction and can thereby prevent rotation of the head sleeve 180. For example, a plurality of second guide grooves 127 are formed. In the present embodiment, two second guide grooves 127 are formed, and arranged at 180 degrees away from each other in the circumferential direction of the outer shell main body 111.

Furthermore, in the middle portion of the inner peripheral surface of the outer shell barrel section 117 in the axial direction, as shown in FIG. 14 and FIG. 15, a locking protrusion 128 is formed at a position shifted from the second guide groove 127 in the circumferential direction. The locking protrusion 128 protrudes inwardly in a radial direction of the outer shell main body 111. The locking protrusion 128 is formed to engage with the stopper sleeve 230, so that it is possible to inhibit upward movement of the head sleeve 180 from a state where a lower end opening of an after-mentioned second hole 192 of the head sleeve 180 is sealed with the needle seal 200.

For example, a plurality of locking protrusions 128 are formed. In the present embodiment, two locking protrusions 128 are formed. The two locking protrusions 128 are arranged at 180 degrees away from each other in a circumferential direction of the outer shell barrel section 117, and each locking protrusion is disposed at a position shifted by 45 degrees from the first guide groove 126 or the second guide groove 127 in the circumferential direction of the outer shell main body 111.

Furthermore, in the middle portion of the inner peripheral surface of the outer shell barrel section 117 in the axial direction, as shown in FIG. 16 and FIG. 17, an unlocking protrusion 129 is formed at a position shifted from the locking protrusion 128 in the circumferential direction. The unlocking protrusion 129 protrudes inwardly in the radial direction of the outer shell main body 111.

The unlocking protrusion 129 is formed to abut on the stopper sleeve 230, so that it is possible to disengage the stopper sleeve 230 from the locking recess 67 of the container connector 20, in a state where the liquid flow path L1 and the gas flow path L2 are not formed, an upper end opening of the seal cap 60 is sealed with the container seal 70 and the lower end opening of the second hole 192 of the head sleeve 180 is sealed with the needle seal 200.

A middle portion of the unlocking protrusion 129 in an axial direction of the outer shell barrel section 117 protrudes most inwardly in the radial direction of the outer shell main body 111, and the unlocking protrusion is formed in such a shape that a protruding amount inwardly from an upper end or a lower end to the middle portion in the radial direction gradually increases. For example, a plurality of unlocking protrusions 129 are formed. In the present embodiment, two unlocking protrusions 129 are formed. The two unlocking protrusions 129 are arranged at 180 degrees away from each other in the circumferential direction of the outer shell main body 111, and each unlocking protrusion is disposed at a position of 90 degrees away from the locking protrusion 128 in the circumferential direction.

Furthermore, in a portion of the inner peripheral surface of the outer shell barrel section 117 which is above the unlocking protrusion 129 in the axial direction, a stopper sleeve storage recess 130 that can store a part of the stopper sleeve 230 is formed. The stopper sleeve storage recess 130 is formed by denting a part of an inner peripheral surface of the outer shell main body 111 outwardly in the radial direction.

As shown in FIG. 1 and FIG. 2, a locking section storage recess 131 that stores a part of the locking section 113 is formed in the lower end portion of the outer shell barrel section 117. The locking section storage recess 131 is a hole opened in the lower end of the outer shell barrel section 117. For example, a plurality of locking section storage recesses 131 are formed. In the present embodiment, two locking section storage recesses 131 are formed. The two locking section storage recesses 131 are at 180 degrees away from each other in the circumferential direction of the outer shell 110, and are arranged at positions of 90 degrees away from the first guide groove 126 or the second guide groove 127 in the circumferential direction.

The outer shell main body 111 having such a constitution can be constituted, for example, by combining a plurality of members. In the present embodiment, the outer shell main body 111 can be constituted, for example, by fixing two outer shell constituting members 132. FIG. 3 shows the state where one of the outer shell constituting members 132 is removed. FIG. 7 shows an inner surface of the other outer shell constituting member 132.

The respective outer shell constituting members 132 have a similar shape. The outer shell constituting member 132 has a shape obtained by dividing the outer shell main body 111 into two via a plane, as a boundary, which passes along the axis of the outer shell main body 111 and the axis of the air bag storage section 150. The two outer shell constituting members 132 are fixed to each other by a lock mechanism 133. The lock mechanism 133 has, for example, a claw section formed in one of the outer shell constituting members 132, and an engagement section 134 formed in the other outer shell constituting member 132 to engage with the claw section.

As shown in FIG. 2 and FIG. 3, the inner sleeve 140 is fixed in the outer shell main body 111, and formed in a bottomed tubular shape. Specifically, the inner sleeve 140 has an inner sleeve ceiling wall 141, and a tubular inner sleeve barrel section 142 formed at a rim of the inner sleeve ceiling wall 141. The inner sleeve ceiling wall 141 is formed in a disk shape having an outer diameter equal to or slightly smaller than an inner diameter of the outer shell barrel section 117. In a central portion of the inner sleeve ceiling wall 141, a hole 144 that stores a part of the needle fixing section 116 and a part of the urging member 220 is formed. In an upper surface of the inner sleeve ceiling wall 141, a recess 143 that stores the ceiling wall protrusion 119 of the outer shell ceiling wall 114 is formed.

The inner sleeve barrel section 142 is formed in a cylindrical shape having an outer diameter equal to or slightly smaller than the inner diameter of the outer shell barrel section 117. A connecting section 145 partially stored in the communication hole 125 of the outer shell barrel section 117 and connected at its tip portion to the air bag 160 is formed in an upper end portion of the inner sleeve barrel section 142. The connecting section 145 protrudes outwardly in the radial direction from an upper end portion of an outer peripheral surface of the inner sleeve barrel section 142. The connecting section 145 constitutes a part of the gas flow path L2. As shown in FIG. 19 and FIG. 20, the connecting section 145 is disposed at a position that is not closed with the head sleeve 180, in a state where the head sleeve 180 moves upwardly in the outer shell main body 111 to form the liquid flow path L1 and the gas flow path L2 and a state where an after-mentioned second arm 232 of the stopper sleeve 230 is engaged in the locking recess 67 of the seal cap 60.

The inner sleeve 140 formed in this way is fixed in the outer shell 110, for example, with an adhesive, in a state where the upper surface of the inner sleeve ceiling wall 141 is in surface contact with the lower surface of the outer shell ceiling wall 114, a part of the needle fixing section 116 and a part of the urging member 220 are stored in the hole 144, the ceiling wall protrusion 119 is stored in the recess 143, and a part of the connecting section 145 is stored in the communication hole 125 of the outer shell barrel section 117. The inner sleeve 140 is disposed coaxially with the outer shell 110.

As shown in FIG. 3, the air bag storage section 150 is disposed away from the outer shell main body 111 in a direction orthogonal to the axial direction of the outer shell main body 111. In the present embodiment, the air bag storage section 150 is aligned with the outer shell main body 111 in a direction in which two first guide grooves 126 are arranged. The air bag storage section 150 is formed in a box shape having a space in which the air bag 160 can be stored. An appearance of the air bag storage section 150 is formed, for example, in a columnar shape, and the axis thereof is parallel to the axis of the outer shell main body 111. The air bag storage section 150 is fixed to the outer shell main body 111 by a coupling section 151. Note that in the present embodiment, the coupling section 151, the air bag storage section 150 and the outer shell main body 111 are integrally formed. Furthermore, in the air bag storage section 150, a transparent or translucent resin material is used, or an opening or a transparent window portion is provided in a part of a wall surface of the air bag storage section 150, so that the shape of the air bag 160 may be seen.

The air bag storage section 150 having the above constitution can be constituted, for example, by combining a plurality of members. In the present embodiment, the air bag storage section 150 is constituted by fixing two constituting members. In the present embodiment, as shown in FIG. 3 and FIG. 6, one of constituting members that constitute the air bag storage section 150 is formed integrally with the one outer shell constituting member 132 as well as a part of the coupling section 151. The other constituting member that constitutes the air bag storage section 150 is formed integrally with the other outer shell constituting member 132 as well as the other part of the coupling section 151. In other words, in the present embodiment, the outer shell main body 111, the air bag storage section 150 and the coupling section 151 are constituted by fixing the two outer shell constituting members 132.

When the locking section 113 is engaged with the container connector 20, as shown in FIG. 1 and FIG. 2, separation of the syringe connector 100 from the container connector 20 can be regulated in a state where the syringe connector 100 is connected to the container connector 20 to form the liquid flow path L1 and the gas flow path L2.

Specifically, when the container connector 20 is to be moved from the syringe connector 100 in the state where the liquid flow path L1 and the gas flow path L2 are formed, the locking section 113 engages with a lower end of the seal cap to regulate this movement. When the movement is regulated, the liquid flow path L1 and the gas flow path L2 are prevented from being divided.

The locking section 113 is stored in the locking section storage recess 131 as shown in FIG. 1 and FIG. 7. The locking section 113 has a locking section main body 153 formed in a plate shape long in the axial direction of the outer shell main body 111, and a fixing section 154 for the locking section which fixes the locking section main body 153 to the locking section storage recess 131.

An upper end portion of the locking section main body 153 is formed in an operating section 155 operable by an operator. In a lower end portion of the locking section main body 153, a claw section 156 for the locking section is formed which can engage with the lower edge of the seal cap base 61. The claw section 156 for the locking section is formed in a shape that protrudes inwardly in the radial direction of the outer shell main body 111. The claw section 156 for the locking section is located below a lower end of another portion of the outer shell barrel section 117. A surface 157 of the claw section 156 for the locking section on the inner side in the radial direction is formed as an inclined surface having an upper end that is closer to an axial side of the outer shell main body 111 than a lower end.

The fixing section 154 for the locking section fixes a side surface of the locking section main body 153 in the circumferential direction to a side surface of the locking section storage recess 131. The fixing section 154 for the locking section fixes the locking section main body 153 so that the main body is disposed on an inner side of an outer peripheral edge of a lower end of the seal cap base 61 in a state where the container connector 20 is stored in the syringe connector 100.

Furthermore, the locking section 113 is formed so that, when the operating section 155 is pressed inwardly in the radial direction in a state where the claw section 156 for the locking section engages with the lower end of the seal cap base 61, the locking section is movable to a position where the claw section 156 for the locking section disengages from the lower end of the seal cap base 61, by a leverage effect while an abutment portion between an inner surface of the locking section main body 153 and an outer surface of the seal cap base 61 functions as a fulcrum.

As shown in FIG. 6, the air bag 160 is stored in the air bag storage section 150. The air bag 160 is made of a thin-film resin material that is easily deformable along flow of air in and out of the bag. This air bag 160 is a pressure adjustment section of the present invention, and a pressure in the container 5 can be adjusted by the deformation of the air bag 160. The air bag 160 has a volume that is more than or equal to a volume of the barrel 7 of the syringe 6. For example, the air bag 160 has an appearance substantially similar to an inner space defined by an inner surface of the air bag storage section 150. The air bag 160 is connected to the connecting section 145 of the inner sleeve 140. The air bag 160 communicates with an interior of the outer shell main body 111 via the connecting section 145. Note that when unused, the air bag 160 is stored in a deflated state in the air bag storage section 150 because interior air is discharged to an outside. The air bag 160 shown in FIG. 6 is filled with air.

The needle 170 is formed in a tubular shape as shown in FIG. 2. The needle 170 is fixed to the needle fixing section 116 coaxially with the outer shell main body 111 while an upper end portion of the needle is stored in the needle fixing section 116. The needle 170 constitutes a part of the liquid flow path L1. In the present embodiment, the needle 170 is formed in a cylindrical shape, and has a lower end portion 171 closed. The lower end portion 171 is formed as a sharp head. A hole 172 via which an interior of the needle 170 communicates with the outside is formed in a lower end portion of an outer peripheral surface 173 of the needle 170. Note that the hole 172 is an example of an opening on a tip side of the needle 170. Note that in the present embodiment, the hole 172 is disposed at the lower end portion of the outer peripheral surface 173, i.e., a lower end portion of a portion of the needle 170 which is not formed as the sharp head. The hole 172 may be formed in a lower end portion of the needle 170, i.e., in a portion formed as the sharp head. In short, the hole 172 may only be disposed on the tip side of the needle 170.

The head sleeve 180 is formed in a tubular shape that is movable in the inner sleeve 140. As shown in FIG. 8 to FIG. 10, the head sleeve 180 has a head sleeve main body 181 formed in a cylindrical shape, and the second guiding protrusion 182 formed on an outer peripheral surface of the head sleeve main body 181 to protrude outwardly in the radial direction.

The head sleeve main body 181 is formed in a cylindrical shape that movably fits in an inner peripheral surface of the inner sleeve 140. A seal that prevents a gas from leaking out of a lower end of the inner sleeve 140 is provided between an outer peripheral surface 183 of the head sleeve main body 181 and an inner peripheral surface 146 of the inner sleeve 140. This seal may be, for example, an O-ring. Alternatively, when the head sleeve main body 181 fits in the inner sleeve 140, i.e., when the outer peripheral surface 183 comes in contact with the inner peripheral surface 146 of the inner sleeve 140, a gap between the outer peripheral surface 183 and the inner peripheral surface 146 may be sealed.

An annular groove 184 is formed in an upper end portion of the outer peripheral surface 183. In a lower end portion of the outer peripheral surface 183, there are formed a first arm storage recess 185 that can store a part of an after-mentioned first arm 231 of the stopper sleeve 230, and a second arm storage recess 186 that can store a part of the after-mentioned second arm 232 of the stopper sleeve 230.

The first arm storage recess 185 is formed by denting a part of the outer peripheral surface 183 inwardly in the radial direction. The first arm storage recess 185 is formed so that a depth of the recess in the radial direction gradually increases from a lower end toward an upper end of the recess. For example, a plurality of first arm storage recesses 185 are formed. In the present embodiment, two first arm storage recesses 185 are formed. The two first arm storage recesses 185 are disposed at 180 degrees away from each other in a circumferential direction of the head sleeve main body 181.

The second arm storage recess 186 is formed by denting a part of the outer peripheral surface 183 inwardly in the radial direction. The second arm storage recess 186 is formed so that a depth of the recess in the radial direction gradually increases from a lower end toward an upper end of the recess. For example, a plurality of second arm storage recesses 186 are formed. In the present embodiment, two second arm storage recesses 186 are formed. The two second arm storage recesses 186 are disposed at 90 degrees away from the first arm storage recess 185 in the circumferential direction of the head sleeve main body 181.

Furthermore, a fixing protrusion storage recess 187 that stores an after-mentioned fixing protrusion 236 of the stopper sleeve 230 is formed in the lower end portion of the outer peripheral surface 183. The fixing protrusion storage recess 187 is formed by denting a part of the outer peripheral surface 183 inwardly in the radial direction.

The fixing protrusion storage recess 187 has an inlet 188 which is open in a lower end of the head sleeve main body 181 and through which the fixing protrusion 236 passes when the stopper sleeve 230 is fixed to the head sleeve 180, and a holder 189 extending in the circumferential direction of the head sleeve main body 181 and holding the fixing protrusion 236 intruded through the inlet 188. The holder 189 communicates with the inlet 188, and is formed above the inlet 188. The holder 189 is formed in a shape longer than a shape of the inlet in the circumferential direction of the head sleeve main body 181.

For example, a plurality of fixing protrusion storage recesses 187 formed in this way are formed. In the present embodiment, four fixing protrusion storage recesses 187 are formed. The four fixing protrusion storage recesses 187 are arranged via an equal space in the circumferential direction of the head sleeve main body 181, and each recess communicates with the first arm storage recess 185 or the second arm storage recess 186.

The second guiding protrusion 182 is formed in a middle portion of the outer peripheral surface 183 in the axial direction. The second guiding protrusion 182 is stored in the second guide groove 127 of the outer shell barrel section 117. Furthermore, the second guiding protrusion 182 is formed movably in the second guide groove 127. For example, a plurality of second guiding protrusions 182 are formed. In the present embodiment, two second guiding protrusions 182 are formed. The two second guiding protrusions 182 are disposed at positions of 45 degrees away from the first arm storage recess 185 in a circumferential direction of the head sleeve 180. For example, the second guiding protrusion 182 is formed in a rectangular parallelepiped shape.

As shown in FIG. 9 and FIG. 10, a hole 190 in the head sleeve main body 181 is formed as a hole having a plurality of inner diameters. The hole 190 has a first hole section 191 formed in a lower end portion and including a lower end opening of the hole 190, a second hole section 192 formed above the first hole section 191 and communicating with the first hole section 191, a third hole section 193 formed above the second hole section 192 and communicating with the second hole section 192, and a fourth hole section 194 formed above the third hole section 193 and including an upper end opening of the hole 190. These hole sections 191, 192, 193 and 194 are coaxially arranged.

The first hole section 191 is formed to be engageable with the seal cap small diameter section 63 of the seal cap 60. An inner peripheral surface 191*a* of the first hole section 191 is formed so that a cross section orthogonal to the axial direction is circular. A portion other than a lower end portion 191*b* in the inner peripheral surface 191*a* has the same cross section in the axial direction. The lower end portion 191*b* of the inner peripheral surface 191*a* of the first hole section 191 is formed in a conical surface having a diameter that gradually increases as being downward. A depth of the first hole section 191 in the axial direction is as large as a length of the seal cap small diameter section in the axial direction. An upper surface of the first hole section 191 is formed as a flat surface orthogonal to the axial direction of the hole 190.

The second hole section 192 is formed in a diameter smaller than a diameter of the first hole section 191. An inner peripheral surface 192*a* of the second hole section 192 is formed so that a cross section orthogonal to the axial direction is circular. A portion other than a lower end portion 192*b* in the inner peripheral surface 192*a* has the same cross section in the axial direction. The second hole section 192 is formed so that an after-mentioned holder protrusion 212 of the needle seal holder 210 and an after-mentioned seal section 201 of the needle seal 200 can be stored. The lower end portion 192*b* of the inner peripheral surface 192*a* is formed as a conical surface having a diameter that gradually increases as being downward and that can abut on an outer peripheral surface of the seal section 201.

The third hole section 193 is formed in a diameter smaller than the diameter of the second hole section 192. An inner peripheral surface 193*a* of the third hole section 193 is formed so that a cross section orthogonal to the axial direction is circular. The inner peripheral surface 193*a* has the same cross section in the axial direction. Furthermore, the third hole section 193 movably stores a part of the needle seal holder 210.

The fourth hole section 194 is formed in a diameter larger than the diameter of the third hole section 193. A cross section of an inner peripheral surface 194*a* of the fourth hole section 194 which is orthogonal to the axial direction is circular. The inner peripheral surface 194*a* has the same cross section in the axial direction. Furthermore, the fourth hole section 194 is formed so that a part of the needle seal holder 210 can be stored.

The head sleeve 180 having such a constitution is stored in the inner sleeve 140, and the second guiding protrusion 182 is stored in the second guide groove 127 of the outer shell barrel section 117.

As shown in FIG. 2, the needle seal 200 is supported in the outer shell main body 111 by the needle seal holder 210 and the urging member 220 movably in the axial direction of the outer shell main body 111. The needle seal 200 is formed so that the second hole section 192 of the head sleeve 180 can be selectively sealed. The needle seal 200 is made of a resin such as a rubber or an elastomer, and a hole formed by the needle 170 is formed to be liquid-tightly and air-tightly sealable by the resilience after the needle 170 is moved.

Specifically, the needle seal 200 has the seal section 201 that fits in a lower end portion of the second hole section 192, i.e., a portion where an inner peripheral surface of the second hole section is formed as a conical surface, the seal section having an outer peripheral surface formed as a conical surface, and the needle seal has a shaft section 202 disposed coaxially with the seal section 201 and extending upwardly from an upper end of the seal section 201.

The seal section 201 is elastically deformed and can be accordingly stored in a portion above the lower end portion of the second hole section 192 (the portion where the inner peripheral surface is formed as the conical surface). A lower end surface 203 of the seal section 201 is formed as a surface that can come in surface contact with an upper end surface 75 of the container seal 70 of the container connector 20. The lower end surface 203 is formed, for example, as a flat surface orthogonal to an axial direction of the seal section 201. The lower end surface 203 has the same circular shape and the same area as in the upper end surface 75 of the container seal 70.

The seal section 201 fits in the lower end portion of the second hole section 192, i.e., the conical surface of the seal section 201 comes in contact with the lower end portion 192*b* formed as the conical surface of the inner peripheral surface 192*a* of the second hole section 192, so that the second hole section 192 is sealed. The needle seal 200 moves downwardly to the head sleeve 180 to form a gap between the outer peripheral surface of the seal section 201 and the inner peripheral surface of the second hole section 192. This gap unseals the second hole section 192. This gap constitutes a part of the gas flow path L2.

The shaft section 202 is formed in a columnar shape having an outer diameter smaller than an inner diameter of the third hole section 193. A storage recess 204 that can store a part of the needle 170 is formed in an upper surface of the shaft section 202. Furthermore, a part of the shaft section 202 is formed in a large diameter section 205 that fits in the needle seal holder 210 and can be fixed to the needle seal holder 210. Furthermore, the needle seal 200 has such a length that a portion where the hole 172 of the needle 170 is formed is stored in the shaft section 202 and that a part of the seal is stored in the storage recess 204, in a state where the after-mentioned first arm 231 of the stopper sleeve 230 engages with the locking protrusion 128 to regulate the movement of the head sleeve 180 as shown in FIG. 14.

Consequently, in the state shown in FIG. 14, the hole 172 is liquid-tightly and air-tightly sealed with the needle seal 200.

As shown in FIG. 2, the needle seal holder 210 has a tubular shape that can store a part of the needle 170 therein, and the large diameter section 205 of the needle seal 200 is fixably formed in a lower end portion of the holder. Specifically, as shown in FIG. 11 and FIG. 12, the needle seal holder 210 has a holder main body 211 formed in a cylindrical shape, and a plurality of holder protrusions 212 formed in a lower end portion of an outer peripheral surface of the holder main body 211 to protrude outwardly in the radial direction.

As shown in FIG. 2, the holder main body 211 has an outer diameter smaller than the inner diameter of the third hole section 193, and is formed movably in the third hole section 193 in the axial direction. Consequently, a gap through which a gas such as air can flow is formed between the outer peripheral surface of the holder main body 211 and an inner peripheral surface of the third hole section 193.

In an upper end portion of the outer peripheral surface of the holder main body 211, a spiral groove 215 to which a coil spring of an example of the urging member 220 can be fixed is formed. In a portion of the holder main body 211 which is above the holder protrusion 212, a hole 213 extending through the main body in the radial direction is formed. For example, a plurality of holes 213 are formed, and spaced apart, for example, via an equal space in the circumferential direction. The hole 213 is formed, for example, in a rectangular shape seen in the radial direction. In a lower end portion of an inner peripheral surface of the holder main body 211, a fixing groove 214 to which the large diameter section 205 of the needle seal 200 can be fixed is formed.

The holder protrusions 212 are arranged apart, for example, via an equal space in the circumferential direction of the holder main body 211. Furthermore, the holder protrusion 212 is aligned with a portion between two holes 213 in the axial direction. As shown in FIG. 2 and FIG. 3, the needle seal holder 210 constituted in this way has such a length that the lower end opening of the second hole section 192 sealed with the seal section 201 can be unsealed, in a state where the head sleeve 180 is moved upward in the outer shell 110 until an upper end of the needle seal holder abuts on a lower end of the needle fixing section 116 and the second guiding protrusion 182 abuts on the upper end of the second guide groove 127.

As shown in FIG. 2, the urging member 220 is formed so that the needle seal 200 can be urged upward to bring the seal section 201 into contact with the second hole section 192, thereby sealing the second hole section 192. As an example of the urging member 220 in the present embodiment, a coil spring is used. The urging member 220 is fixed to the needle fixing section 116 and the groove 215 of the upper end portion of the needle seal holder 210. The urging member 220 urges the needle seal 200 upwardly via the needle seal holder 210. The urging member 220 may have an urging force to such an extent that the lower end opening of the second hole section 192 can be sealed with the seal section 201.

As shown in FIG. 3, the stopper sleeve 230 is fixed to an outer peripheral surface of the head sleeve 180. The stopper sleeve 230 is formed to selectively regulate the movement of the head sleeve 180 to the outer shell 110, and is formed so that the head sleeve 180 can be selectively fixed to the seal cap 60.

Specifically, the stopper sleeve 230 has the first arm 231 formed to be engageable with the locking protrusion 128 of the outer shell barrel section 117, the second arm 232 that can engage in the locking recess 67 of the seal cap 60, and a coupling section 233 that couples the first arm 231 to the second arm 232.

As shown in FIG. 14, the first arm 231 is formed to be engageable with the locking protrusion 128 in a state where the head sleeve 180 is located in the lower end portion of the outer shell 110 and the lower end opening of the second hole section 192 is sealed with the seal section 201. The first arm 231 engages with the locking protrusion 128 to prevent the head sleeve 180 from being moved upwardly in the outer shell 110 in the state where the lower end opening of the second hole section 192 is sealed with the seal section 201.

Specifically, as shown in FIG. 13, the first arm 231 fixed to the outer peripheral surface of the head sleeve 180 is formed in a plate shape that is long in an axial direction of the head sleeve 180. The fixing protrusion 236 is formed in a central portion of a surface 235 of the first arm 231 which is opposite to the head sleeve 180. An upper end surface of the first arm 231 is formed to be abuttable on the locking protrusion 128 from underside towards the upside. The upper end surface is formed, for example, as a flat surface.

In a lower end portion of the surface 235 of the first arm 231, a first arm protrusion 237 is formed. A lower end surface 238 of the first arm protrusion 237 is formed to be abuttable on the conical surface 62a of the outer peripheral surface of the seal cap intermediate diameter section 62 of the seal cap 60. The lower end surface 238 is formed as an inclined surface that is inclined to the axis of the head sleeve 180 in a state where the stopper sleeve 230 is fixed to the head sleeve 180.

Furthermore, the first arm protrusion 237 is formed so that the lower end surface 238 abuts on the conical surface 62a of the seal cap intermediate diameter section 62, to rotate the first arm 231 so that the upper end surface of the first arm moves toward the head sleeve 180. Consequently, the first arm 231 can be disengaged from the locking protrusion 128. For example, a plurality of first arm protrusions 237 are formed. In the present embodiment, two first arm protrusions 237 are formed. For example, a plurality of first arms 231 are formed. In the present embodiment, two first arms 231 are formed.

As shown in FIG. 17, the second arm 232 engages with the seal cap 60, so that the seal cap small diameter section 63 fits in the first hole section 191 of the head sleeve 180. It is possible to maintain a state where the upper end surface 75 of the container seal 70 is in contact closely with the lower end surface 203 of the seal section 201 of the needle seal 200.

Specifically, as shown in FIG. 13, the second arm 232 fixed to the outer peripheral surface of the head sleeve 180 is formed in a plate shape that is long in the axial direction of the head sleeve 180. A second arm protrusion 240 that can engage in the locking recess 67 of the seal cap 60 is formed in a lower end portion of a surface 239 of the second arm 232 on a head sleeve 180 side.

An upper surface 241 of the second arm protrusion 240 is formed to be engageable with the upper surface 67a of the locking recess 67 of the seal cap 60. A lower end surface 242 of the second arm protrusion 240 is formed as an inclined surface that is inclined to the axis of the head sleeve 180 in the state where the stopper sleeve 230 is fixed to the head sleeve 180.

The fixing protrusion 236 is formed in a central portion of the surface 239. A surface 243 of the second arm 232 which is opposite to the head sleeve 180 is formed to be abuttable on the unlocking protrusion 129 of the outer shell barrel section 117.

Specifically, the second arm 232 is formed to have a substantially trapezoidal cross section so that a central portion of the surface 243 in the circumferential direction protrudes outwardly. The second arm is formed so that a central portion 243a of the surface 243 in the circumferential direction can abut on the unlocking protrusion 129. When the central portion 243a abuts on the unlocking protrusion 129, the second arm 232 is rotated so that the second arm protrusion 240 moves away from the head sleeve 180 to move the second arm protrusion 240 out of the locking recess 67. Thus, the second arm is formed so that the second arm protrusion 240 can be disengaged from the locking recess 67. Furthermore, for example, a plurality of second arms 232 are formed. In the present embodiment, two second arms 232 are formed.

In the second arm 232 formed in this way, as shown in FIG. 14, the head sleeve 180 is disposed downward in the outer shell main body 111 and the first arm 231 is engaged with the locking protrusion 128. In this state, as shown in FIG. 16, the middle portion of the unlocking protrusion 129 in the axial direction of the outer shell barrel section 117 (a portion that protrudes most inwardly in a radial direction of the outer shell barrel section 117) abuts on an upper portion of the central portion 243a of the surface 243. Consequently, the second arm 232 is rotated to a position where the second arm protrusion 240 disengages from the locking recess 67 of the seal cap 60.

Furthermore, when the stopper sleeve 230 moves upwardly, the second arm 232 moves upwardly from the unlocking protrusion 129. Consequently, the middle portion that is the most protruding portion of the unlocking protrusion 129 abuts on a lower end portion of the central portion 243a of the surface 243 of the second arm 232.

The second arm 232 is formed to be rotatable to a position where the second arm protrusion 240 engages in the locking recess 67 of the seal cap 60 by means of abutment of the unlocking protrusion 129 on a lower end portion of the second arm and resilience of the coupling section 233.

The coupling section 233 couples the first arm 231 to the second arm 232. The coupling section 233 has flexibility, and is formed to be twisted so that the first arm 231 can rotate and the second arm 232 can rotate. The coupling section 233 places the first arm 231 at a position where the first arm can engage with the locking protrusion 128 in a state where any external force is not applied to the first arm 231. The coupling section 233 places the second arm 232 at a position where the second arm can engage in the locking recess 67 of the seal cap 60 in a state where any external force is not applied to the second arm 232.

The stopper sleeve 230 constituted in this way is formed in an annular shape in which the first arm 231 and the second arm 232 are alternately arranged in the circumferential direction. The first arm 231 and the second arm 232 are disposed apart in the circumferential direction.

The stopper sleeve 230 constituted in this way is rotated at a predetermined angle in the circumferential direction, after the fixing protrusion 236 is inserted from the inlet 188 of the fixing protrusion storage recess 187 of the head sleeve main body 181 in an axial direction of the head sleeve main body 181 and intruded into the holder 189. By this rotation, the fixing protrusion 236 is located so that the fixing protrusion is not aligned with the inlet 188. Consequently, the fixing protrusion does not fall out of the inlet 188. Thus, the stopper sleeve 230 is fixed to the head sleeve 180.

Furthermore, in a state where the fixing protrusion 236 is stored in the holder 189 as described above, the first arm 231 is disposed opposite to the first arm storage recess 185, and the second arm 232 is disposed opposite to the second arm storage recess 186.

The first arm 231 is disposed opposite to the first arm storage recess 185, so that a part of an upper portion of the first arm 231 is stored in the first arm storage recess 185 during rotation. Specifically, the first arm storage recess 185 is a part of a movement margin during the rotation of the first arm 231, and hence, the first arm 231 can rotate to a position where an upper end of the first arm disengages from the locking protrusion 128. The second arm 232 is disposed opposite to the second arm storage recess 186, so that a part of an upper portion of the second arm 232 is stored in the second arm storage recess 186 during rotation. Specifically, the second arm storage recess 186 is a part of a movement margin during the rotation of the second arm 232, and hence, the second arm 232 can rotate to a position where the second arm protrusion 240 disengages from the locking recess 67.

Next, description will be made as to an operation of connecting the syringe connector 100 to the container connector 20 and forming the liquid flow path L1 and the gas flow path L2. The container connector 20 is fixed to the container 5 by the container fixing section 31 in the state where the needle section 50 is inserted in the plug of the mouth of the container 5.

In a state where the syringe connector 100 is not connected to the container connector 20 as shown in FIG. 14, the head sleeve 180 is located in a lower end portion of an interior of the outer shell 110. Furthermore, the urging member 220 urges the stopper sleeve 230 upwardly via the needle seal holder 210, the needle seal 200 and the head sleeve 180, so that the first arm 231 of the stopper sleeve 230 engages with the locking protrusion 128. Furthermore, as shown in FIG. 16, the second arm 232 of the stopper sleeve 230 abuts on the unlocking protrusion 129 of the outer shell barrel section 117, and is rotated to the position where the second arm protrusion 240 disengages from the locking recess of the seal cap 60. A part of the second arm 232 is stored in the second arm storage recess 186 of the head sleeve 180.

In the state where the first arm 231 is engaged with the locking protrusion 128, the lower end opening of the second hole section 192 of the head sleeve 180 is sealed with the seal section 201 of the needle seal 200. Furthermore, a part of the seal section 201 is deformed inwardly in the radial direction by the second hole section 192, and stored in the second hole section 192. A tip portion of the needle 170 in which the hole 172 is formed is stored in the shaft section 202 of the needle seal 200. Consequently, the hole 172 of the needle 170 is sealed with the needle seal 200, and is air-tightly and liquid-tightly sealed.

In the state where the container connector 20 is not connected to the syringe connector 100, as shown in FIG. 14, a tip opening of the seal cap 60 is sealed with the container seal 70.

Next, as shown in FIG. 15 and FIG. 16, the seal cap small diameter section 63 of the seal cap 60 is inserted into the first hole section 191 of the head sleeve 180. As shown in FIG. 15, by the time when the upper end surface 75 of the container seal 70 comes in contact closely with the lower end surface 203 of the seal section 201, the lower end surface 238 of the first arm protrusion 237 of the first arm 231 of the stopper sleeve 230 abuts on the conical surface 62a of the seal cap intermediate diameter section 62.

When the syringe connector 100 is further lowered from this state, the first arm protrusion 237 is guided by the conical surface 62a and moved outwardly in the radial direction. With the movement of the first arm protrusion 237 outwardly in the radial direction, the first arm 231 rotates. In the state where the upper end surface 75 of the container seal 70 is in contact closely with the lower end surface 203 of the seal section 201, the first arm 231 is guided by the conical surface 62a and rotated to the position where the first arm disengages from the locking protrusion 128. At this time, a part of the first arm 231 is stored in the first arm storage recess 185 of the head sleeve 180. When the first arm 231 disengages from the locking protrusion 128, the head sleeve 180 can be moved upwardly in the outer shell main body 111.

As for the second arm 232, as shown in FIG. 16, when the syringe connector 100 is lowered until the upper end surface 75 of the container seal 70 comes in contact closely with the lower end surface 203 of the seal section 201, the second arm protrusion 240 is disposed opposite to the locking recess 67.

Next, as shown in FIG. 17, when the syringe connector 100 is further lowered, the container connector 20, the head sleeve 180, the needle seal 200 and the needle seal holder 210 integrally move upwardly in the outer shell main body 111. When the needle seal 200 moves upwardly by a predetermined distance in the outer shell main body 111, the needle 170 moves downwardly to the needle seal 200.

As shown in FIG. 18, when the syringe connector 100 is further lowered, the container connector 20, the head sleeve 180, the needle seal 200 and the needle seal holder 210 move further upwardly in the outer shell main body 111, the needle 170 extends through the needle seal 200 and pierces the container seal 70. Note that a gap between the needle 170 and the needle seal 200 is liquid-tightly and air-tightly sealed when the needle seal 200 comes in contact closely with the needle 170. Similarly, a gap between the needle 170 and the container seal 70 is liquid-tightly and air-tightly sealed when the container seal 70 comes in contact closely with the needle 170.

In a state where the needle 170 extends through the needle seal 200, the second arm 232 moves upwardly relative to the unlocking protrusion 129. In this process of moving the second arm 232 upwardly relative to the unlocking protrusion 129, an abutment position of a middle portion of the unlocking protrusion 129 in the central portion 243a of the surface 243 of the second arm 232, which protrudes most inwardly in the radial direction of the outer shell main body 111, moves downwardly. Due to the downward movement of this abutment position, an urging force to urge the second arm protrusion 240 outwardly in the radial direction of the outer shell main body 111 decreases.

In the state where the needle 170 extends through the needle seal 200, the second arm 232 urged inwardly in the radial direction by the abutment on the unlocking protrusion 129 of the outer shell barrel section 117 is released. The second arm is rotated by elasticity (resilience) of the coupling section 233 and the abutment of the second arm protrusion 240 on the lower end portion of the second arm 232, to engage the second arm protrusion 240 in the locking recess 67. Specifically, the stopper sleeve 230 and the seal cap 60 are fixed to each other before the needle 170 extends through the needle seal 200.

When the syringe connector 100 is further lowered, the upper end of the needle seal holder 210 abuts on the needle fixing section 116. By this abutment, further upward movement of the needle seal holder 210, the needle seal 200 and the container seal 70 in the outer shell main body 11 is regulated.

When the syringe connector 100 is further lowered after the needle seal holder 210 abuts on the needle fixing section 116, the head sleeve 180, the seal cap 60 and the container cap 30 move further upwardly relative to the needle seal 200 and the container seal 70 in the outer shell main body 11.

When the head sleeve 180 moves upwardly relative to the needle seal 200, a gap is formed between the seal section 201 and the inner peripheral surface 192a of the second hole section 192. Through this gap, the lower end opening of the second hole section 192 is unsealed.

Furthermore, when the seal cap 60 and the container cap 30 move upwardly relative to the container seal 70, a gap is formed between the outer peripheral surface 73 of the container seal 70 and the inner peripheral surface 66 of the seal cap 60. These gaps communicate with each other. Through these gaps, the upper end opening of the seal cap 60 is unsealed.

Additionally, when the seal cap 60 and the container cap 30 move upwardly relative to the container seal 70, the container seal 70 is compressed between the seal cap intermediate diameter section 62 and the seal section 201. When the container seal 70 is compressed, the lower surface of the upper wall section 71 of the container seal 70 comes close to the upper end of the container cap small diameter section 41.

When the syringe connector 100 is further lowered, as shown in FIG. 2, the claw section 156 for the locking section 113 rides across the lower end of the seal cap base 61, to move inwardly in the radial direction. The claw section 156 for the locking section rides across the lower end of the seal cap base 61 to move inwardly in the radial direction, thereby obtaining a state where the claw section can be engaged with a portion between two seal cap protrusions 64 of the lower end of the seal cap 60. Specifically, when the syringe connector 100 is pulled upwardly from this state relative to the container connector 20, the claw section 156 for the locking section engages with the lower end of the seal cap base 61, and this movement is regulated.

When the syringe connector 100 is further lowered, as shown in FIG. 19 and FIG. 20, the upper end of the first arm 231 and an upper end of the second arm 232 abut on the inner sleeve 140. Furthermore, the first guiding protrusion 65 abuts on the upper end of the first guide groove 126. Additionally, the second guiding protrusion 182 abuts on the upper end of the second guide groove 127. In addition, the seal cap protrusion 64 of the seal cap base 61 abuts on the lower end of the outer shell barrel section 117. By these abutments, the movement of the head sleeve 180 and the container connector 20 in the outer shell main body 11 is regulated. Specifically, the syringe connector 100 is lowered to a so-called bottom reached state.

In this bottom reached state, when the container seal 70 abuts on a tip opening of the container cap small diameter section 41, the tip opening of the container cap small diameter section 41 is liquid-tightly sealed with the container seal 70. Furthermore, the hole 172 of the needle 170 is disposed in the recess 44 for the container cap small diameter section 41. Consequently, the needle 170 communicates with the liquid flow path forming section L3, and the liquid flow path L1 is formed. Furthermore, the gas flow path forming section L4, an interior of the seal cap 60, the second hole section 192, the third hole section 193 and the connecting section 145 communicate, thereby forming the gas flow path L2.

The operator recognizes that the syringe connector 100 is lowered to reach the bottom and that the liquid flow path L1 and the gas flow path L2 are accordingly formed. When the syringe connector 100 is lowered to reach the bottom, the operator operates the syringe 6, to collect the chemical solution from the container 5. The liquid is moved from the container 5 to the syringe 6 through the liquid flow path L1.

An example of a collection method of this chemical solution will be specifically described. An amount of air which is equal to an amount of the chemical solution to be collected is put in the barrel 7 of the syringe 6 in advance. Then, the syringe connector 100 is lowered to reach the bottom, and a piston of the syringe 6 is pushed inside, to inject the air from the barrel 7 into the container 5 via the liquid flow path L1. In this case, a pressure in the container 5 rises, the air moves from the container 5 to the air bag 160 via the gas flow path L2, and the pressure in the container 5 is balanced. Then, the container 5 is disposed above, and the syringe 6 is disposed below. In this state, when the piston of the syringe 6 is pulled as much as the amount of the chemical solution to be collected, the chemical solution in the container 5 moves to the barrel 7 via the liquid flow path L1, and the chemical solution is collected. In this case, the pressure in the container 5 decreases, the air in the air bag 160 moves to the container 5 via the gas flow path L2, and the pressure in the container 5 is balanced.

Next, an operation of disconnecting the container connector 20 from the syringe connector 100 will be described. When disconnecting the container connector 20 from the syringe connector 100, the operator presses the operating section 155 of the locking section 113 inwardly in the radial direction to a position where the claw section 156 for the locking section disengages from the lower end of the seal cap base 61.

Next, the operator pulls the syringe connector 100 upwardly. The head sleeve 180 is fixed to the seal cap 60 by the second arm 232 of the stopper sleeve 230. Consequently, when the syringe connector 100 is pulled upwardly, the outer shell 110, the needle 170, the needle seal 200 and the needle seal holder 210 move upwardly relative to the head sleeve 180. With the upward movement of the needle seal 200, the container seal 70 returns from a shrunk state to an original state by the resilience. Consequently, the upper wall section 71 of the container seal 70 moves upwardly in the seal cap 60.

When the syringe connector 100 is further pulled upwardly, as shown in FIG. 17 and FIG. 18, the outer peripheral surface of the seal section 201 of the needle seal 200 abuts on the conical surface of the second hole section 192. By this abutment, the second hole section 192 is sealed. Furthermore, the upper wall section 71 of the container seal 70 abuts on the upper end portion 66a formed in the conical surface of the inner peripheral surface 66 of the seal cap 60. By this abutment, the upper end opening of the seal cap 60 is sealed.

Thus, the upper end opening of the seal cap 60 is sealed, and the lower end opening of the second hole section 192 of the head sleeve 180 is sealed. Consequently, the gas flow path L2 is divided, a portion of the gas flow path L2 which is formed in the syringe connector 100 is air-tightly sealed, and a portion of the gas flow path L2 which is formed in the container connector 20 is air-tightly sealed.

Furthermore, when the syringe connector 100 is pulled upwardly by a predetermined distance, the holder protrusion 212 of the needle seal holder 210 engages with a step between the second hole section 192 and the third hole section 193 in the up-down direction. By this engagement, when the syringe connector 100 is pulled upwardly, the needle seal holder 210 and the needle seal 200 are moved downwardly in the outer shell main body 111, together with the head sleeve 180.

When the syringe connector 100 is pulled further upwardly by the predetermined distance after the needle seal holder 210 engages with the head sleeve 180, the needle 170 is pulled out of the container seal 70. The container seal liquid-tightly and air-tightly seals the hole formed by the needle 170, by the resilience.

Furthermore, when the needle 170 is pulled out of the container seal 70 and then the syringe connector 100 is further pulled upwardly by the predetermined distance, the second arm 232 is rotated by the unlocking protrusion 129 of the outer shell barrel section 117. Consequently, the second arm protrusion 240 of the second arm 232 moves outwardly from the locking recess 67 in the radial direction, and the second arm protrusion 240 and the locking recess 67 are disengaged. Specifically, the stopper sleeve 230 and the seal cap 60 are unlocked.

In this state, the portion of the needle 170 in which the hole 172 is formed is stored in the shaft section 202 of the needle seal 200, and the hole 172 is sealed with the needle seal 200. The needle seal 200 liquid-tightly and air-tightly seals the hole formed by the needle 170, by the resilience.

Thus, the needle 170 is pulled out of the container seal 70, and the liquid flow path L1 is accordingly divided. Furthermore, the needle 170 of a portion of the liquid flow path L1 which is formed in the syringe connector 100 is sealed, and the liquid flow path forming section L3 of a section of the liquid flow path L1 which is formed in the container connector 20 is sealed.

When the seal cap 60 and the head sleeve 180 are unlocked and then the syringe connector 100 is pulled further upwardly, the seal cap 60 moves downwardly relative to the first arm 231 of the stopper sleeve 230. When the seal cap 60 moves downwardly relative to the first arm 231, the first arm 231 urged by the outer peripheral surface of the seal cap 60 is released. When the first arm 231 urged by the outer peripheral surface of the seal cap 60 is released, the first arm is rotated by the elasticity (the resilience) of the coupling section 233. When the first arm 231 is rotated, as shown in FIG. 14, the upper end of the first arm is disposed below the locking protrusion 128. Specifically, the first arm 231 is in a state of being engageable with the locking protrusion 128.

When the first arm 231 is in the state of being engageable with the locking protrusion 128, the head sleeve 180 is prevented from being moved from a state where the second hole section 192 is sealed, i.e., the state where the needle 170 of the portion of the liquid flow path L1 which is formed in the syringe connector 100 is sealed and a section L5 of the gas flow path L2 which is formed in the syringe connector 100 is sealed. Note that the section L5 includes a gap between the second hole section 192 of the head sleeve 180 and the needle seal 200, a gap between the second hole section 192 and the needle seal holder 210, a gap between the third hole section 193 and the needle seal holder 210, an interior of the fourth hole section 194, an upper end portion of an interior of the inner sleeve 140, and the connecting section 145.

In the connection equipment 10 having such a constitution, only by pushing the syringe connector 100 into the container connector 20 in one direction, the head sleeve 180 and the container connector 20 can be locked by the second arm 232 of the stopper sleeve 230 and the locking recess 67 of the seal cap 60 in the state where the liquid flow path L1 and the gas flow path L2 are formed in the syringe connector 100 and the container connector 20. Furthermore, the syringe connector 100 and the container connector 20 can be locked by the locking section 113 and the lower end of the seal cap base 61.

Specifically, the operation of connecting the syringe connector 100 to the container connector 20 and the locking operation of preventing the container connector 20 from being disconnected from the syringe connector 100 in the state where the liquid flow path L1 and the gas flow path L2 are formed can be achieved by one operation of pushing the syringe connector 100 into the container connector 20 in the one direction. Both the disconnecting and the unlocking can be achieved by one operation of similarly pressing the operating section 155 with the unlocking protrusion 129 of the outer shell barrel section 117 and pulling the syringe connector 100 out of the container connector 20 in the one direction.

Thus, the connection and locking of the syringe connector 100 to the container connector 20 can be achieved with one continuous operation, and the unlocking and disconnecting of the syringe connector 100 from the container connector 20 can be achieved with one continuous operation. Consequently, the operation of connecting and locking the syringe connector 100 to the container connector 20 and the unlocking and disconnecting operation can be facilitated.

Furthermore, the syringe connector 100 may only be pushed into the container connector 20 until the bottom is reached, and hence, the operation is easy. Furthermore, the operator does not have to take an operation amount of the syringe connector 100, i.e., a push-in amount of the syringe connector 100 into consideration, and hence, the operation is easy.

Additionally, the air bag 160 is provided in the syringe connector 100, so that running cost of use of the connection equipment 10 can be prevented from being increased. This respect will be specifically described. The chemical solution may be collected from a plurality of containers 5 to one syringe 6. When the container connector 20 is fixed to the container 5 and the chemical solution is collected, the container connector is discarded without being disconnected from the container 5. Consequently, during the use of the connection equipment 10, a number of the container connectors 20 to be discarded tends to increase relative to a number of the syringe connectors 100 to be discarded. Consequently, for a user, a number of the container connectors 20 to be purchased tends to increase relative to the syringe connectors 100.

However, when the air bag 160 is provided in the syringe connector 100 as in the present embodiment, cost of the container connector 20 can be decreased as much as the air bag 160. Consequently, the running cost of the use of the connection equipment 10 can be prevented from being increased.

Furthermore, the air bag 160 is stored in the air bag storage section 150 that is harder than the air bag 160, so that the air bag 160 made of a thin film can be prevented from being brought into contact with foreign matter and being torn. In this case, the transparent or translucent resin material is used in the air bag storage section 150, or the opening or the transparent window portion is provided in a part of the wall surface of the air bag storage section 150, so that the shape of the air bag 160 in the air bag storage section 150 may be seen. In this case, the operator can visually recognize that a pressure adjustment mechanism is working normally.

Furthermore, a state where the needle 170 that constitutes the liquid flow path and the section L5 that constitutes the gas flow path in the syringe connector 100 are sealed can be locked in a state where the container connector 20 is disconnected from the syringe connector 100, by the first arm 231 of the stopper sleeve 230 and the locking protrusion 128.

Consequently, it is possible to prevent the chemical solution from leaking out of the needle 170 that constitutes the liquid flow path and the section L5 that constitutes the gas flow path in the syringe connector 100, after the chemical solution is collected into the syringe 6 and the container connector 20 is disconnected from the syringe connector 100.

Furthermore, the first arm 231 and the locking protrusion 128 can be unlocked by an operation of pushing the syringe connector 100 into the container connector 20 with the conical surface 62a that is the outer peripheral surface of the seal cap 60 of the container connector 20.

Consequently, the unlocking operation of the first arm 231 and the locking protrusion 128, the connecting operation of the syringe connector 100 and the container connector 20 and the locking operation of the second arm 232 and the locking recess 67 can be achieved with a series of operations. Consequently, the operation of the connection equipment 10 can be facilitated.

Note that the gas flow path L2 may be provided with a gas-liquid separation filter to prevent intrusion of the chemical solution into the air bag 160. Furthermore, an urging member such as a spring that urges the head sleeve 180 to move downwardly may be provided between the outer shell 110 and the head sleeve 180. When the container connector 20 is disconnected from the syringe connector 100 by this urging member, the head sleeve 180 smoothly moves. Consequently, force in moving the syringe connector 100 can be decreased. Note that in the present embodiment, a cylinder is used as an example of the tubular shape. For example, the outer shell main body 111, the inner sleeve 140, the head sleeve 180, the seal cap 60 and the like are formed in the cylindrical shape. However, these shapes are not limited to the cylinder. Examples of the shape include a tubular shape in which a cross section orthogonal to an axis is rectangular and a tubular shape in which a cross section orthogonal to the axis is polygonal. Furthermore, in the present embodiment, the container cap main body 40 is formed in the columnar shape, but the present embodiment is not limited to this shape. The container cap main body may be formed, for example, in a pillar shape in which a cross section orthogonal to the axis is polygonal. Furthermore, the container seal 70 has the cylindrical shape in which the circumferential surface is formed in the bellows, but the present embodiment is not limited to this shape. A cross section of the container seal which is orthogonal to the axis may be formed, for example, in a rectangular shape in accordance with the shape of the container cap main body 40.

Next, connection equipment 10A according to a second embodiment of the present invention will be described with reference to FIG. 21 to FIG. 35. Note that a constitution having a function similar to the function of the first embodiment is denoted with the same reference signs as in the first embodiment and description is omitted.

Figure 21:
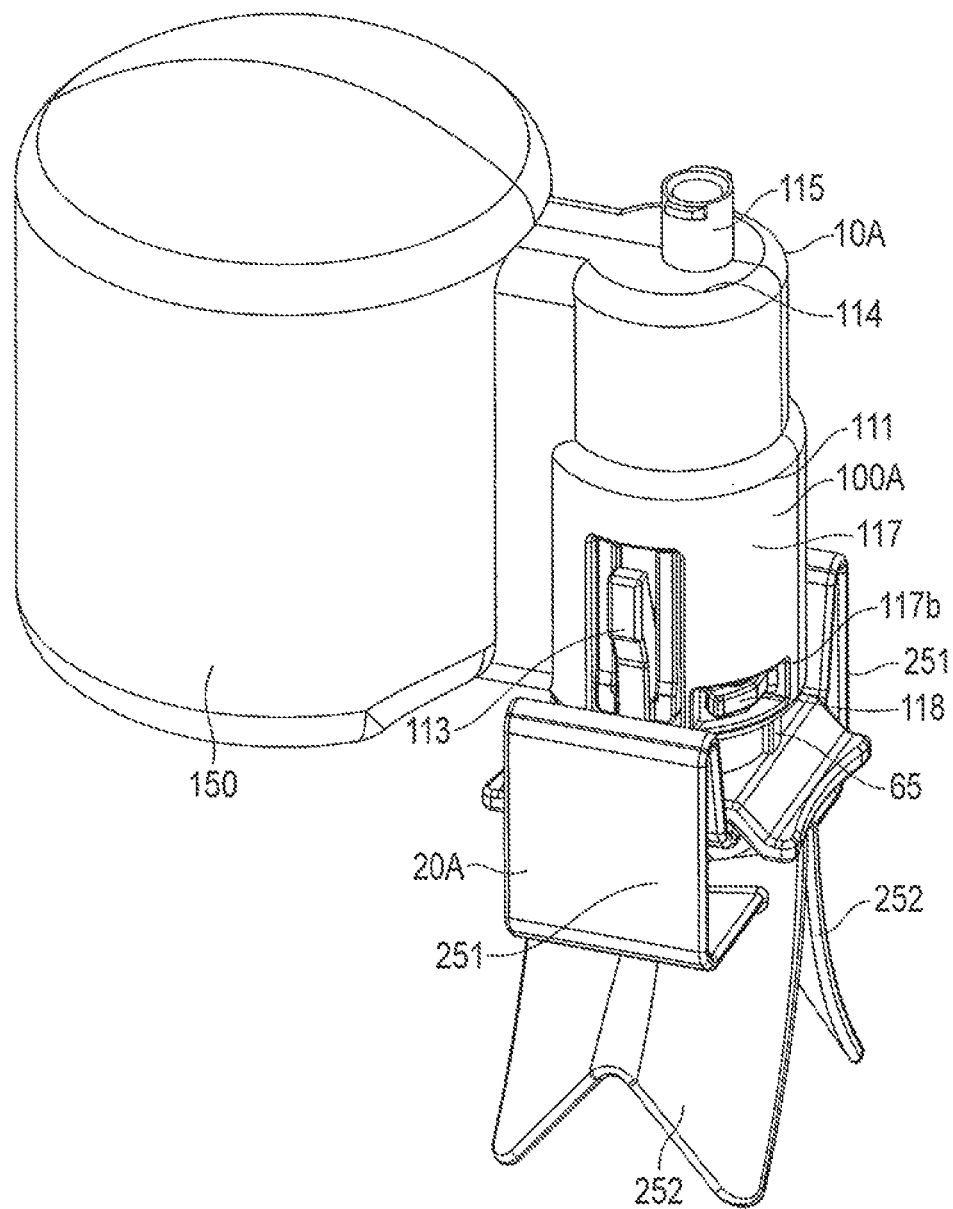
FIG. 21 is a perspective view showing a state where a container and a syringe are connected by connection equipment according to a second embodiment of the present invention.
Figure 22:
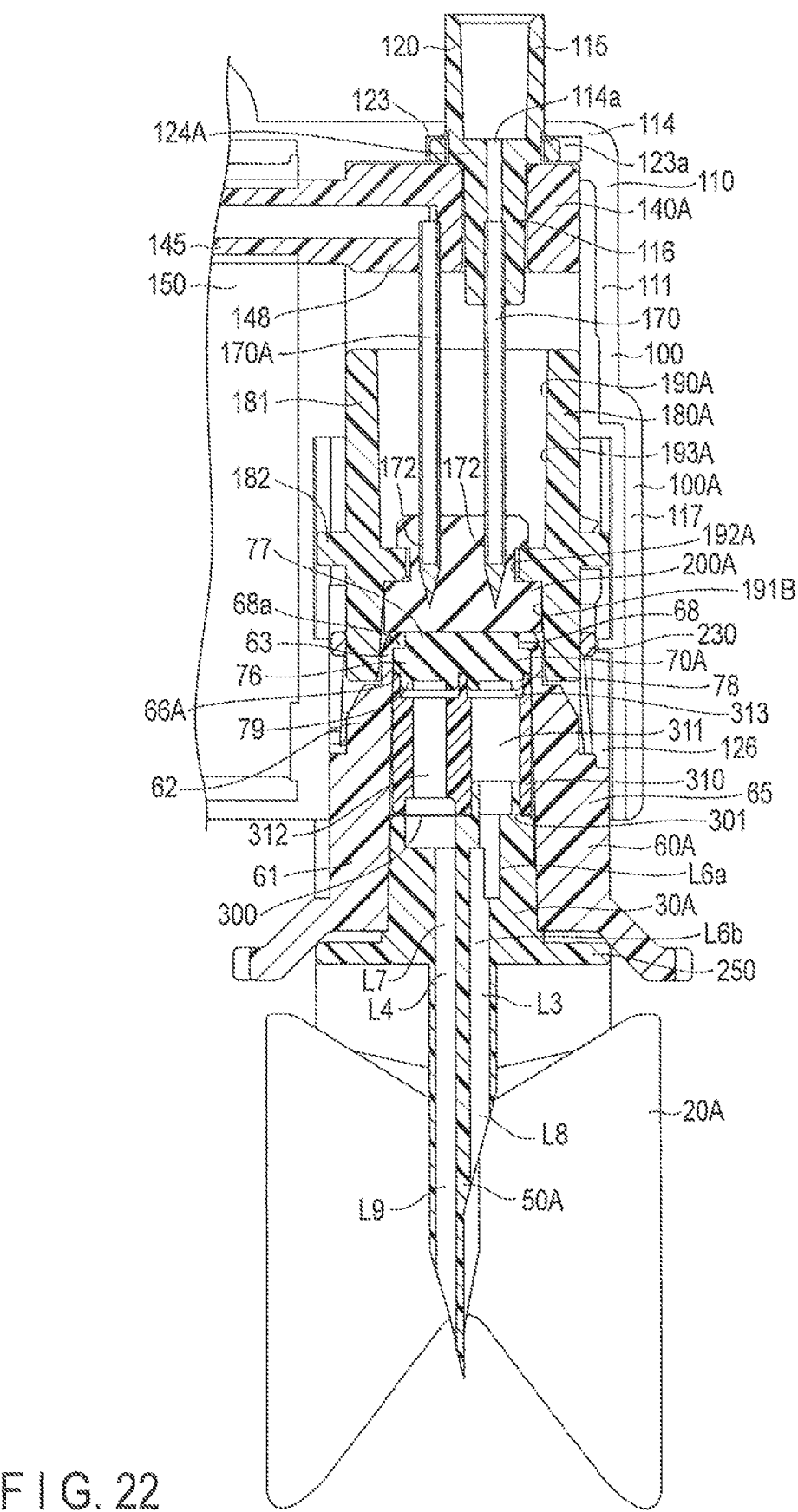
FIG. 22 is a cross-sectional view showing that a container connector for use in the connection equipment is in a state of being connected to a syringe connector for use in the connection equipment.
Figure 23:
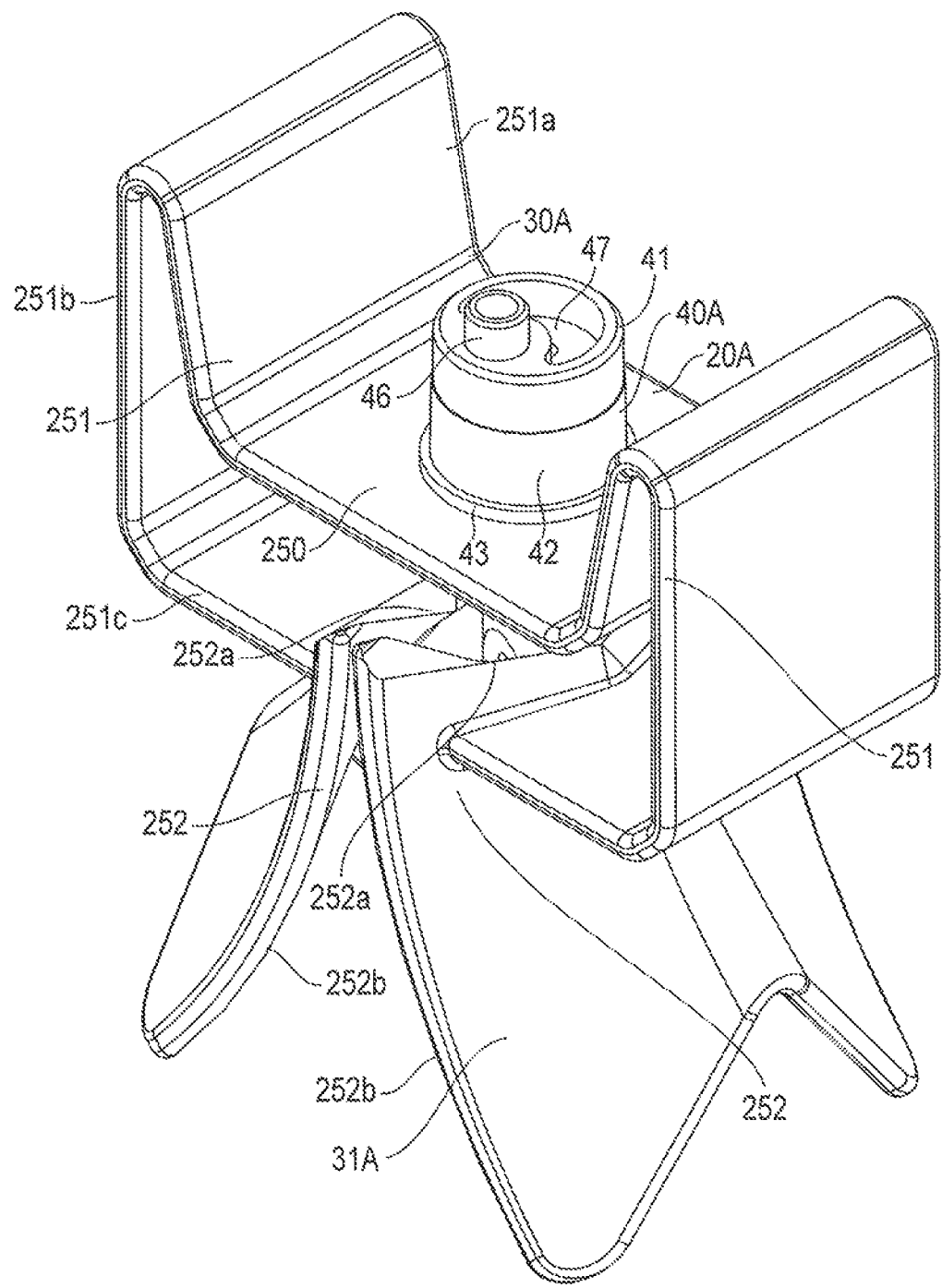
FIG. 23 is a perspective view showing a main part of the container connector.
Figure 24:
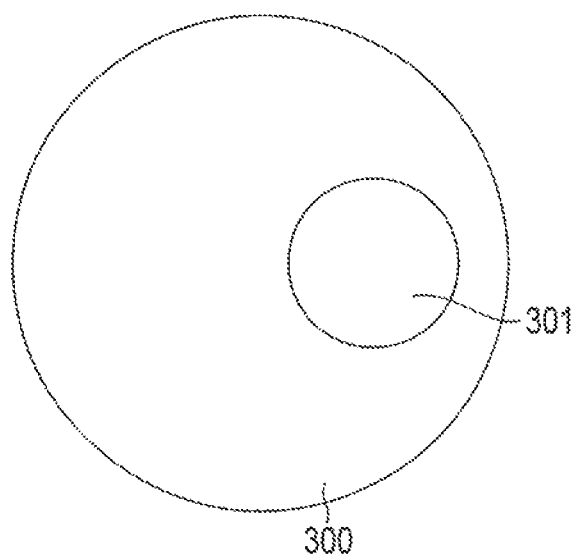
FIG. 24 is a plan view showing a hydrophobic filter for use in the container connector.

FIG. 21 is a perspective view showing a state where a container connector 20A and a syringe connector 100A for use in the connection equipment 10A are connected. Note that the connection equipment 10A shown in FIG. 21 has a state where a liquid flow path L1 and a gas flow path L2 are formed. When a container 5 and a syringe 6 are connected to the connection equipment 10A having the state shown in FIG. 21 in the same manner as in FIG. 1, the container 5 and the syringe 6 are connected by the connection equipment 10A. FIG. 22 is a cross-sectional view showing a state in the middle of an operation of connecting the container connector 20A and the syringe connector 100A for use in the connection equipment 10A. In FIG. 22, the liquid flow path L1 and the gas flow path L2 are not formed. FIG. 23 is a perspective view showing a main part of the container connector 20A. Specifically, FIG. 23 is the perspective view showing a container cap 30A for use in the container connector 20A. FIG. 24 is a plan view showing a hydrophobic filter 300 for use in the container connector 20A.

Figure 25:
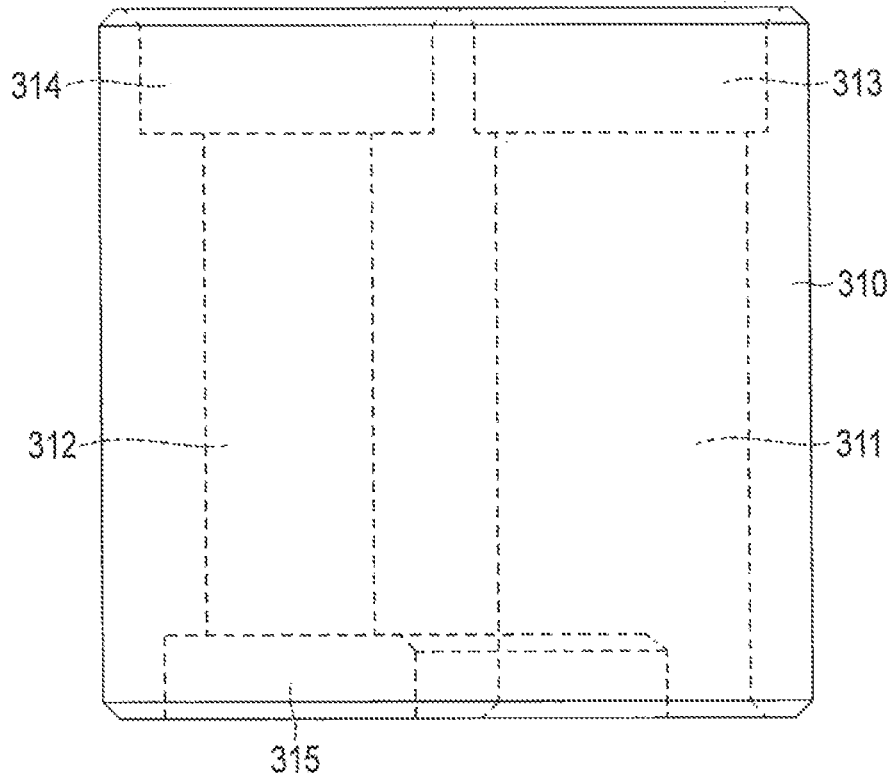
FIG. 25 is a front view showing a seal pin for use in the container connector.
Figure 26:
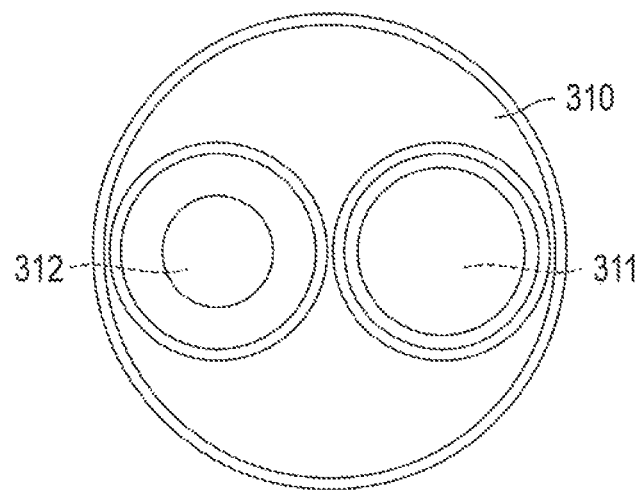
FIG. 26 is a plan view of the seal pin.
Figure 27:
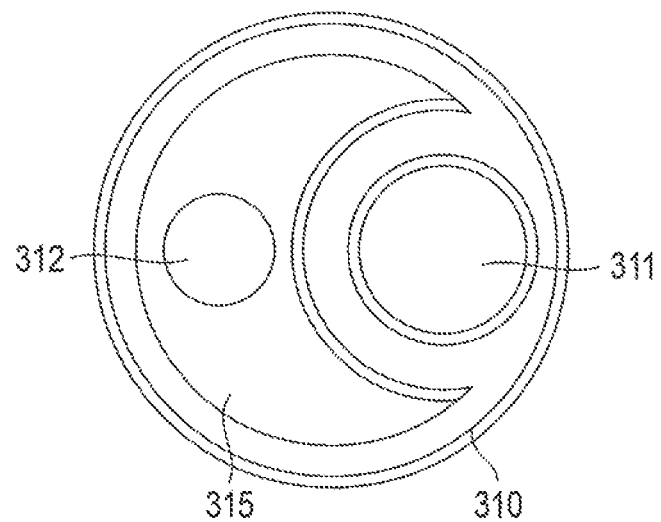
FIG. 27 is a bottom view of the seal pin.
Figure 28:
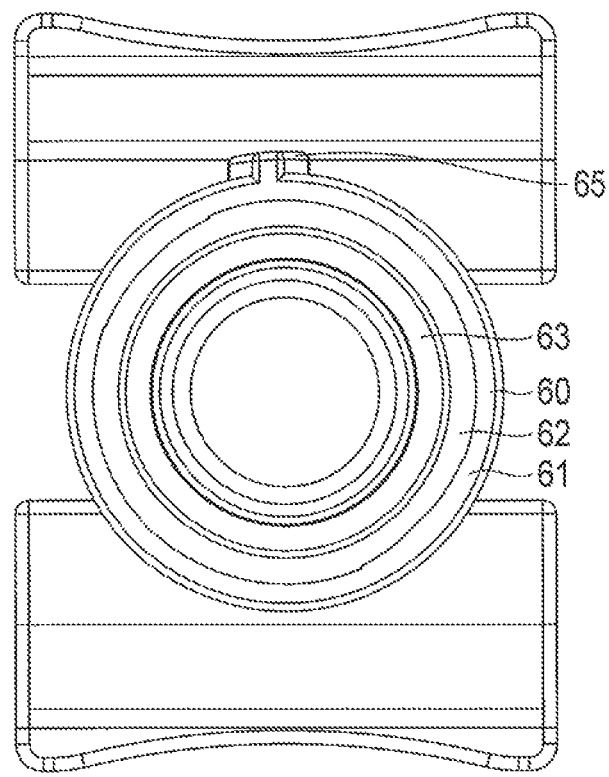
FIG. 28 is a plan view showing a seal cap for use in the container connector.
Figure 29:
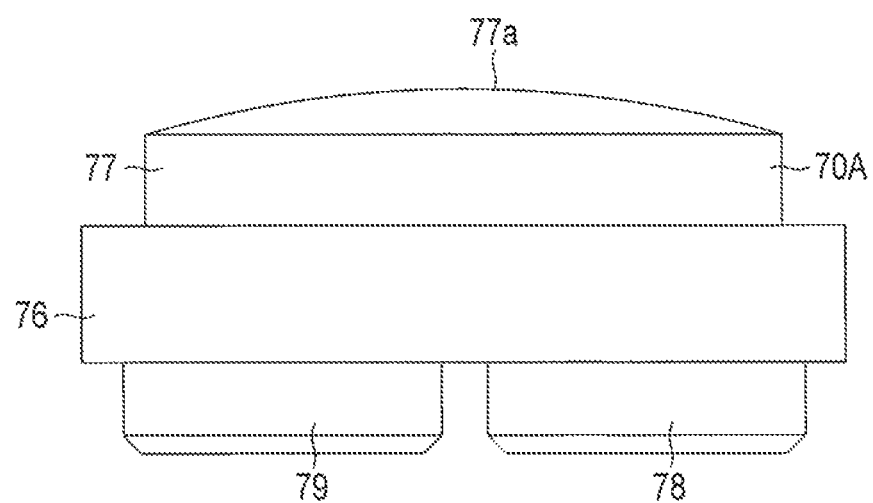
FIG. 29 is a side view showing a container seal for use in the container connector.
Figure 30:
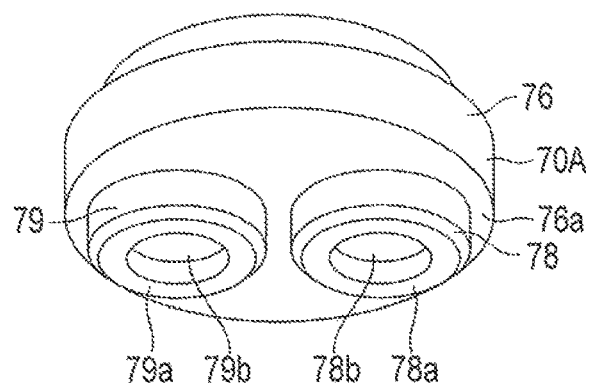
FIG. 30 is a perspective view showing the container seal.
Figure 31:
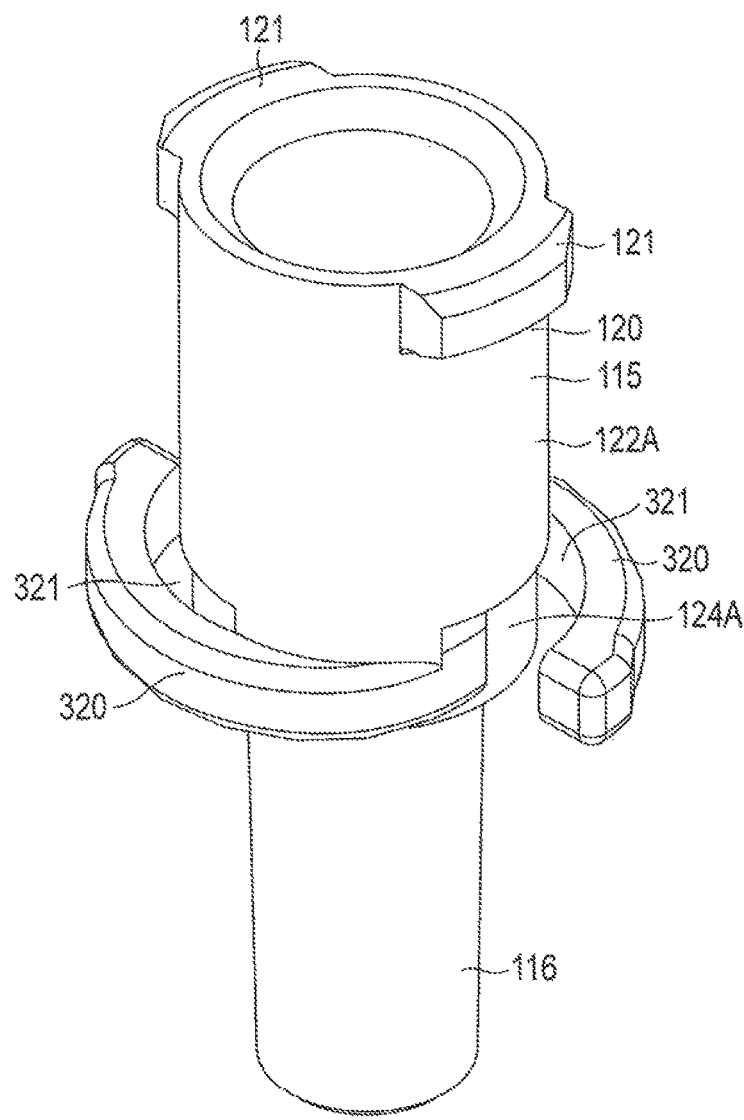
FIG. 31 is a perspective view showing a needle holder for use in the syringe connector.
Figure 32:
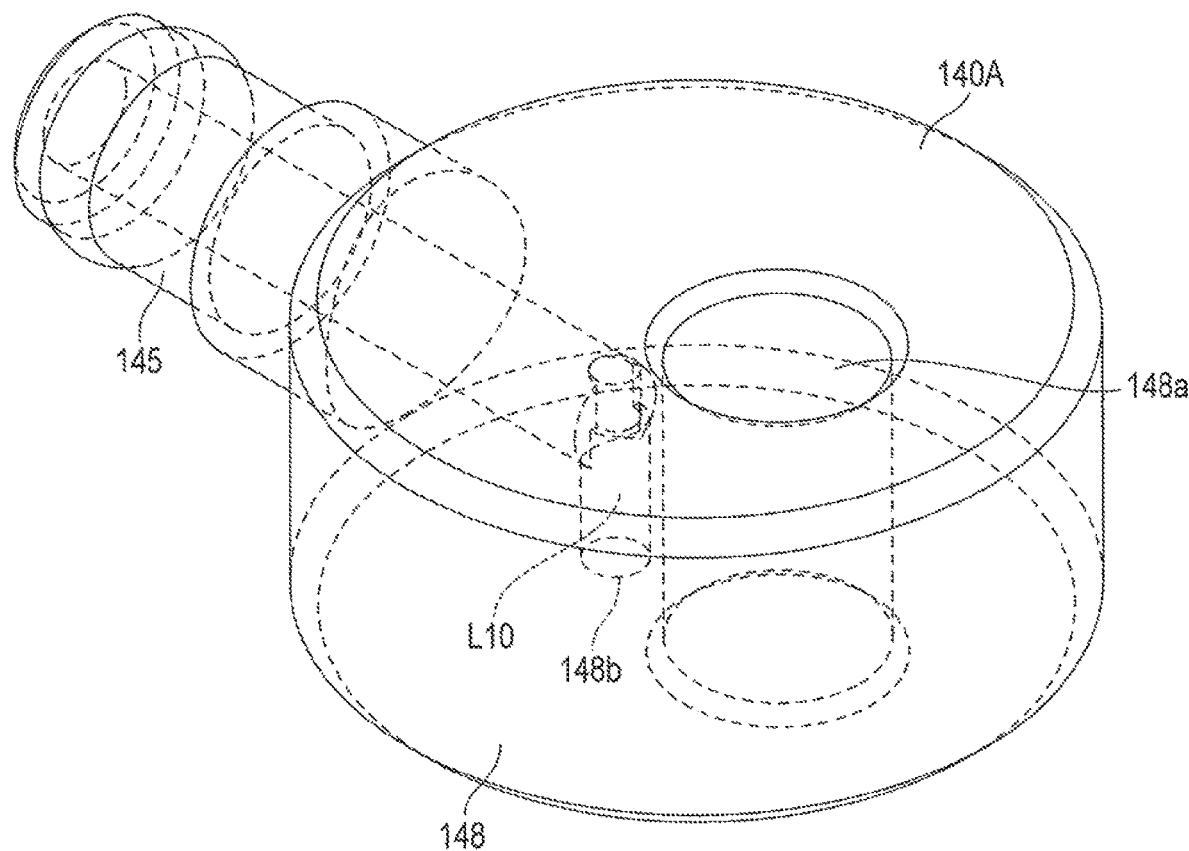
FIG. 32 is a perspective view showing an inner sleeve for use in the syringe connector 1.

FIG. 25 is a front view showing a seal pin 310 for use in the container connector 20A. FIG. 26 is a plan view of the seal pin 310. FIG. 27 is a bottom view of the seal pin 310. FIG. 28 is a plan view showing a seal cap 60A for use in the container connector 20A. FIG. 29 is a side view showing a container seal 70A for use in the container connector 20A. FIG. 30 is a perspective view showing the container seal 70A. FIG. 31 is a perspective view showing a needle holder 122A for use in the syringe connector 100A. FIG. 32 is a perspective view showing an inner sleeve 140A for use in the syringe connector 100A.

Figure 33:
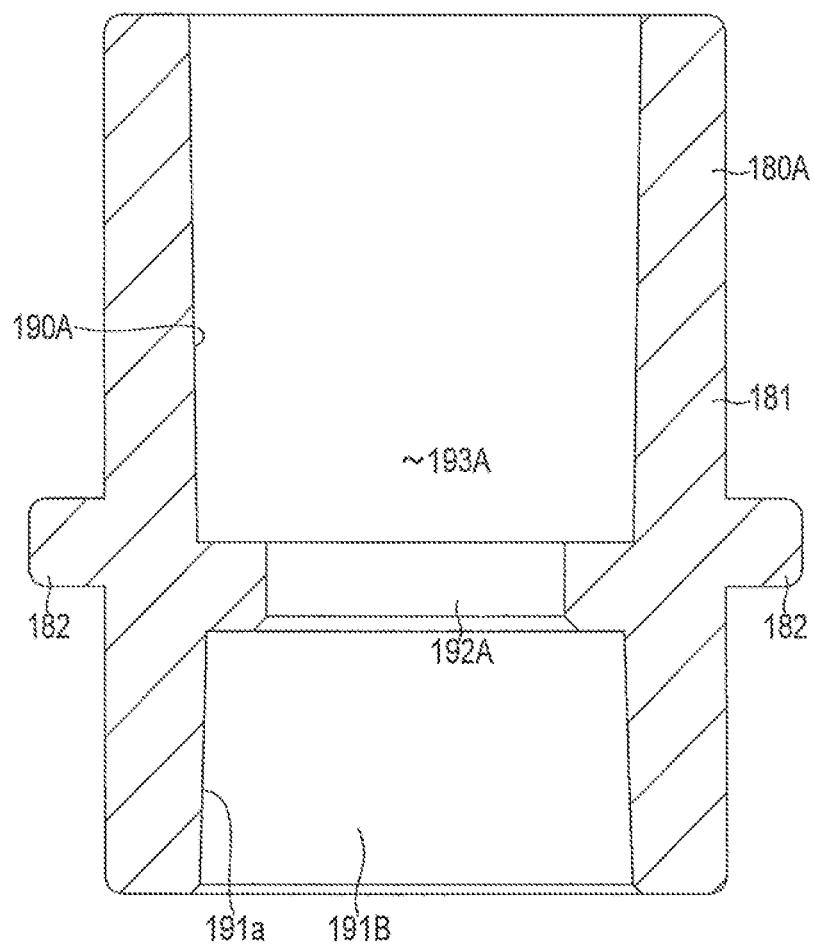
FIG. 33 is a cross-sectional view showing a head sleeve for use in the syringe connector.
Figure 34:
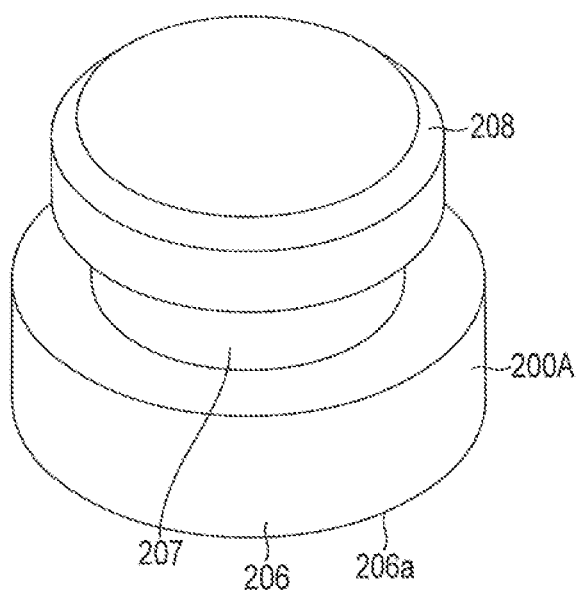
FIG. 34 is a perspective view showing a needle seal for use in the syringe connector.
Figure 35:
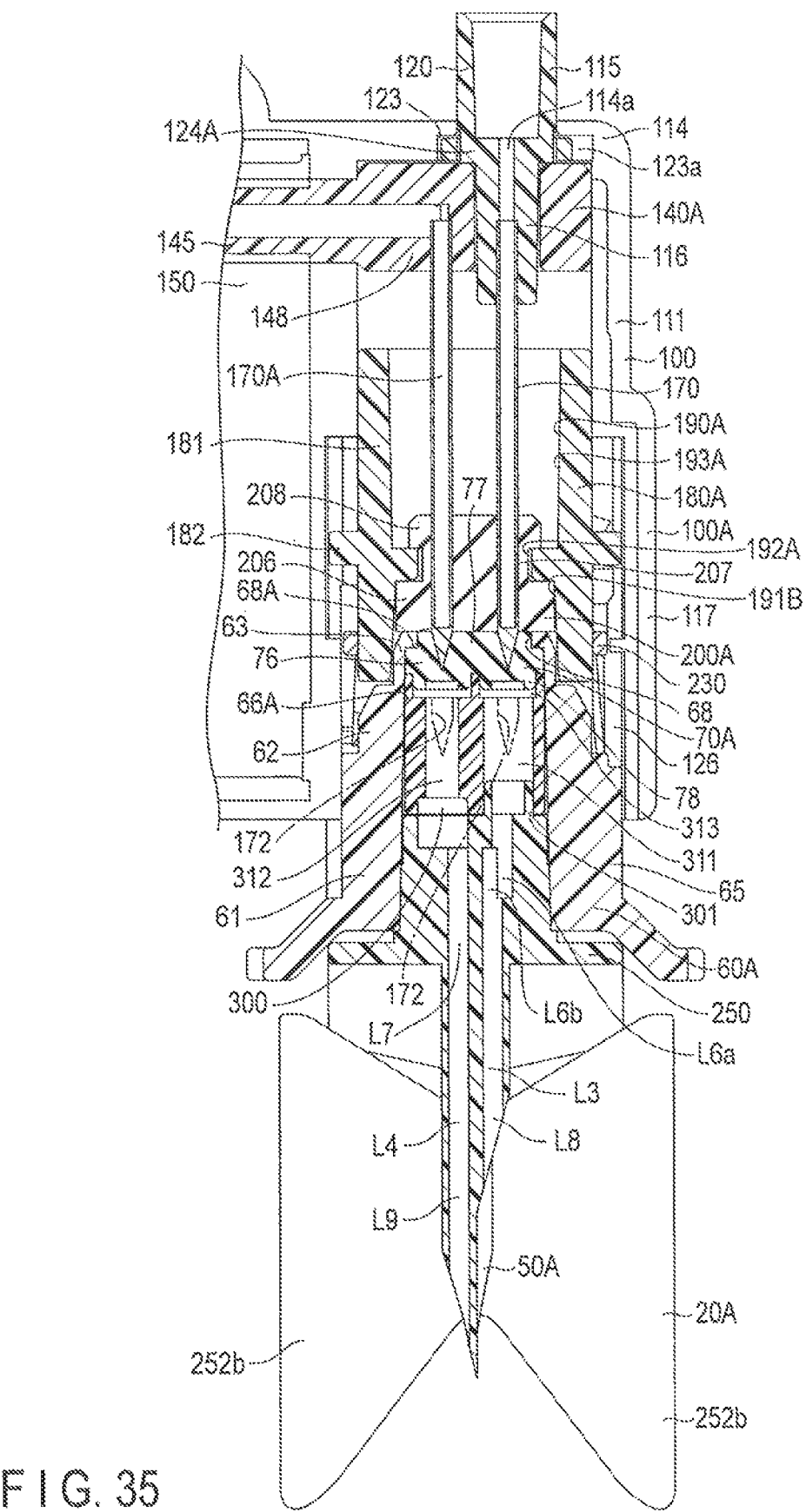
FIG. 35 is a cross-sectional view showing a state where a needle of the syringe connector and a gas needle intrude into the container seal of the container connector.

FIG. 33 is a cross-sectional view showing a head sleeve 180A for use in the syringe connector 100A. FIG. 34 is a perspective view showing a needle seal 200A for use in the syringe connector 100A. FIG. 35 is a cross-sectional view showing a state in the middle of an operation of connecting the syringe connector 100A and the container connector 20A. In FIG. 35, the liquid flow path L1 and the gas flow path L2 are not formed.

As shown in FIG. 21 and FIG. 22, the connection equipment 10A has the container connector 20A formed to be fixable to the container 5, and the syringe connector 100A formed to be fixable to a barrel 7 of the syringe 6 and removably fixed to the container connector 20A.

In the present embodiment, as an example, an up-down direction is set to the connection equipment 10A based on a state where the container 5 is disposed below and the syringe 6 is disposed above. Note that an axial direction of the after-mentioned container cap 30A of the container connector 20A and an axial direction of the seal cap 60A are parallel to the up-down direction, and an axial direction of an after-mentioned outer shell main body 111 of the syringe connector 100 is parallel to the up-down direction.

Firstly, description will be made as to the container connector 20A. As shown in FIG. 21 to FIG. 30, the container connector 20A has the container cap 30A formed to be fixable to the container 5, the hydrophobic filter 300 disposed on the container cap 30A, the seal pin 310 disposed on the hydrophobic filter 300, the seal cap 60A fixed to the container cap 30A, and the container seal 70A provided in the seal cap 60A.

The container cap 30A has a liquid flow path forming section L3 that constitutes a part of the liquid flow path L1 via which an interior of the container 5 communicates with an interior of the barrel 7 and through which a liquid (a chemical solution) can flow, and a gas flow path forming section L4 that constitutes a part of the gas flow path L2 via which the interior of the container 5 communicates with an interior of an air bag 160 that is a pressure adjustment section as described later and through which air can flow.

As shown in FIG. 22 and FIG. 23, the container cap 30A specifically has a container fixing section 31A formed to be fixable to the container 5, a container cap main body 40A, and a needle section 50A formed to be insertable into the container 5.

The container fixing section 31A is configured to be fixable to the container 5 in a state where the needle section 50A is inserted in a plug of a mouth of the container 5 and the liquid flow path forming section L3 and the gas flow path forming section L4 communicate with the interior of the container 5. By the container fixing section 31A, the container cap main body 40A is fixed to the container 5. For example, the container fixing section 31A is configured to be capable of holding the container 5 with two engagement sections 252 and thereby fixing the container. Specifically, the container fixing section 31A has a base 250 formed integrally with the container cap main body 40A, two arms 251 formed in the base 250, and the engagement sections 252 formed in the two arms 251, respectively, and formed to be engageable with the container 5.

The base 250 is provided in a lower end portion of the container cap main body 40A. The base 250 is formed in a plate shape having an area larger than an area of the container cap main body 40A, and extends relative to the container cap main body 40A in a direction orthogonal to an axial direction of the container cap main body 40A. For example, the container cap main body 40A is formed in the plate shape orthogonal to the axial direction of the container cap main body 40A. The container cap main body 40A is disposed in a center of the base 250.

The arms 251 are formed at both ends of the base 250, respectively. Each arm 251 has a first arm forming section 251a extending upwardly relative to the base 250, a second arm forming section 251b extending from an upper end of the first arm forming section 251a to be below the base 250, and a third arm forming section 251c extending from a lower end of the second arm forming section 251b to a needle section 50A side.

Each arm 251 is formed that the second arm forming section 251b, the third arm forming section 251c and an engagement section 252 are rotatable about a bent portion of a rotation center between the first arm forming section 251a and the second arm forming section 251b.

The engagement section 252 is formed at a tip of the third arm forming section 251c on a container cap main body 40A side. The engagement section 252 is formed in a shape extending along an axis of the container cap main body 40A. Specifically, a cross section of the engagement section 252 which is orthogonal to the axis of the container cap main body 40A is formed in a V-shape that is open on the needle section 50A side. Each engagement section 252 engages with the container 5 by holding, for example, a neck of the container 5 with an upper end portion 252a.

Furthermore, a surface 252b of the engagement section 252 on the container cap main body 40 side is formed as a guide surface that guides the container 5 to the upper end portion 252a. Furthermore, the surface 252b is inclined relative to the up-down direction so that a lower side comes away from the axis of the container cap main body 40A. A cross section of the engagement section 252 extending along a cut plane orthogonal to the axis of the container cap main body 40A is formed in a V-shape. Consequently, the surface 252b of one of the engagement sections 252 comes in contact with the container 5 at two points, and the surface 252b of the other engagement section 252 also comes in contact with the container 5 at two points. In consequence, the container 5 comes in contact with two engagement sections 252 at four points. Note that also in the first embodiment, the container fixing section 31A may be used in place of the container fixing section 31.

The container cap main body 40A is formed in a columnar shape having a plurality of diameters. The container cap main body 40A has a container cap small diameter section 41 that constitutes an upper section, a container cap intermediate diameter section 42 that constitutes a middle section in the up-down direction, and a container cap large diameter section 43 that constitutes a lower section. Note that in the present embodiment, the container cap small diameter section 41 has a diameter slightly smaller than a diameter of the container cap intermediate diameter section 42.

In an upper surface of the container cap main body 40A, a protrusion 46 that protrudes relative to another portion is integrally formed at a position shifted outwardly from the axis of the container cap main body 40A in a radial direction. The protrusion 46 is formed in a cylindrical shape so that an axis of the protrusion is parallel to the axis of the container cap main body 40A. In the container cap main body 40A, as shown in FIG. 22, a part L6 of the liquid flow path forming section L3 is formed. The part L6 communicates with an inner side of the protrusion 46. The part L6 of the liquid flow path forming section L3 extends to the lower end of the container cap main body 40A.

Note that in the present embodiment, the part L6 of the liquid flow path forming section L3 includes two portions shifted in a radial direction of the container cap main body 40A and arranged to communicate with a part L8 of the liquid flow path forming section L3 which is formed in the after-mentioned needle section 50A. A portion L6b of these two portions which is disposed below a portion L6a disposed above is disposed at a position shifted to an axial side of the container cap main body 40A. The portion L6a and the portion L6b partially communicate with the container cap main body 40A in the radial direction. Each of the portion L6a and the portion L6b is a hole having an axis parallel to the axis of the container cap main body 40A.

As shown in FIG. 23, in a portion other than the protrusion 46 in the upper surface of the container cap main body 40A, a recess 47 is formed. A part of the recess 47 is configured. The recess 47 is formed so that a flow path cross-sectional area is larger than a cross-sectional area of another region of the gas flow path L2. The recess 47 is formed in a shape dented from the other portion of the upper surface. In the present embodiment, the recess 47 is formed in a shape along an arc about the axis of the container cap main body 40A in planar view, specifically a crescent shape, and both ends of the recess in a circumferential direction extend to a vicinity of the protrusion 46. A cross-sectional area of the recess 47 is larger than a cross-sectional area of each side portion of the recess 47 in the gas flow path L2.

As shown in FIG. 22, a part L7 of the gas flow path forming section L4 is formed in the container cap main body 40A. The part L7 of the gas flow path forming section L4 extends from a bottom surface of the recess 47 to the lower end of the container cap main body 40A in parallel with the axis of the container cap main body 40A. The part L7 of the gas flow path forming section L4 is a hole having an axis parallel to the axis of the container cap main body 40A.

The needle section 50 extends downwardly from the base 250 in parallel with the axis of the container cap main body 40A. The needle section 50 is disposed, for example, coaxially with the container cap main body 40. In the needle section 50, a lower end, i.e., a leading end when being inserted into the container 5 is formed as a sharp head.

In the needle section 50A, the part L8 of the liquid flow path forming section L3 and a part L9 of the gas flow path forming section L4 are formed. The part L8 of the liquid flow path forming section L3 communicates with the part L6 of the liquid flow path forming section L3. The part L6 of the liquid flow path forming section L3 is open in a lower end surface of the needle section 50A. Each of the lower portion L6b of the part L6 of the liquid flow path forming section L3 and the part L9 is a hole, for example, having a cross-sectional shape that is constant in the axial direction.

Note that in the needle section 50A, a lower end of the part L8 of the liquid flow path forming section L3 is disposed above a lower end of the part L9 of the gas flow path forming section L4. Consequently, when the connection equipment 10A, the container 5 and the syringe 6 are tilted to dispose the container 5 above the connection equipment 10A, the chemical solution accumulated on a neck side of the container 5 can be guided to the part L8 of the liquid flow path forming section L3.

The part L9 of the gas flow path forming section L4 communicates with the part L7 of the gas flow path forming section, and is open in the lower end of the needle section 50A. Each of the parts L7 and L9 of the gas flow path forming section L4 is, for example, a hole having a cross-sectional shape that extends from the bottom surface of the recess 47 to the lower end of the needle section 50A and that is constant in the axial direction.

The hydrophobic filter 300 is disposed on the upper surface of the container cap main body 40A. The hydrophobic filter 300 is made of a material having properties of being impermeable to a liquid and being permeable to a gas. The hydrophobic filter 300 is made of, for example, Teflon (registered trademark). Since the hydrophobic filter 300 has such properties, the filter is impermeable to the chemical solution and permeable to air.

As shown in FIG. 24, the hydrophobic filter 300 is formed in a thin disk shape having the same outer diameter as in the container cap main body 40A. The hydrophobic filter 300 has a hole 301 in which the protrusion 46 is disposed in a state where the filter is disposed in the upper surface of the container cap main body 40A coaxially with the upper surface. The hole 301 has a diameter equal to or slightly larger than a diameter of the protrusion 46. When the protrusion 46 is disposed in the hole 301 and the hydrophobic filter 300 is disposed coaxially with the container cap main body 40A, an upper end opening of the recess 47 is closed with the filter.

The hydrophobic filter 300 is held between the container cap main body 40A and the seal pin 310 and is thereby fixed. Note that the hydrophobic filter 300 may be fixed to the upper surface of the container cap main body 40A by welding.

As shown in FIG. 22, the seal pin 310 is disposed on the hydrophobic filter 300. The seal pin 310 is formed in a columnar shape having the same diameter as in the container cap main body 40A. The seal pin 310 has a hole 311 in which the protrusion 46 can be disposed, and a hole 312 disposed opposite to the recess 47 via the hydrophobic filter 300.

The hole 311 has a size that fits with the protrusion 46. As shown in FIG. 25 and FIG. 26, an upper section 313 of the hole 311 has a slightly enlarged diameter, and is formed so that a part of the container seal 70A can be disposed. As shown in FIG. 25 and FIG. 27, a lower section 315 of the hole 312 is formed in the same shape as in the recess 47. Specifically, the lower section 315 of the hole 312 is formed in a shape along an arc. An edge of the lower section 315 of the hole 312 is superimposed on an edge of the recess 47 via the hydrophobic filter 300 in the axial direction of the container cap main body 40A, in a state where the seal pin 310 is disposed on the hydrophobic filter 300 as shown in FIG. 22.

An upper section 314 of the hole 312 is formed as a hole having, for example, a round cross section so that a part of the container seal 70A can be disposed in the upper section.

A middle section of the hole 312 is formed as a hole having, for example, a diameter smaller than a diameter of the upper section 314.

As shown in FIG. 22, the seal cap 60A is formed in a tubular shape in which the container cap main body 40A, the hydrophobic filter 300, the seal pin 310 and the container seal 70A are stored. The seal cap is fixed to the container cap main body 40 at a position where a lower end of the cap abuts on the container cap large diameter section 43. Furthermore, the seal cap 60A is formed so that an after-mentioned outer shell 110 of the syringe connector 100A and a stopper sleeve 230 can be unlocked and so that the cap can be locked with the stopper sleeve 230.

Specifically, the seal cap 60A is formed in a cylindrical shape having a plurality of outer diameters. A seal that can prevent the gas from leaking from the lower end of the seal cap 60A is formed between an inner peripheral surface 66A of the seal cap 60A and an outer peripheral surface of the container cap main body 40A.

In the present embodiment, the seal cap 60A is formed in a cylindrical shape in which the container cap intermediate diameter section 42 fits. When the container cap intermediate diameter section 42 fits in the seal cap 60A, sealing is achieved. Note that the sealing is not limited to the above sealing. As another example, an O-ring may be provided as a seal.

The seal cap 60A has a cylindrical seal cap base 61, a seal cap intermediate diameter section 62 formed on the seal cap base 61, and a seal cap small diameter section 63 formed on the seal cap intermediate diameter section 62.

In an outer peripheral surface of the seal cap base 61, as shown in FIG. 21, there is formed a first guiding protrusion 65 that guides movement of the container connector 20A in the up-down direction in the outer shell 110 of the syringe connector 100A. One first guiding protrusion 65 is formed in the present embodiment.

The seal cap small diameter section 63 is formed to have a diameter smaller than a diameter of an upper end of the seal cap intermediate diameter section 62. The seal cap small diameter section 63 is formed in a cylindrical shape that can fit in the after-mentioned head sleeve 180A of the syringe connector 100A.

An opening 68 of the seal cap small diameter section 63 is formed in a round shape having a diameter smaller than a diameter of the seal pin 310. That is, in the inner peripheral surface 66A of the seal cap 60A, a region to a lower end from a vicinity of an upper end portion has such a diameter that a seal between the region and an outer peripheral surface of the container cap intermediate diameter section 42 can be formed by fitting, and a region from the vicinity of the upper end to the upper end is formed to have a smaller diameter. An edge 68a of the opening 68 is configured so that the container seal 70A can be held between the edge and the seal pin 310.

The container seal 70A is disposed between the seal pin 310 and the edge 68a of the seal cap 60A. The container seal 70A is made of a resin such as a rubber or an elastomer and has flexibility. The container seal is formed so that a hole which is formed by inserting an after-mentioned needle 170 and a gas needle 170A of the syringe connector 100A can be liquid-tightly and air-tightly closed by resilience after the needle 170 and the gas needle 170A move.

The container seal 70A has a seal large diameter section that can fit in the seal cap 60A, and a seal small diameter section 77 formed in an upper surface of the seal large diameter section 76 to fit in the opening 68.

As shown in FIG. 29 and FIG. 30, the seal large diameter section 76 is formed so that a gap between the section and the inner peripheral surface 66A of the seal cap 60A can be air-tightly and liquid-tightly sealed. Specifically, the seal large diameter section 76 is formed in a columnar shape having an outer diameter slightly larger than an inner diameter of the seal cap 60A.

The seal large diameter section 76 is formed to come in contact with the edge 68a of the opening 68 of the seal cap 60A, so that a gap between the seal large diameter section 76 and the edge 68a can be air-tightly and liquid-tightly sealed. Specifically, the seal large diameter section 76 is formed to be slightly longer than a length from the seal pin 310 to the edge 68a in the axial direction.

As shown in FIG. 22, the seal large diameter section 76 has, in a lower end surface, a first fitting section 78 that fits in the upper section 313 of the hole 311 of the seal pin 310, and a second fitting section 79 that fits in the upper section 314 of the hole 312 of the seal pin 310.

As shown in FIG. 29 and FIG. 30, the first fitting section 78 is formed so that a gap between the section and an inner peripheral surface of the upper section 313 of the hole 311 can be liquid-tightly and air-tightly sealed. Specifically, the first fitting section 78 is formed in a columnar shape having an outer diameter slightly larger than an inner diameter of the upper section 313 of the hole 311. A round dent 78b is formed in a lower end surface 78a of the first fitting section 78.

The second fitting section 79 is formed so that a gap between the section and an inner peripheral surface of the upper section 314 of the hole 312 can be air-tightly and liquid-tightly sealed. Specifically, the second fitting section 79 is formed in a columnar shape having an outer diameter slightly larger than an inner diameter of the upper section 314 of the hole 312. A round dent 79b is formed in a lower end surface 79a of the second fitting section 79.

Furthermore, a length of the first fitting section 78 in the axial direction is shorter than a length of the upper section 313 of the hole 311 in the axial direction. A length of the second fitting section 79 in the axial direction is shorter than a length of the upper section 314 of the hole 312 in the axial direction. Consequently, as shown in FIG. 22, the first fitting section 78 and the second fitting section 79 can be inserted into the holes 311 and 312 until the seal large diameter section 76 comes in contact with an upper end of the seal pin 310. A lower end surface 76a of the seal large diameter section 76 comes in contact with an edge of the hole 311, to air-tightly and liquid-tightly seal a gap between the lower end surface 76a of the seal large diameter section 76 and the edge of the hole 311. The lower end surface 76a of the seal large diameter section 76 comes in contact with an edge of the hole 312, to air-tightly and liquid-tightly seal a gap between the lower end surface 76a and the edge of the hole 312.

The seal small diameter section 77 is formed so that a gap between the section and an inner peripheral surface of the opening 68 can be air-tightly and liquid-tightly sealed. Specifically, the seal small diameter section 77 is formed in a columnar shape having an outer diameter slightly larger than an inner diameter of the opening 68. As shown in FIG. 29, an upper end surface 77a of the seal small diameter section 77 is formed as a curved surface that protrudes upwardly.

Next, description will be made as to the syringe connector 100A. As shown in FIG. 22, the syringe connector 100A has the outer shell 110, the air bag 160, the needle 170, the gas needle 170A fixed in the outer shell 110, the tubular head sleeve 180A that is stored movably in the outer shell 110 while storing therein a part of the needle 170, the needle seal 200A fixed to the head sleeve 180A, and the stopper sleeve 230 formed so that the head sleeve 180A can be selectively fixed to the outer shell 110 and so that the head sleeve 180A can be selectively fixed to the container connector 20A.

The outer shell 110 has the outer shell main body 111, an air bag storage section 150, and a locking section 113 that can removably lock the outer shell main body 111 to the container connector 20A.

The outer shell main body 111 has an outer shell ceiling wall 114, a syringe fixing section 115, a needle fixing section 116, an outer shell barrel section 117, and the inner sleeve 140A fixed in the outer shell main body 111.

The outer shell ceiling wall 114 is formed, for example, in a disk shape. A hole 114a is formed at a position shifted outwardly from a center of the outer shell ceiling wall 114 in the radial direction. Specifically, the hole 114a is disposed at a position shifted from the center of the outer shell ceiling wall 114 to a side opposite to the air bag storage section 150. The needle fixing section 116 that protrudes downwardly from another region is formed in a lower surface of the outer shell ceiling wall 114. The needle fixing section 116 is formed in a columnar shape.

The syringe fixing section 115 communicates with the hole 114a of the outer shell ceiling wall 114. As shown in FIG. 22 and FIG. 31, the syringe fixing section 115 has a syringe fixing section main body 120 and a syringe fixing section protrusion 121. In the present embodiment, the syringe fixing section main body 120 is disposed coaxially with the hole 114a. For example, a plurality of syringe fixing section protrusions 121 are formed. The needle fixing section 116 communicates with the hole 114a.

In the present embodiment, the syringe fixing section 115, a part of the outer shell ceiling wall 114 and the needle fixing section 116 are formed by the needle holder 122A that is a member separate from the other section of the outer shell main body 111. In other words, the needle holder 122A is attached to the outer shell main body 111, thereby constituting the outer shell ceiling wall 114, the syringe fixing section 115 and the needle fixing section 116.

Specifically, a hole 123 that can store a part of the needle holder 122A is formed in the outer shell ceiling wall 114. An inner peripheral surface of the hole 123 has two inner diameters in an axial direction thereof. A lower section of the hole 123 is formed to have a larger diameter.

The needle holder 122A has a base 124A, the syringe fixing section 115, and the needle fixing section 116. The base 124A is formed to have a diameter larger than a diameter of the needle fixing section 116 and smaller than a diameter of the syringe fixing section 115. The base 124A is stored in the hole 123. The base 124A is supported by an upper end of the inner sleeve 140A, and is accordingly held in the hole 123 rotatably about a rotation center line parallel to an axial direction of the hole 123.

As shown in FIG. 31, in the base 124A, an arm 320 is formed to constitute a part of a ratchet that allows the needle holder 122A to rotate about an axis of the syringe fixing section 115 only in one direction and can regulate rotation of the holder in an opposite direction. A rotating direction of the needle holder 122A allowed by a ratchet mechanism is a direction in which the syringe 6 is rotated relative to the syringe fixing section 115 to remove the syringe 6 from the syringe fixing section 115.

For example, a plurality of arms 320 are formed, and specifically, two arms are formed. The arm 320 is formed in an arc shape, and one end of the arm is fixed to an outer peripheral surface of the base 124A. In other words, the arm 320 protrudes outwardly from the outer peripheral surface of the base 124A in the radial direction. The arm 320 has a gap 321 between the arm and an outer surface of the base 124A in a radial direction of the base 124A. Through the gap 321, the arm 320 can be bent in the radial direction of the base 124A.

As shown in FIG. 22, in the inner peripheral surface of the hole 123, there is formed a convex section 123a that abuts on the other end of the arm 320 in a direction in which the syringe 6 rotates relative to the syringe fixing section 115 to fix the syringe 6 to the syringe fixing section 115. A surface of the convex section 123a on an axial side of the hole 123 is formed as a curved surface that is continuous with the inner peripheral surface of the hole 123, to allow rotation of the arm 320 along the direction in which the syringe 6 rotates relative to the syringe fixing section 115 to remove the syringe 6 from the syringe fixing section 115.

Through a first guide groove 126, the container connector 20A is positioned at a position where the needle 170 is aligned with the hole 311 in a movement direction of the head sleeve 180A in the outer shell 110 and where the gas needle 170A is aligned with the hole 312 in the movement direction of the head sleeve 180A in the outer shell 110.

Specifically, when the first guiding protrusion 65 is stored in the first guide groove 126, the needle 170 is aligned with the hole 311 in the movement direction of the head sleeve 180A in the outer shell 110, and the gas needle 170A is aligned with the hole 312 in the movement direction of the head sleeve 180A in the outer shell 110.

Furthermore, in the present embodiment, an urging section 118 is formed in the outer shell barrel section 117 of the outer shell main body 111. The urging section 118 is configured to press the second arm 232 of the stopper sleeve 230 engaged in the locking recess 67 of the seal cap 60A in an engagement direction in the locking recess 67. Specifically, the urging section 118 is configured to urge the second arm 232, so that the engagement of the second arm 232 in the locking recess 67 can be strengthened.

Specifically, the urging section 118 is provided at an edge of a hole 117b formed at a position opposite to the second arm 232 of the stopper sleeve 230 disposed at its lower end, in the outer shell barrel section 117.

The inner sleeve 140A is fixed in the upper end portion of the outer shell main body 111, to constitute a part of the gas flow path L2. Specifically, as shown in FIG. 32, the inner sleeve 140A has an inner sleeve main body 148 that fits in the outer shell main body 111, and a connecting section 145.

The inner sleeve main body 148 is formed in a columnar shape that fits in the outer shell main body 111. In the inner sleeve main body 148, a hole 148a is formed in which the needle fixing section 116 is rotatably disposed.

In the inner sleeve main body 148, a part L10 of the gas flow path L2 is formed. The part L10 of the gas flow path L2 communicates with an interior of the connecting section 145. Furthermore, in the inner sleeve main body 148, a gas needle fixing section 148b is formed to which the gas needle 170A can be fixed. The gas needle fixing section 148b is a hole in which the gas needle 170A is fitted and fixed. The gas needle fixing section 148b communicates with the part L10 of the gas flow path L2.

The connecting section 145 is formed integrally with the inner sleeve main body 148.

The inner sleeve 140A formed in this way is fitted and fixed in the outer shell 110, in a state where an upper surface of the inner sleeve main body 148 is in surface contact with the lower surface of the outer shell ceiling wall 114, a part of the needle fixing section 116 is stored in the hole 148a and a part of the connecting section 145 is stored in a communication hole 125 of the outer shell barrel section 117. Note that inner sleeve 140A may be fixed to the outer shell 110, for example, with an adhesive.

The gas needle 170A is configured so that the gas can flow. The gas needle 170A has a constitution similar to the needle 170. The constitution of the gas needle 170A having a function similar to the function of the needle 170 is denoted with the same reference signs as in the needle 170 and description is omitted. An end portion of the gas needle 170A is fixed to the gas needle fixing section 148b of the inner sleeve 140A.

A position of a hole 172 of the gas needle 170A in the up-down direction is the same as a position of a hole 172 of the needle 170 in the up-down direction. Furthermore, in the present embodiment, a position of a lower end of the gas needle 170A in the up-down direction is the same as a position of a lower end of the needle 170 in the up-down direction. Consequently, as described later, with the movement of the head sleeve 180 in the outer shell 110, the gas needle 170A pierces the needle seal 200A at the same timing as in the needle 170. Additionally, the hole 172 of the gas needle 170A intrudes into the container seal 70A at the same timing as in the needle 170.

Each of the needle 170 and the gas needle 170A has such a length that the lower end is disposed in the needle seal 200A in a state where the head sleeve 180A is disposed at a lower end of a movement range in the outer shell main body 111. That is, the holes 172 are disposed in the needle seal 200A, and the each of the needle 170 and the gas needle 170A has a length to be sealed with the needle seal 200A.

Furthermore, the needle 170 has such a length that the hole 172 is disposed in the hole 311 of the seal pin 310 in a state where the head sleeve 180A is disposed at an upper end of the movement range in the outer shell main body 111. The gas needle 170A has such a length that the hole 172 is disposed in the hole 312 of the seal pin 310 in the state where the head sleeve 180A is disposed at the upper end of the movement range in the outer shell main body 111.

The head sleeve 180A is formed in a tubular shape that can move in the outer shell main body 111. The head sleeve 180A has a head sleeve main body 181 and a second guiding protrusion 182. In the present embodiment, the head sleeve main body 181 is formed in a cylindrical shape that movably fits in an inner peripheral surface of the outer shell barrel section 117.

A hole 190A in the head sleeve main body 181 is formed as a hole having a plurality of inner diameters. As shown in FIG. 33, the hole 190A has a first hole section 191B formed in a lower section of the hole 190A and including a lower end opening thereof, a second hole section 192A formed above the first hole section 191B, and a third hole section 193A formed above the second hole section 192 and including an upper end opening of the hole 190A. The first hole section 191B communicates with the second hole section 192A. The second hole section 192A communicates with the third hole section 193A. The hole sections 191B, 192A and 193A are coaxially arranged.

The first hole section 191B is formed so that the seal cap small diameter section 63 of the seal cap 60A can be disposed in the first hole section. In the present embodiment, as an example, the first hole section 191B is formed so that the seal cap small diameter section 63 can fit in the first hole section. An inner peripheral surface 191a of the first hole section 191B is formed to have a round cross section orthogonal to the axial direction. The first hole section 191B has a diameter that gradually increases toward its lower end. In other words, the inner peripheral surface 191a of the first hole section 191B is formed as a conical surface. The second hole section 192A is formed to have a diameter smaller than the diameter of the first hole section 191B. The third hole section 193A is formed to have a diameter larger than the diameter of the second hole section 192A.

As shown in FIG. 22, the needle seal 200A is fixed in the hole 190A. The needle seal 200A is made of a resin such as a rubber or an elastomer, and formed so that a hole formed by the needle 170 and the gas needle 170A can be liquid-tightly and air-tightly sealed by the resilience after the needle 170 and the gas needle 170A move.

Specifically, as shown in FIG. 34, the needle seal 200A has a needle seal large diameter section 206 disposed in the first hole section 191B, a needle seal small diameter section 207 formed integrally with the needle seal large diameter section 206 and disposed in the second hole section 192A, and a needle seal intermediate diameter section 208 formed integrally with the needle seal small diameter section 207 and disposed in the third hole section 193A.

The needle seal large diameter section 206 is formed in a columnar shape having a diameter larger than an inner diameter of the second hole section 192A. Specifically, the needle seal large diameter section 206 is formed in the columnar shape having an outer diameter slightly larger than an inner diameter of an upper end of the first hole section 191B. A lower end surface 206a of the needle seal large diameter section 206 is formed as a flat surface orthogonal to an axis of the needle seal large diameter section 206.

The needle seal small diameter section 207 is disposed coaxially with the needle seal large diameter section 206. The needle seal small diameter section 207 is formed in a columnar shape having an outer diameter smaller than the inner diameter of the second hole section 192A. The needle seal intermediate diameter section 208 is disposed coaxially with the needle seal small diameter section 207. The needle seal intermediate diameter section 208 is formed in a columnar shape having a diameter larger than the inner diameter of the second hole section 192A and smaller than an inner diameter of the third hole section 193A.

Note that sections of the container connector 20A that are not described are the same as in the container connector of the first embodiment. Furthermore, sections of the syringe connector 100A that are not described are the same as in the syringe connector 100 of the first embodiment.

Next, an operation of connecting the container 5 to the container connector 20A will be described. When the container 5 is connected to the container connector 20A, an operator disposes the container 5 between the surfaces 252b of two engagement sections 252 of the container fixing section 31A, and brings an upper end of the container 5 into contact with two surfaces 252b. At this time, the upper end of the container 5 is brought into contact with the two surfaces 252b at four points. When the two surfaces 252b are brought into contact with the container 5, the operator pushes the container connector 20A downwardly relative to the container 5.

When the container connector 20A is pushed downwardly, the container 5 is guided to an upper end portion 252a side of the engagement section 252 by the surface 252b. At this time, two engagement sections 252 are pressed apart from each other along the direction orthogonal to the axis of the container cap main body 40A by the container 5.

When the engagement section 252 is pressed in this way, the engagement section 252, the third arm forming section 251c and the second arm forming section 251b rotate about the bent portion of the rotation center between the first arm forming section 251*a* and the second arm forming section 251*b*. When the arm 251 rotates in this way, the arm is urged toward an initial position by elasticity of the arm 251. When the neck of the container 5 is guided to the upper end portions 252*a* of the two engagement sections 252, the two engagement sections 252 engage with the neck of the container 5. When the two engagement sections 252 engage with the container 5, the container connector 20A is fixed to the container 5.

Next, description will be made as to an operation of connecting the syringe connector 100A to the container connector 20A and forming the liquid flow path L1 and the gas flow path L2, with reference to FIGS. 21 and 35 and some of the drawings used in the first embodiment. Note that a movement of the first arm 231 and a movement of the second arm 232 of the stopper sleeve 230 are the same as in the first embodiment.

In a state where the syringe connector 100A is not connected to the container connector 20A as shown in FIG. 14, the head sleeve 180 is located in a lower end portion of an interior of the outer shell 110. Furthermore, the first arm 231 of the stopper sleeve 230 engages with the locking protrusion 128. Furthermore, as shown in FIG. 16, the second arm 232 of the stopper sleeve 230 abuts on the unlocking protrusion 129 of the outer shell barrel section 117, and is rotated to the position where the second arm protrusion 240 disengages from the locking recess 67 of the seal cap 60. A part of the second arm 232 is stored in the second arm storage recess 186 of the head sleeve 180.

Furthermore, a portion of the needle 170 in which the hole 172 is formed and a portion of the gas needle 170A in which the hole 172 is formed are stored in the needle seal 200A. That is, the hole 172 of the needle 170 and the hole 172 of the gas needle 170A are sealed with the needle seal 200A, and are air-tightly and liquid-tightly sealed.

Next, in the same manner as in FIG. 15 and FIG. 16, the seal cap small diameter section 63 of the seal cap 60A is inserted into the first hole section 191B of the head sleeve 180A. By the time when the upper end surface 77*a* of the container seal 70A comes in contact closely with the lower end surface 206*a* of the needle seal 200A, the lower end surface 238 of the first arm protrusion 237 of the first arm 231 of the stopper sleeve 230 abuts on the conical surface 62*a* of the seal cap intermediate diameter section 62. The upper end surface 77*a* of the container seal 70A which is formed as the curved surface is pressed by the lower end surface 206*a* of the needle seal 200A and is accordingly deformed, to come in contact closely with the lower end surface 206*a*.

When the syringe connector 100A is further lowered from this state, the first arm protrusion 237 is guided by the conical surface 62*a* and moved outwardly in the radial direction. With the movement of the first arm protrusion 237 outwardly in the radial direction, the first arm 231 rotates. In the state where the upper end surface 77*a* of the container seal 70A is in contact closely with the lower end surface 206*a* of the needle seal 200A, the first arm 231 is guided by the conical surface 62*a* and rotated to the position where the first arm disengages from the locking protrusion 128. At this time, a part of the first arm 231 is stored in the first arm storage recess 185 of the head sleeve 180. When the first arm 231 disengages from the locking protrusion 128, the head sleeve 180 can be moved upwardly in the outer shell main body 111.

As for the second arm 232, in the same manner as in FIG. 16, when the syringe connector 100A is lowered until the upper end surface 77*a* of the container seal 70A comes in contact closely with the lower end surface 206*a* of the needle seal 200A, the second arm protrusion 240 is disposed opposite to the locking recess 67.

When the syringe connector 100A is further lowered, the container connector 20A and the head sleeve 180A integrally move upwardly in the outer shell main body 111. When the head sleeve 180A moves upwardly in the outer shell main body 111, the needle 170 and the gas needle 170A move downwardly relative to the needle seal 200A.

As shown in FIG. 35, when the syringe connector 100A is further lowered, the container connector 20A and the head sleeve 180A further move upwardly in the outer shell main body 111. Consequently, the needle 170 and the gas needle 170A extend through the needle seal 200A and pierce the container seal 70A. Note that a gap between the needle 170 and the container seal 70A is liquid-tightly and air-tightly sealed when the container seal 70A comes in contact closely with the needle 170. Similarly, a gap between the gas needle 170A and the container seal 70A is liquid-tightly and air-tightly sealed when the container seal 70A comes in contact closely with the gas needle 170A.

In a state where the needle 170 and the gas needle 170A extend through the needle seal 200A, the second arm 232 moves upwardly relative to the unlocking protrusion 129. In this process of moving the second arm 232 upwardly relative to the unlocking protrusion 129, an abutment position of a middle portion of the unlocking protrusion 129 in the central portion 243*a* of the surface 243 of the second arm 232, which protrudes most inwardly in the radial direction of the outer shell main body 111, moves downwardly. Due to the downward movement of this abutment position, an urging force to urge the second arm protrusion 240 outwardly in the radial direction of the outer shell main body 111 decreases.

In the state where the needle 170 and the gas needle 170A extend through the needle seal 200A, the second arm 232 urged inwardly in the radial direction by the abutment on the unlocking protrusion 129 of the outer shell barrel section 117 is released. The second arm is rotated by elasticity (resilience) of the coupling section 233 and the abutment of the second arm protrusion 240 on the lower end portion of the second arm 232, to engage the second arm protrusion 240 in the locking recess 67. Specifically, the stopper sleeve 230 and the seal cap 60A are fixed to each other before the needle 170 extends through the needle seal 200.

When the syringe connector 100A is further lowered, as shown by a two-dot chain line in FIG. 35, the needle 170 and the gas needle 170A extend through the container seal 70A. The hole 172 of the needle 170 is disposed in the hole 311 of the seal pin 310, and the hole 172 of the gas needle 170A is disposed in the hole 312 of the seal pin 310.

When the hole 172 of the needle 170 is disposed in the hole 311, the liquid flow path forming section L3 of the container connector 20A communicates with the needle 170. When the liquid flow path forming section L3 communicates with the needle 170, the liquid flow path L1 is formed. When the hole 172 of the gas needle 170A is disposed in the hole 312, the gas flow path forming section L4 of the container connector 20A communicates with the gas needle 170A. When the gas flow path forming section L4 communicates with the gas needle 170A, the gas flow path L2 is formed.

When the syringe connector 100A is further lowered, the locking section claw section 156 of the locking section 113 rides across the lower end of the seal cap base 61, to move inwardly in the radial direction. The claw section 156 for the locking section rides across the lower end of the seal cap base 61 to move inwardly in the radial direction, thereby obtaining a state of being engageable with a portion between two seal cap protrusions 64 of the lower end of the seal cap 60A. That is, when the syringe connector 100A is pulled upwardly from this state relative to the container connector 20A, the claw section 156 for the locking section engages with the lower end of the seal cap base 61, and this movement is regulated.

When the syringe connector 100A is further lowered, the first guiding protrusion 65 abuts on the upper end of the first guide groove 126. Furthermore, the second guiding protrusion 182 abuts on the upper end of the second guide groove 127. Additionally, the seal cap protrusion 64 of the seal cap base 61 abuts on the lower end of the outer shell barrel section 117. By these abutments, the movement of the head sleeve 180A and the container connector 20A in the outer shell main body 111 is regulated. That is, the syringe connector 100A is lowered to a so-called bottom reached state.

The operator recognizes that the syringe connector 100A is lowered to reach the bottom and that the liquid flow path L1 and the gas flow path L2 are accordingly formed. When the syringe connector 100A is lowered to reach the bottom, the operator operates the syringe 6 to collect the chemical solution from the container 5. The liquid is moved from the container 5 to the syringe 6 through the liquid flow path L1.

Next, an operation of disconnecting the container connector 20A from the syringe connector 100A will be described. When disconnecting the container connector 20A from the syringe connector 100A, the operator presses the operating section 155 of the locking section 113 inwardly in the radial direction to a position where the claw section 156 for the locking section disengages from the lower end of the seal cap base 61.

Next, the operator pulls the syringe connector 100A upwardly. The head sleeve 180A is fixed to the seal cap 60A by the second arm 232 of the stopper sleeve 230. Consequently, when the syringe connector 100A is pulled upwardly, the outer shell 110, the needle 170 and the gas needle 170A move upwardly relative to the head sleeve 180A and the needle seal 200A.

When the outer shell 110, the needle 170 and the gas needle 170A move upwardly relative to the head sleeve 180A and the needle seal 200A, the needle 170 and the gas needle 170A move upwardly in the container seal 70A. When the syringe connector 100A is pulled upwardly by a predetermined distance, the needle 170 and the gas needle 170A are pulled out of the container seal 70A. The container seal 70A liquid-tightly and air-tightly seals the holes formed by the needle 170 and the gas needle 170A, by the resilience. Furthermore, the hole 172 of the needle 170 is sealed with the needle seal 200A. The hole 172 of the gas needle 170A is sealed with the needle seal 200A.

Furthermore, when the needle 170 and the gas needle 170A are pulled out of the container seal 70A and then the syringe connector 100A is further pulled upwardly by the predetermined distance, the second arm 232 is rotated by the unlocking protrusion 129 of the outer shell barrel section 117. Consequently, the second arm protrusion 240 of the second arm 232 moves outwardly from the locking recess 67 in the radial direction, and the second arm protrusion 240 and the locking recess 67 are disengaged. That is, the stopper sleeve 230 and the seal cap 60A are unlocked.

In this state, the portion of the needle 170 in which the hole 172 is formed and the portion of the gas needle 170A in which the hole 172 is formed are stored in the needle seal 200A, and both the holes 172 are sealed with the needle seal 200A. The needle seal 200A liquid-tightly and air-tightly seals the holes formed by the needle 170 and the gas needle 170A, by the resilience.

Note that the hole 172 of the needle 170 and the hole 172 of the gas needle 170A move out of the container seal 70A at the same timing, and are stored in the needle seal 200A at the same timing.

Thus, when the hole 172 of the needle 170 moves out of the hole 311 of the seal pin 310, the liquid flow path L1 is accordingly divided. The needle 170 that is a portion of the liquid flow path L1 formed in the syringe connector 100A is sealed, and the liquid flow path forming section L3 that is a portion of the liquid flow path L1 formed in the container connector 20A is sealed.

Similarly, when the hole 172 of the gas needle 170A moves out of the hole 312 of the seal pin 310, the gas flow path L2 is divided. The gas needle 170A that is a portion of the gas flow path L2 formed in the syringe connector 100A is sealed, and the gas flow path forming section L4 that is a portion of the gas flow path L2 formed in the container connector 20A is sealed.

When the seal cap 60A and the head sleeve 180 are unlocked and then the syringe connector 100A is further pulled upwardly, the seal cap 60A moves downwardly relative to the first arm 231 of the stopper sleeve 230. When the seal cap 60A moves downwardly relative to the first arm 231, urging of the first arm 231 by an outer peripheral surface of the seal cap 60A is released.

When the urging of the first arm 231 by the outer peripheral surface of the seal cap 60A is released, the first arm rotates by the elasticity (the resilience) of the coupling section 233. The first arm 231 rotates, and hence, as shown in FIG. 14, the upper end of the first arm is disposed below the locking protrusion 128. That is, the first arm 231 is in a state of being engageable with the locking protrusion 128.

The first arm 231 is in the state of being engageable with the locking protrusion 128. Consequently, the head sleeve 180A is prevented from being moved from a state where the needle 170 that is the portion of the liquid flow path L1 formed in the syringe connector 100A is sealed, i.e., the hole 172 is sealed with the needle seal 200A, and a state where the gas needle 170A that is the portion of the gas flow path L2 formed in the syringe connector 100A is sealed, i.e., the hole 172 is sealed with the needle seal 200A.

In the present embodiment, effects similar to those of the first embodiment can be obtained.

Furthermore, in the connection equipment 10A of the present embodiment, the gas flow path L2 includes the gas needle 170A, the hole 312 of the seal pin 310, and the gas flow path forming section L4. Additionally, the hole 172 of the gas needle 170A and the hole 172 of the needle 170 are sealed with the needle seal 200A.

Consequently, prior to shipment of the syringe connector 100A, in an inspection region that is the needle seal 200A, it is inspected whether or not the needle 170 that is the portion of the liquid flow path L1 on a syringe connector 100A side is sealed. Similarly, in the inspection region that is the needle seal 200A, it is inspected whether or not the gas needle 170A that is the portion of the gas flow path L2 on the syringe connector 100A side is sealed. Thus, the regions to be inspected can be decreased.

Prior to shipment of the container connector 20A, in the inspection region that is the container seal 70A, it is inspected whether or not the liquid flow path forming section L3 that is the portion of the liquid flow path L1 on a container connector 20A side is sealed. Similarly, in the inspection region that is the container seal 70A, it is inspected whether or not the gas flow path forming section L4 that is the portion of the gas flow path L2 on the syringe connector 100A side is sealed. Thus, inspections can be decreased.

Furthermore, the hydrophobic filter 300 is provided in the gas flow path L2. Consequently, even when the chemical solution is included in the air that flows from the container 5, this chemical solution is prevented from flowing on the syringe connector 100A side by the hydrophobic filter 300.

Additionally, a cross-sectional area of the recess 47 of the container cap main body 40A is set to be larger than a cross-sectional area of each of both side portions of the gas flow path L2 via the recess 47. Consequently, an area of the hydrophobic filter 300 in the gas flow path L2 can be increased. A portion of the hydrophobic filter 300 to which the chemical solution adheres is impermeable to air. However, in the present embodiment, the area of the hydrophobic filter 300 in the gas flow path L2 can be increased. Consequently, even when the chemical solution adheres on a part of the hydrophobic filter 300, the remaining parts are permeable to air. In consequence, it is possible to prevent occurrence of a state where the hydrophobic filter 300 cannot be permeable to air due to the adhesion of the chemical solution.

Next, connection equipment 10B according to a third embodiment of the present invention will be described with reference to FIG. 36 and FIG. 37. Note that a constitution having a function similar to that of the second embodiment is denoted with the same reference signs as in the second embodiment and description is omitted.

Figure 36:
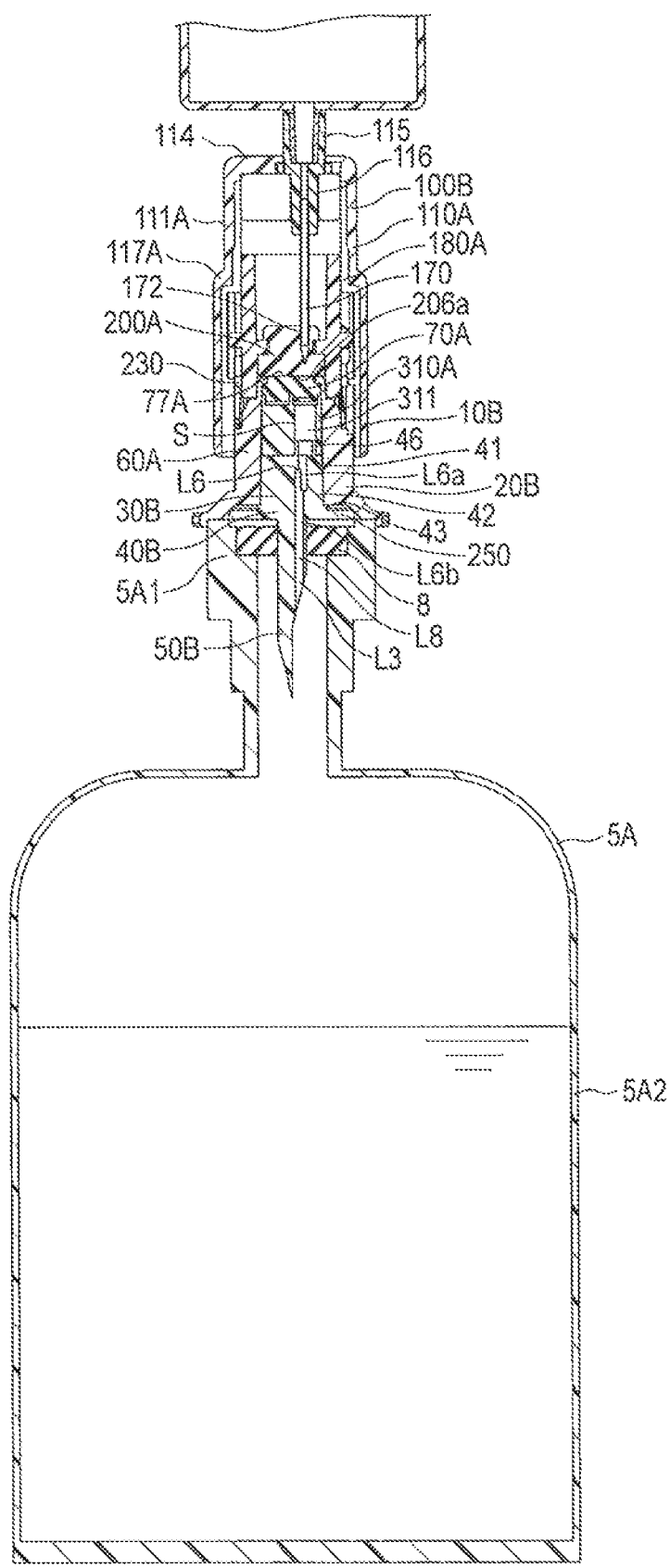
FIG. 36 is a cross-sectional view showing a state where a container and a syringe are connected by connection equipment according to a third embodiment of the present invention.

FIG. 36 is a cross-sectional view showing a state where the connection equipment 10B is connected to a container 5A. FIG. 37 is a cross-sectional view showing the connection equipment 10B. The connection equipment 10B is for use in a soft container having flexibility. The container 5A is an infusion bag that is one example of the soft container. When a chemical solution or the like is injected into the container 5A in a state where the container has the flexibility and leaves room for deformation, a volume of the container increases. Consequently, due to the increase of the volume, the container can maintain an internal pressure as a pressure equal to or substantially equal to an external pressure. The container 5A has a mouth 5A1 to which a container connector 20B for use in the connection equipment 10B is fixed, and a main body 5A2 that communicates with the mouth 5A1.

The mouth 5A1 is provided with a plug 8. The plug 8 is made of, for example, a rubber material. The mouth 5A1 is sealed with the plug 8. The main body 5A2 is made of, for example, a resin material, and has flexibility. The main body 5A2 has such flexibility that the main body can be deformed to increase its volume, when the chemical solution is injected into the main body through the container connector 20B. Note that another example of the soft container is an infusion bottle having flexibility.

Figure 37:
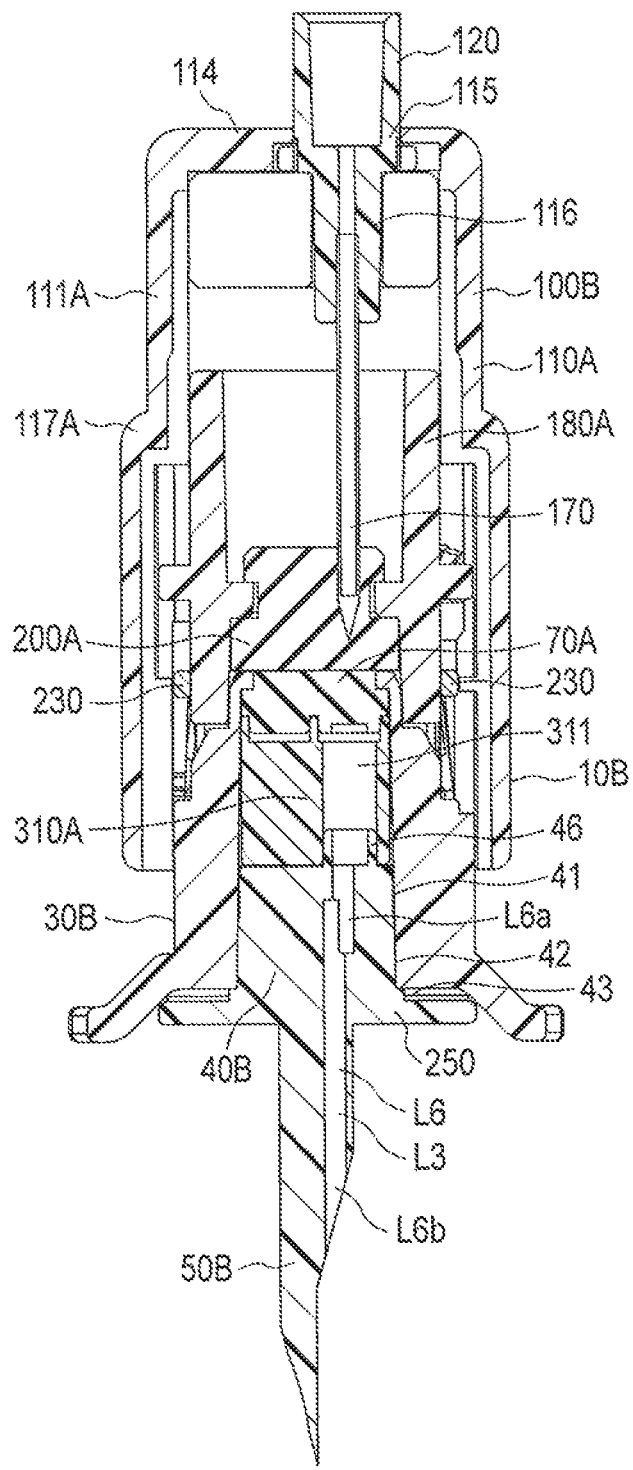
FIG. 37 is a cross-sectional view showing the connection equipment.

As shown in FIG. 36 and FIG. 37, the connection equipment 10B has the container connector 20B fixed to the container 5A, and a syringe connector 100B formed to be fixable to a barrel 7 of a syringe 6 and removably fixed to the container connector 20B.

In the present embodiment, as an example, an up-down direction is set to the connection equipment 10B based on a state where the container 5A is disposed below and the syringe 6 is disposed above. Note that an axial direction of an after-mentioned container cap 30B of the container connector 20B and an axial direction of a seal cap 60A are parallel to the up-down direction, and an axial direction of an after-mentioned outer shell main body 111A of the syringe connector 100B is parallel to the up-down direction.

Firstly, description will be made as to the container connector 20B. The container connector 20B has the container cap 30B fixed to the container 5A, a seal pin 310A, the seal cap 60A fixed to the container cap 30B, and a container seal 70A provided in the seal cap 60A.

The container cap 30B has a liquid flow path forming section L3 that constitutes a part of a liquid flow path L1 via which an interior of the container 5A communicates with an interior of the barrel 7 and through which a liquid (the chemical solution) can flow. The container cap 30B specifically has a container cap main body 40B fixed to the container 5A, and a needle section 50B to be inserted in the container 5A.

The container cap main body 40B is formed in a columnar shape having a plurality of diameters. The container cap main body 40B has a container cap small diameter section 41 that constitutes an upper section, a container cap intermediate diameter section 42 that constitutes a middle section in the up-down direction, and a container cap large diameter section 43 that constitutes a lower section. Note that in the present embodiment, the container cap small diameter section 41 has a diameter slightly smaller than a diameter of the container cap intermediate diameter section 42.

In an upper surface of the container cap main body 40B, a protrusion 46 that protrudes relative to another portion is integrally formed at a position shifted outwardly in a radial direction relative to an axis of the container cap main body 40B. The protrusion 46 is formed in a cylindrical shape so that an axis of the protrusion is parallel to the axis of the container cap main body 40B. In the container cap main body 40B, a part L6 of the liquid flow path forming section L3 is formed. The part L6 communicates with an inner side of the protrusion 46. Furthermore, the part L6 of the liquid flow path forming section L3 extends to a lower end of the container cap main body 40B.

Note that in the present embodiment, the part L6 of the liquid flow path forming section L3 includes two portions shifted in a radial direction of the container cap main body 40B and arranged to communicate with a part L8 of the flow path forming section L3 formed in the after-mentioned needle section 50B. A portion L6b of these two portions which is disposed below a portion L6a disposed above is disposed at a position shifted to an axial side of the container cap main body 40B. The portion L6a and the portion L6b partially communicate with the container cap main body 40A in the radial direction. Each of the portion L6a and the portion L6b is a hole having an axis parallel to the axis of the container cap main body 40B.

The needle section 50B extends downwardly from the lower end of the container cap main body 40B in parallel with the axis of the container cap main body 40B. The needle section 50B is disposed, for example, coaxially with the container cap main body 40. In the needle section 50B, a lower end, i.e., a leading end when being inserted in the container 5A is formed as a sharp head.

In the needle section 50B, the part L8 of the liquid flow path forming section L3 is formed. The part L8 of the liquid flow path forming section L3 communicates with the part L6 of the liquid flow path forming section L3. The part L6 of the liquid flow path forming section L3 is open in a lower end surface of the needle section 50A. Each of the lower portion L6b of the part L6 of the liquid flow path forming section L3 and the part L8 is a hole, for example, having a cross-sectional shape that is constant in the axial direction.

The seal pin 310A is disposed on the container cap main body 40B. The seal pin 310A is formed in a columnar shape having the same diameter as in the container cap main body 40B. The seal pin 310A has a hole 311 in which the protrusion 46 can be disposed.

The seal cap 60A is formed in a tubular shape in which the container cap main body 40B, the seal pin 310A and the container seal 70A are stored. Note that in the present embodiment, the seal cap 60A described in the second embodiment is for use as one example of the seal cap.

Next, description will be made as to the syringe connector 100B. The syringe connector 100B has an outer shell 110A, a needle 170, a tubular head sleeve 180A that is stored movably in the outer shell 110A while storing therein a part of the needle 170, a needle seal 200A fixed to the head sleeve 180A, and a stopper sleeve 230 formed so that the head sleeve 180A can be selectively fixed to the outer shell 110A and so that the head sleeve 180A can be selectively fixed to the container connector 20B.

The outer shell 110A has the outer shell main body 111A, and a locking section 113 that can removably lock the outer shell main body 111A to the container connector 20B.

The outer shell main body 111A has an outer shell ceiling wall 114, a syringe fixing section 115, a needle fixing section 116, and an outer shell barrel section 117A.

The outer shell barrel section 117A is formed in a cylindrical shape with which a seal cap base 61 of the container connector 20B movably fits. The outer shell barrel section 117A is disposed coaxially with the outer shell ceiling wall 114. The outer shell barrel section 117A is configured similarly to the outer shell barrel section 117 described in the second embodiment, except a constitution that communicates with an air bag storage section 150.

The head sleeve 180A is formed in a tubular shape that can move in the outer shell main body 111A.

Next, an operation of connecting the container 5A to the container connector 20B will be described. When the container 5A is connected to the container connector 20B, an operator disposes the container 5A, for example, in a posture in which the mouth 5A1 is located above the main body 5A2.

Next, the operator attaches a tip of the needle section 50B of the container connector 20B to the plug 8 of the mouth 5A1. Next, the operator inserts the needle section 50B in the plug 8 until the container cap main body 40B abuts on the mouth 5A1.

When the needle section 50B is inserted until the container cap main body 40B abuts on the mouth 5A1, the tip of the needle section 50B extends through the plug 8 and is disposed in the main body 5A2. The needle section 50B is held in the mouth 5A1 by resilience of the plug 8 that is to close a hole formed by the needle section 50B. The container connector 20B is fixed to the container 5A, when the needle section 50B is held by the plug 8.

Next, description will be made as to an operation of connecting the syringe connector 100A to the container connector 20A and forming the liquid flow path L1.

In a state where the syringe connector 100B is not connected to the container connector 20B, the head sleeve 180A is located in a lower end portion of an interior of the outer shell 110A. Furthermore, a first arm 231 of the stopper sleeve 230 engages with a locking protrusion 128. A second arm 232 of the stopper sleeve 230 abuts on an unlocking protrusion 129 of the outer shell barrel section 117, and is rotated to a position where a second arm protrusion 240 disengages from a locking recess 67 of the seal cap 60. A part of the second arm 232 is stored in a second arm storage recess 186 of the head sleeve 180A.

Furthermore, a portion of the needle 170 in which a hole 172 is formed is disposed in the needle seal 200A. That is, the hole 172 of the needle 170 is sealed with the needle seal 200A, and is air-tightly and liquid-tightly sealed.

Next, a seal cap small diameter section 63 of the seal cap 60A is inserted in a first hole section 191B of the head sleeve 180A. By the time when an upper end surface 77a of the container seal 70A comes in contact closely with a lower end surface 206a of the needle seal 200A, a lower end surface 238 of a first arm protrusion 237 of the first arm 231 of the stopper sleeve 230 abuts on a conical surface 62a of a seal cap intermediate diameter section 62. The upper end surface 77a of the container seal 70A which is formed as the curved surface is pressed by the lower end surface 206a of the needle seal 200A and is accordingly deformed, to come in contact closely with the lower end surface 206a.

When the syringe connector 100B is further lowered from this state, the first arm protrusion 237 is guided by the conical surface 62a and moved outwardly in the radial direction. With the movement of the first arm protrusion 237 outwardly in the radial direction, the first arm 231 rotates. In the state where the upper end surface 77a of the container seal 70A is in contact closely with the lower end surface 206a of the needle seal 200A, the first arm 231 is guided by the conical surface 62a and rotated to a position where the first arm disengages from the locking protrusion 128. At this time, a part of the first arm 231 is stored in a first arm storage recess 185 of the head sleeve 180A. When the first arm 231 disengages from the locking protrusion 128, the head sleeve 180A is in a state of being movable upwardly in the outer shell main body 111A.

As for the second arm 232, when the syringe connector 100B is lowered until the upper end surface 77a of the container seal 70A comes in contact closely with the lower end surface 206a of the needle seal 200A, the second arm protrusion 240 is disposed opposite to the locking recess 67.

When the syringe connector 100B is further lowered, the container connector 20B and the head sleeve 180A integrally move upwardly in the outer shell main body 111A. When the head sleeve 180B moves upwardly in the outer shell main body 111A, the needle 170 moves downwardly relative to the needle seal 200A.

When the syringe connector 100B is further lowered, the container connector 20B and the head sleeve 180A further move upwardly in the outer shell main body 111A. Consequently, the needle 170 disposed in the needle seal 200A extends through the needle seal 200A and pierces the container seal 70A. Note that a gap between the needle 170 and the container seal 70A is liquid-tightly and air-tightly sealed when the container seal 70A comes in contact closely with the needle 170.

In a state where the needle 170 extends through the needle seal 200A, the second arm 232 moves upwardly relative to the unlocking protrusion 129. In this process of moving the second arm 232 upwardly relative to the unlocking protrusion 129, an abutment position of a middle portion of the unlocking protrusion 129 in a central portion 243a of a surface 243 of the second arm 232, which protrudes most inwardly in the radial direction of the outer shell main body 111, moves downwardly. Due to the downward movement of this abutment position, an urging force to urge the second arm protrusion 240 outwardly in the radial direction of the outer shell main body 111 decreases.

In the state where the needle 170 extends through the needle seal 200A, urging of the second arm 232 inwardly in the radial direction by the abutment on the unlocking protrusion 129 of the outer shell barrel section 117 is released. The second arm is rotated by elasticity (resilience) of a coupling section 233 and the abutment of the second arm protrusion 240 on a lower end portion of the second arm 232, to engage the second arm protrusion 240 in the locking recess 67. Specifically, the stopper sleeve 230 and the seal cap 60A are fixed to each other before the needle 170 extends through the needle seal 200A. Furthermore, also in the state where the needle 170 extends through the needle seal 200A, the fixing of the stopper sleeve 230 and the seal cap 60A is maintained.

When the syringe connector 100B is further lowered, the needle 170 extends through the container seal 70A, and the hole 172 of the needle 170 is disposed in the hole 311 of the seal pin 310A.

When the hole 172 of the needle 170 is disposed in the hole 311, the liquid flow path forming section L3 of the container connector 20B communicates with the needle 170 via the hole 311. When the liquid flow path forming section L3 communicates with the needle 170, the liquid flow path L1 is formed.

When the syringe connector 100B is further lowered, a locking section claw section 156 of the locking section 113 rides across a lower end of the seal cap base 61, to move inwardly in the radial direction. The claw section 156 for the locking section rides across the lower end of the seal cap base 61 to move inwardly in the radial direction, thereby obtaining a state of being engageable with a portion between two seal cap protrusions 64 of a lower end of the seal cap 60A. That is, when the syringe connector 100B is pulled upwardly from this state relative to the container connector 20B, the claw section 156 for the locking section engages with the lower end of the seal cap base 61, and this movement is regulated.

When the syringe connector 100B is further lowered, a first guiding protrusion 65 abuts on an upper end of a first guide groove 126. Furthermore, a second guiding protrusion 182 abuts on an upper end of a second guide groove 127. Additionally, the seal cap protrusion 64 of the seal cap base abuts on a lower end of the outer shell barrel section 117. By these abutments, the movement of the head sleeve 180B and the container connector 20B in the outer shell main body 111A is regulated. That is, the syringe connector 100B is lowered to a so-called bottom reached state.

The operator recognizes that the syringe connector 100B is lowered to reach the bottom and that the liquid flow path L1 is accordingly formed. When the syringe connector 100B is lowered to reach the bottom, the operator operates the syringe 6 to inject the chemical solution into the container 5A. The liquid is moved from the container 5A to the syringe 6 through the liquid flow path L1.

When the chemical solution is injected from the syringe 6 into the main body 5A2 of the container 5A, an internal volume of the main body 5A2 increases. The main body 5A2, having the flexibility, can be deformed to increase the volume as described above. Furthermore, even when the chemical solution is injected, the main body 5A2 has room for the deformation to keep the internal pressure constant or substantially constant before and after the injection. Consequently, when the chemical solution is injected into the container 5A, the volume of the main body 5A2 increases, and hence the pressure in the main body 5A2 is kept to be constant or substantially constant before and after the chemical solution is injected from the syringe 6.

Furthermore, the chemical solution stored in the container 5A is moved from the container 5A to the syringe 6 or the like. In this case, even when the internal volume decreases, the container 5A has room for the deformation to keep the internal pressure constant or substantially constant before and after the movement. Consequently, when the chemical solution is moved from the container 5A to the syringe 6 or the like, the chemical solution in the container 5A is moved to the syringe 6 due to the decrease of the volume of the container 5A. Even in this case, the pressure in the container 5A is kept to be constant or substantially constant before and after the movement of the chemical solution.

Next, an operation of disconnecting the container connector 20B from the syringe connector 100B will be described. When disconnecting the container connector 20B from the syringe connector 100B, the operator presses an operating section 155 of the locking section 113 inwardly in the radial direction to a position where the claw section 156 for the locking section disengages from the lower end of the seal cap base 61.

Next, the operator pulls the syringe connector 100B upwardly. The head sleeve 180B is fixed to the seal cap 60A by the second arm 232 of the stopper sleeve 230. Consequently, when the syringe connector 100B is pulled upwardly, the outer shell 110A and the needle 170 move upwardly relative to the head sleeve 180B and the needle seal 200A.

When the outer shell 110A and the needle 170 move upwardly relative to the head sleeve 180A and the needle seal 200A, the needle 170 moves upwardly in the container seal 70A. When the syringe connector 100B is pulled upwardly by a predetermined distance, the needle 170 is pulled out of the container seal 70A. The container seal 70A liquid-tightly and air-tightly seals the hole formed by the needle 170, by the resilience. Furthermore, the hole 172 of the needle 170 is sealed with the needle seal 200A.

Furthermore, when the needle 170 is pulled out of the container seal 70A and then the syringe connector 100B is further pulled upwardly by a predetermined distance, the second arm 232 is rotated by the unlocking protrusion 129 of the outer shell barrel section 117A. Consequently, the second arm protrusion 240 of the second arm 232 moves outwardly from the locking recess 67 in the radial direction, and the second arm protrusion 240 and the locking recess 67 are disengaged. That is, the stopper sleeve 230 and the seal cap 60A are unlocked.

In this state, the portion of the needle 170 in which the hole 172 is formed is stored in the needle seal 200A, and the hole 172 is sealed with the needle seal 200A. The needle seal 200A liquid-tightly and air-tightly seals the hole formed by the needle 170, by the resilience.

Thus, when the hole 172 of the needle 170 moves out of a space between the container seal 70A and the container cap 30B in the seal cap 60A, the liquid flow path L1 is accordingly divided. The needle 170 that is a portion of the liquid flow path L1 formed in the syringe connector 100B is sealed, and the liquid flow path forming section L3 that is a portion of the liquid flow path L1 formed in the container connector 20B is sealed.

When the seal cap 60A and the head sleeve 180A are unlocked and then the syringe connector 100B is further pulled upwardly, the seal cap 60A moves downwardly relative to the first arm 231 of the stopper sleeve 230. When the seal cap 60A moves downwardly relative to the first arm 231, urging of the first arm 231 by an outer peripheral surface of the seal cap 60A is released.

When the urging of the first arm 231 by the outer peripheral surface of the seal cap 60A is released, the first arm rotates by the elasticity (the resilience) of the coupling section 233. The first arm 231 rotates, and hence, an upper end of the first arm is disposed below the locking protrusion 128. That is, the first arm 231 is in a state of being engageable with the locking protrusion 128.

The first arm 231 is in the state of being engageable with the locking protrusion 128. Consequently, the head sleeve 180A is prevented from being moved from a state where the needle 170 that is the portion of the liquid flow path L1 formed in the syringe connector 100B is sealed, i.e., the hole 172 is sealed with the needle seal 200A.

In the connection equipment 10B having such a constitution, only by pushing the syringe connector 100B into the container connector 20 in one direction, the head sleeve 180 and the container connector 20B can be locked by the second arm 232 of the stopper sleeve 230 and the locking recess 67 of the seal cap 60 in the state where the liquid flow path L1 is formed in the syringe connector 100B and the container connector 20B. Furthermore, the syringe connector 100B and the container connector 20B can be locked by the locking section 113 and the lower end of the seal cap base 61.

Specifically, the operation of connecting the syringe connector 100B to the container connector 20B and the locking operation of preventing the container connector 20B from being disconnected from the syringe connector 100B in the state where the liquid flow path L1 is formed can be achieved with one operation of pushing the syringe connector 100B into the container connector 20B in the one direction. Both the disconnecting and the unlocking can be achieved with one operation of similarly pressing the operating section 155 by the unlocking protrusion 129 of the outer shell barrel section 117A and pulling the syringe connector 100B out of the container connector 20B in the one direction.

Thus, the connection and locking of the syringe connector 100 to the container connector 20 can be achieved with one continuous operation, and the unlocking and disconnecting of the syringe connector 100 from the container connector 20 can be achieved with one continuous operation. Consequently, the operation of connecting and locking the syringe connector 100 to the container connector 20 and the unlocking and disconnecting operation can be facilitated.

Furthermore, the syringe connector 100B may only be pushed into the container connector 20B until the bottom is reached, and hence, the operation is easy. Furthermore, the operator does not have to take an operation amount of the syringe connector 100B, i.e., a push-in amount of the syringe connector 100 into consideration, and hence, the operation is easy.

Additionally, the first arm 231 of the stopper sleeve 230 and the locking protrusion 128 can lock a state where the needle 170 that constitutes the liquid flow path in the syringe connector 100B is sealed, while the container connector 20B is disconnected from the syringe connector 100B.

Consequently, when the chemical solution is collected into the syringe 6 and the container connector 20B is then disconnected from the syringe connector 100B, it is possible to prevent the chemical solution from leaking out of the needle 170 that constitutes the liquid flow path in the syringe connector 100B.

Furthermore, the first arm 231 and the locking protrusion 128 can be unlocked by an operation of pushing the syringe connector 100 into the container connector 20 with the conical surface 62a that is the outer peripheral surface of the seal cap 60 of the container connector 20B.

Consequently, the unlocking operation of the first arm 231 and the locking protrusion 128, the connecting operation of the syringe connector 100 and the container connector 20 and the locking operation of the second arm 232 and the locking recess 67 can be achieved with a series of operations. Consequently, the operation of the connection equipment 10B can be facilitated.

Next, connection equipment 10C according to a fourth embodiment will be described with reference to FIG. 38 and FIG. 39. Note that a constitution having a function similar to that of the third embodiment is denoted with the same reference signs as in the first embodiment and description is omitted.

Figure 38:
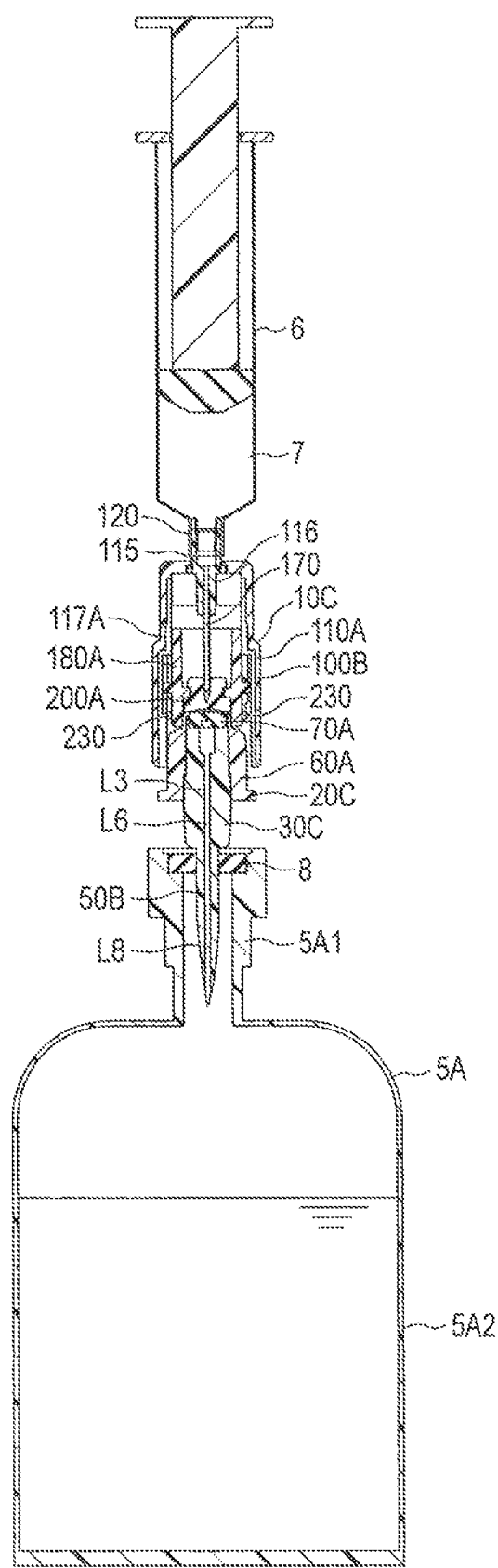
FIG. 38 is a cross-sectional view showing a state where a container and a syringe are connected by a modification of the connection equipment.
Figure 39:
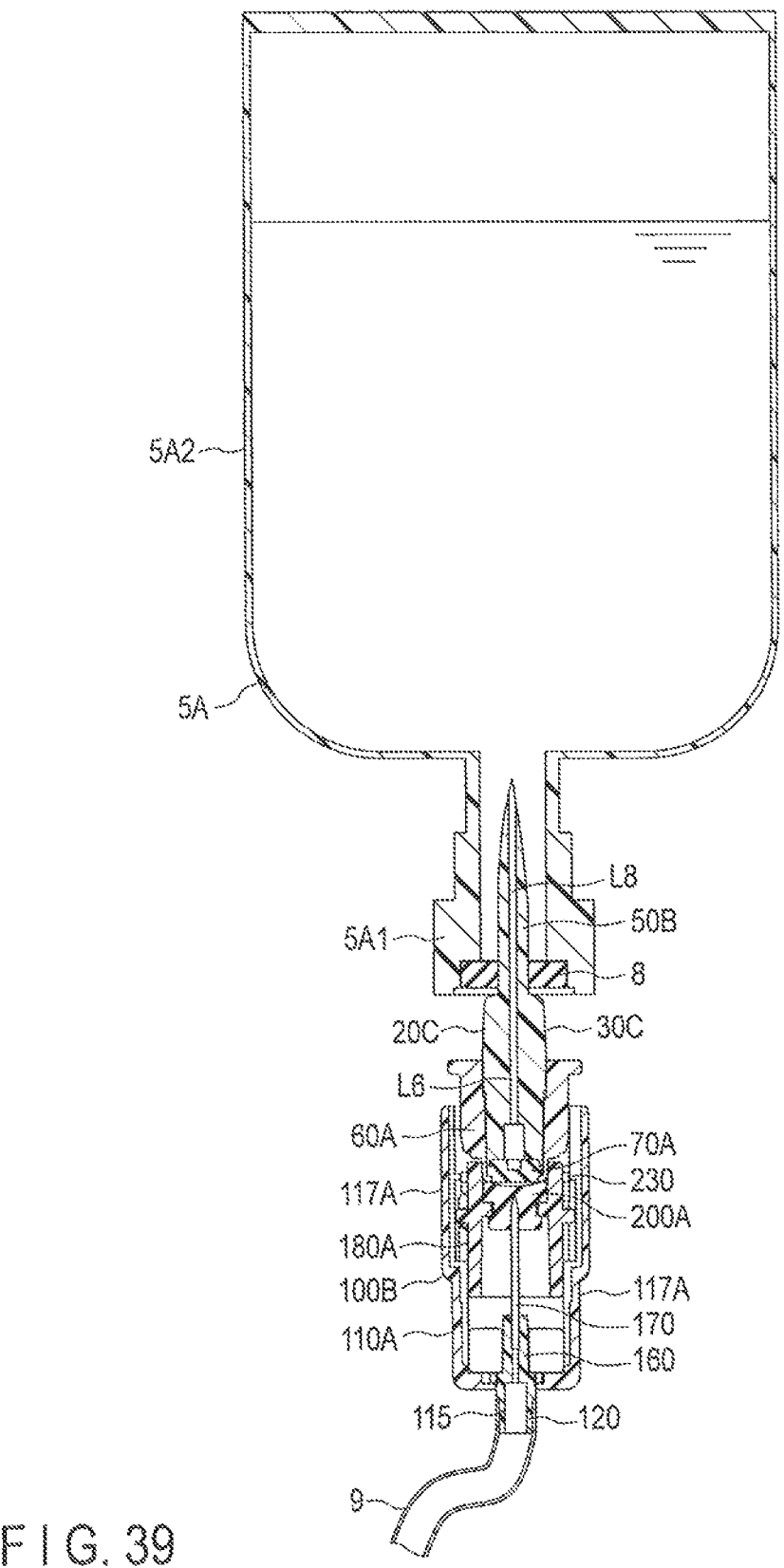
FIG. 39 is a cross-sectional view showing a state where a container and a syringe are connected by a modification of the connection equipment.

FIG. 38 and FIG. 39 are cross-sectional views showing the connection equipment 10C. As shown in FIG. 38 and FIG. 39, the connection equipment 10C has a container connector 20C fixed to a container 5A, and a syringe connector 100B removably fixed to a container connector 20B.

In the present embodiment, as an example, an up-down direction is set to the connection equipment 10C based on a state where the container 5A is disposed below and a syringe is disposed above. Note that an axial direction of an after-mentioned container cap 30B of the container connector 20B and an axial direction of a seal cap 60A are parallel to the up-down direction. An axial direction of an after-mentioned outer shell main body 111A of the syringe connector 100B is parallel to the up-down direction.

Firstly, description will be made as to the container connector 20C. The container connector 20C is configured as a so-called spike needle. Specifically, the container connector 20C has a main body 30C, a needle section 50B, the seal cap 60A fixed to the main body 30C, and a container seal 70A provided in the seal cap 60A.

A cross section of the main body 30C orthogonal to the axial direction is larger than a cross section of the needle section 50B orthogonal to the axial direction. The main body 30C is formed, for example, in a columnar shape. The main body 30C has therein a part L6 of a liquid flow path forming section L3 that constitutes a part of a liquid flow path L1 through which a liquid (a chemical solution) can flow. The part L6 is disposed, for example, coaxially with the main body 30C. A cross section of a portion of the part L6 that is located in an upper section of the main body 30C is larger than a cross section of a portion below this portion.

The needle section 50B extends downwardly from a lower end of the main body 30C in parallel with an axis of the main body 30C. The needle section 50B is disposed, for example, coaxially with the main body 30C. A part L8 formed in the needle section 50B is disposed coaxially with the needle section 50B. The part L8 is linearly aligned with the part L6.

The seal cap 60A is fixed to an upper end portion of the main body 30C. The container seal 70A seals an upper end opening of the part L6 in the main body 30C. Furthermore, the container seal 70A seals an opening of the seal cap 60A.

In the syringe connector 100B, a needle 170 is disposed coaxially with an outer shell barrel section 117A in the present embodiment.

Next, one example of use of the connection equipment 10C will be described. As shown in FIG. 38, an operator inserts the needle section 50B of the container connector 20C in a plug 8 of a mouth 5A1 of the container 5A. Next, the syringe connector 100B connected to the syringe 6 is connected to the container connector 20C from above the container 5A. This connection is similar to that of the third embodiment.

When the operator connects the syringe connector 100B to the container connector 20C, the operator operates the syringe 6 to move the chemical solution from the syringe 6 into the container 5A. As shown in FIG. 39, the operator disposes an integral unit of the container 5A and the connection equipment 10C in a posture in which the container 5A is located above the connection equipment 10C.

Next, the operator changes the syringe 6 to a tube 9. For example, the tube 9 is for use in putting a patient on a drip. An injection needle to be inserted in the patient is provided at a tip of the tube 9.

An operator's operation of changing the syringe 6 to the tube 9 includes, for example, removing, from the container connector 20C, the syringe connector 100B to which the syringe 6 is fixed, and connecting, to the container connector 20C, another syringe connector 100B in which the tube 9 is connected to a syringe fixing section main body 120.

In the present embodiment, effects similar to those of the third embodiment are obtained. Furthermore, also in a use application in which the chemical solution is injected from the syringe 6 into the container 5A and then the patient is put on a drip of the chemical solution of the container 5A, the chemical solution can be prevented from leaking to an outside.

Note that in the present embodiment, the container connector 20C is configured to be connectable to the syringe connector 100B. However, as in a modification shown in FIG. 40, the container connector may be configured to be connectable to either one of the syringe connector 100A described in the second embodiment or the syringe connector 100B described in the second embodiment. Specifically, in the container connector 20C, a gas flow path forming section L4 is formed. A part L7 of the gas flow path forming section L4 is formed in the main body 30C. A part L9 of the gas flow path forming section L4 is formed in the needle section 50B. In this modification, the liquid flow path forming section L3 is disposed at a position which is shifted from the axis of the main body 30C and at which the section can communicate with the needle 170. The gas flow path forming section L4 is disposed at a position which is shifted from the axis of the main body 30C and at which the section can communicate with a gas needle 170A.

Figure 40:
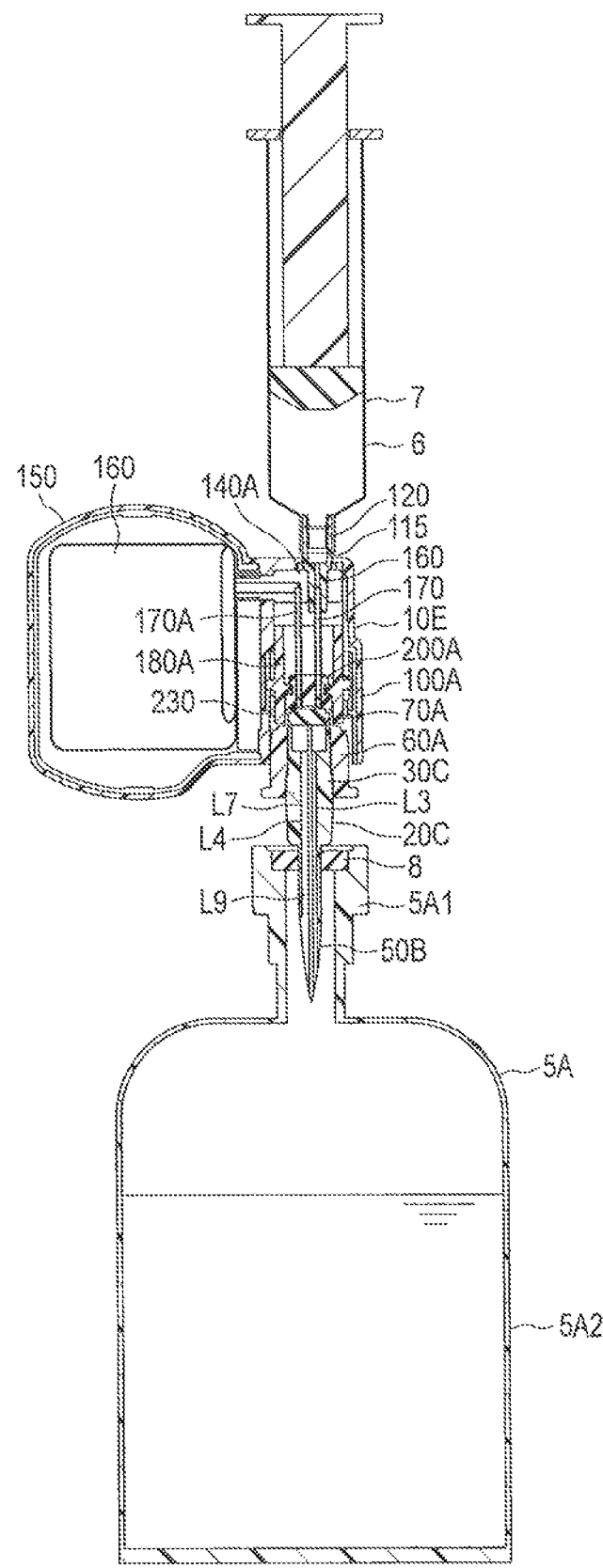
FIG. 40 is a cross-sectional view showing a state where a container and a syringe are connected by a modification of the connection equipment.

In this modification, as shown in FIG. 40, also in an operation of injecting a chemical solution from a syringe 6 to a container 5A, a syringe connector 100A having an air bag 160 that is a pressure adjustment section is usable. Consequently, when the syringe 6 is connected to the container connector 20C via the syringe connector 100A to inject, into the container 5A, the chemical solution in the syringe 6, a pressure in the container 5A can be prevented from varying before and after the injection.

Figure 41:
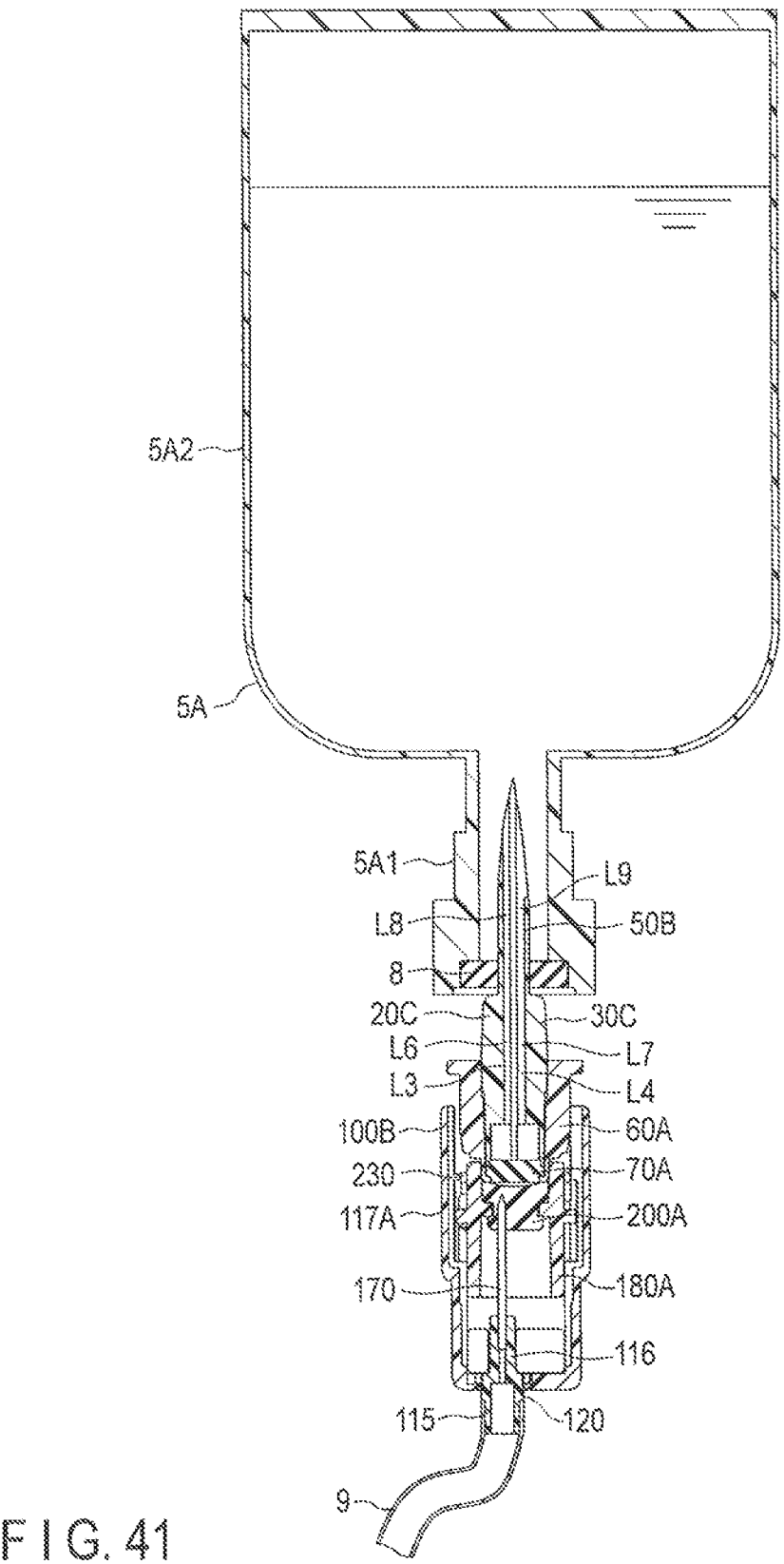
FIG. 41 is a cross-sectional view showing a state where a container and a tube are connected by a modification of the connection equipment.

Furthermore, as shown in FIG. 41, when a patient is put on a drip of a chemical solution in a container 5A, a syringe connector 100B connected to a tube 9 is connected to a container connector 20C. Consequently, the chemical solution in the container 5A can be guided to the tube 9.

That is, in this modification, the container connector 20C can be connected to the syringe connector 100A or the syringe connector 100B.

Next, connection equipment 10D according to a fifth embodiment will be described with reference to FIG. 42 and FIG. 43. Note that a constitution having a function similar to that of the fourth embodiment is denoted with the same reference signs as in the fourth embodiment and description is omitted.

Figure 42:
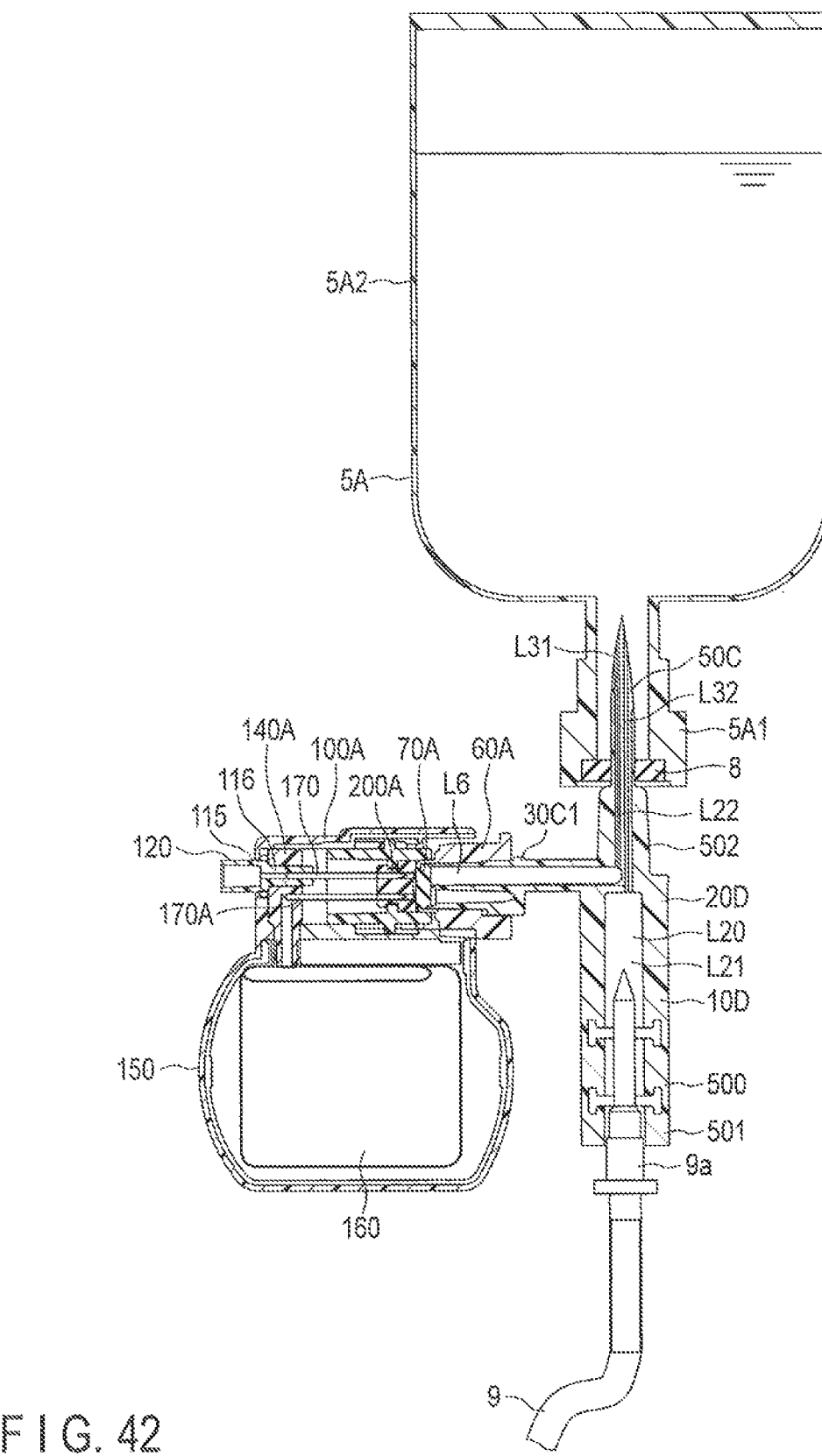
FIG. 42 is a cross-sectional view showing a state where a container, a syringe and a tube are connected by a modification of the connection equipment.
Figure 43:
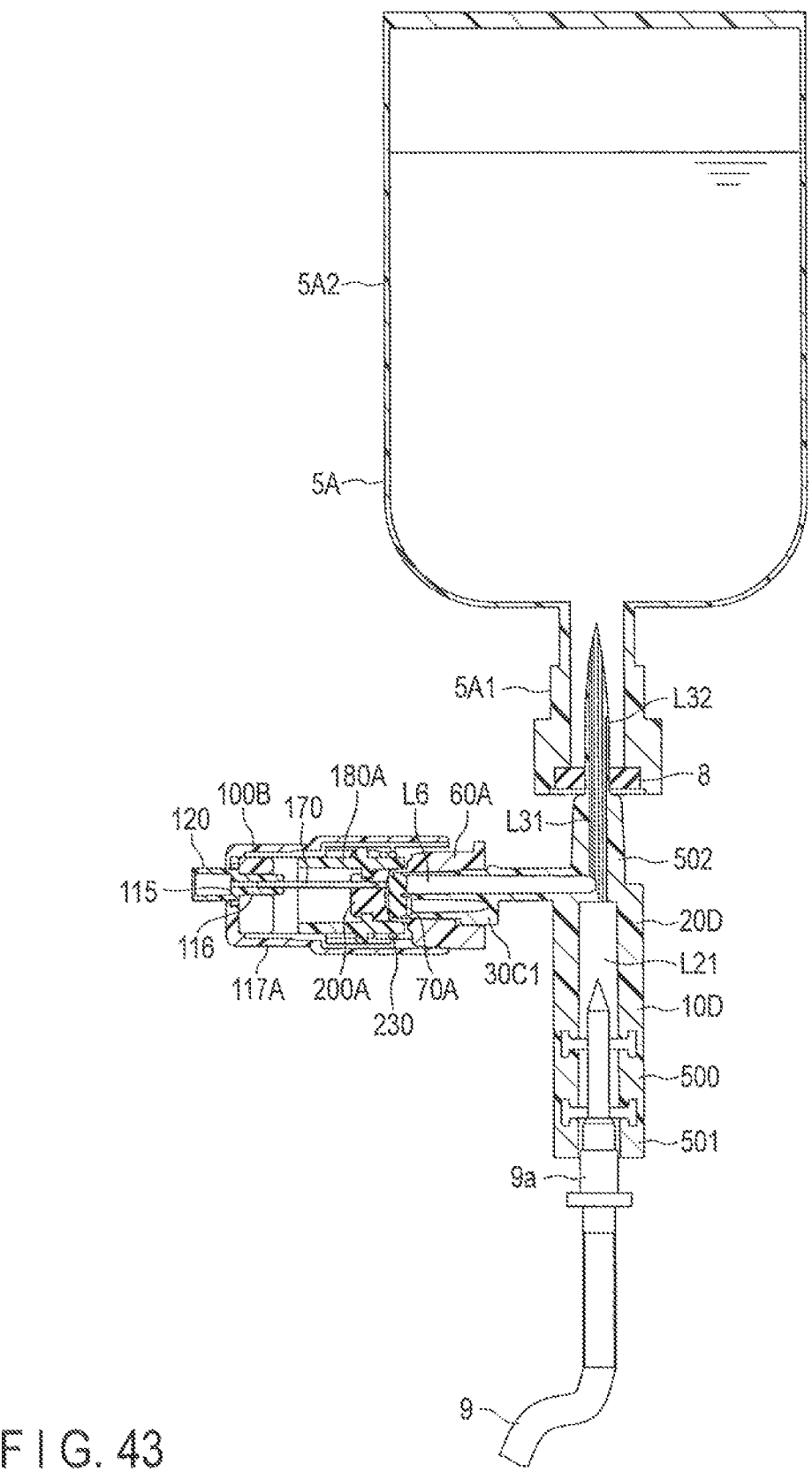
FIG. 43 is a cross-sectional view showing a state where a container, a syringe and a tube are connected by a modification of the connection equipment.

FIG. 42 and FIG. 43 are cross-sectional views showing the connection equipment 10D. As shown in FIG. 42 and FIG. 43, the connection equipment 10D has a container connector 20D. Furthermore, the connection equipment 10D has the syringe connector 100A described in the second embodiment, or the syringe connector 100B described in the third embodiment.

The container connector 20D has a tube connecting section 500, a main body 30C1, a needle section 50C, a seal cap 60A fixed to the main body 30C1, and a container seal 70A provided in the seal cap 60A.

In the tube connecting section 500, there is formed a flow path forming section L21 that is a part of a fluid flow path L20 via which an interior of a container 5A communicates with a tube 9. For example, the tube connecting section 500 is formed in a cylindrical shape having different outer diameters. Specifically, the tube connecting section has a first portion 501 formed in a cylindrical shape having a constant outer diameter and a second portion 502 formed continuously with the first portion 501.

The tube 9 is connected to an interior of the first portion 501. At an end portion of the tube 9, an insertion member 9a to be inserted in the first portion 501 is provided. The insertion member 9a is fitted and fixed into the first portion 501, and a gap between the member and an inner peripheral surface of the first portion 501 is sealed. The insertion member 9a has a flow path therein. This flow path communicates with the interior of the first portion 501, and the tube 9.

Furthermore, in the first portion 501 and the second portion 502, there is formed a flow path forming section L22 that is a part of a liquid flow path L1 via which the interior of the container 5A communicates with a syringe 6.

The main body 30C1 is formed integrally with the tube connecting section 500. The main body 30C1 is formed in an end portion of the first portion 501 opposite to the tube 9. The main body 30C1 is formed in a shape that protrudes in a direction orthogonal to an axis of the tube connecting section 500.

A part L6 that is a flow path in the main body 30C1 communicates with the flow path forming section L22 formed in the first portion 501.

The needle section 50C is formed in an end portion of the second portion 502. The needle section 50C is formed to be insertable in a plug 8 of the container 5A. In the needle section 50C, there are formed a flow path forming section L31 that is a part of the liquid flow path L1 via which the interior of the container 5A communicates with the syringe 6, and a flow path forming section L32 that is a part of the fluid flow path L20.

The flow path forming section L31 communicates with the flow path forming section L22. The flow path forming section L32 communicates with the flow path forming section L21.

In the connection equipment 10D configured in this manner, as shown in FIG. 42 and FIG. 43, the container connector 20D can be connected to one of the syringe connector 100A described in the second embodiment or the syringe connector 100B described in the third embodiment.

In the connection equipment 10D configured in this manner, the effect of the second embodiment and the effect of the third embodiment can be obtained. Furthermore, when a pressure in the container 5A is required to be adjusted during injection of a chemical solution from the syringe 6 into the container 5A, as shown in FIG. 42, the syringe connector 100A is used. Consequently, the pressure in the container 5A can be maintained to be constant or substantially constant by an air bag 160. Alternatively, when the pressure in the container 5A is not required to be adjusted during the injection of the chemical solution from the syringe 6 into the container 5A, as shown in FIG. 43, the syringe connector 100B is usable.

Note that it is not limited that the container 5 or 5A is made of a transparent resin material. The container 5 or 5A may have shading properties. Furthermore, the container 5 or 5A contains the chemical solution as one example, but what is contained is not limited to the chemical solution. In another example, the container 5 or 5A may contain a liquid fuel of a fuel cell, a liquid chemical, or a liquid food. Furthermore, a fluid to be moved from the syringe 6 to the container 5 or 5A is not limited to the chemical solution. In the other example, the liquid fuel of the fuel cell, the liquid chemical or the liquid food may be moved from the syringe 6 to the container 5 or 5A.

Furthermore, in the first to third embodiments and the modification shown in FIG. 38 and FIG. 39, the syringe 6 or the tube 9 is connected to the syringe connector 100A or 100B, as one example of equipment through which the fluid can move. However, the equipment that is connected to the syringe connector 100A or 100B and through which the fluid can move is not limited to the syringe 6 or the tube 9.

Note that the present invention is not limited to the above embodiment, and can be variously deformed in an implementation stage without departing from the scope. For example, the pressure adjustment section is not limited to the air bag 160, and there may be used a filter through which a gas can pass and which can prevent invasion of bacteria from the outside and emissions of toxic substances to the outside. Furthermore, connection means of the container cap 30, 30A or 30B to the container cap main body 40, 40A or 40B is not limited to fitting connection, and may be screwing, welding, bonding or the like. Additionally, the respective embodiments may be appropriately combined and implemented, and in this case, combined effects can be obtained. Furthermore, the above embodiments include various inventions, and various inventions can be extracted by selected combinations from a plurality of disclosed components. For example, even when several components are eliminated from all components described in the embodiments, problems can be solved and effects can be obtained. In this case, a configuration from which the components are eliminated can be extracted as the invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. Connection equipment comprising:
   an equipment connector comprising a first connecting section that is connectable to equipment through which a fluid moves, a first liquid flow path that communicates with an interior of the equipment when the equipment is connected to the first connecting section, and a first valve that is to open and close the first liquid flow path and that opens when pressed,
   a container connector comprising a second connecting section that is connectable to a container, a second liquid flow path that communicates with an interior of the container when the container is connected to the second connecting section, and a second valve that is to open and close the second liquid flow path and that opens when pressed by the first valve, and
   a lock mechanism that locks the equipment connector and the container connector in a state where the first valve is pressed by the second valve, the first valve and the second valve are opened and the first liquid flow path is in communication with the second liquid flow path, and that unlocks the connectors in a state where the first valve and the second valve are closed;
   wherein:
      the equipment connector includes a pressure adjustment section, and a first gas flow path connected to the pressure adjustment section;
      the first valve is to open and close the first liquid flow path and the first gas flow path;
      the container connector includes a second gas flow path that communicates with the interior of the container when the container is connected to the second connecting section;
      the second valve is to open and close the second liquid flow path and the second gas flow path; and
      the lock mechanism locks the equipment connector and the container connector in a state where the first valve is pressed by the second valve, the first valve and the second valve are opened, the first liquid flow path is in communication with the second liquid flow path, and the first gas flow path is in communication with the second gas flow path, and the lock mechanism unlocks the connectors in a state where the first valve and the second valve are closed;
   wherein:
      the equipment connector includes a fixed body in which the first connecting section is formed;
      a needle fixed to the fixed body, formed with the first liquid flow path therein, and having a first opening on a tip side;
      a first seal made of a resin and supported by the fixed body movably between a position to liquid-tightly seal the first opening of the needle and a position through which the needle extends; and
      a moving body storing the needle and the first seal therein, having a second opening that is air-tightly sealable with the first seal on the tip side of the needle, forming a part of the first gas flow path between the fixed body and the moving body, and supported by the fixed body movably in an axial direction of the needle between a position where the second opening is air-tightly sealed with the first seal and a position where the sealing of the second opening with the first seal is released in a state where the first opening of the needle is sealed with the first seal;
      the first seal and the needle constitute the first valve;
      the container connector comprises a first member formed with the second liquid flow path therein, and having a third opening that communicates with the second liquid flow path at a tip;
      a tubular second member storing the first member therein, forming a part of the second gas flow path between a tip of the first member and the second member, and having a fourth opening at a tip; and
      a second seal made of a resin as the second valve, formed in a bottomed tubular shape having a bottom that seals the fourth opening of the second member, and including the first member fitted therein; and
      the lock mechanism comprises a first engaging section formed in the moving body; and
      a first engaged section formed in the second member, and engaged with the first engaging section in a state where the first seal is pressed by the second seal to move the first seal and the second seal and unseal the second opening and the fourth opening so that the first gas flow path communicates with the second gas flow path, the third opening is liquid-tightly sealed with the bottom, the needle extends through the first seal and the second seal and the first liquid flow path is in communication with the second liquid flow path, to fix the equipment connector and the container connector.

2. The connection equipment according to claim 1, wherein the pressure adjustment section comprises an air bag and an air bag storage section that stores the air bag.

3. The connection equipment according to claim 1, comprising:
 a second engaging section formed in the moving body,
 a second engaged section formed in the fixed body, and engaged with the second engaging section in a state where the moving body is present at a position where the second opening is sealed with the first seal, to regulate the movement of the moving body, and
 an abutment section for the moving body which is formed in the second member, and abuts on the second engaging section in a state where the second seal is in contact closely with the first seal, to move the second engaging section to a position where the second engaging section disengages from the second engaged section.

4. The connection equipment according to claim 3, wherein the moving body comprises a tubular head sleeve, and
 a stopper sleeve fixed to the head sleeve, and comprising a first arm as the second engaging section extending in an axial direction of the fixed body, a second arm as the first engaging section extending in the axial direction of the fixed body, and a coupling section that couples the first arm and the second arm, the first arm, the second arm and the coupling section being annularly arranged, and the first arm and the second arm being tiltable toward an axis of the head sleeve,
 the fixed body is formed in a tubular shape that stores the head sleeve and the stopper sleeve therein, and comprises, in an inner peripheral surface, a locking protrusion as the second engaged section that is abuttable on the first arm in an axial direction of the fixed body, and an unlocking protrusion that abuts on the second arm in a state where the second opening is sealed with the first seal, to tilt the second arm to a position where the second arm disengages from the first engaged section, and
 the abutment section for the moving body is formed in an outer peripheral surface of the second member, and in the outer peripheral surface, a locking recess as the first engaged section in which the second arm is engageable is formed.

5. The connection equipment according to claim 1, wherein the fixed body comprises an abutment section for the fixed body which abuts on the first engaging section in a state where the second opening of the moving body is sealed with the first seal, to move the first engaging section to a position where the first engaging section disengages from the first engaged section.

6. The connection equipment according to claim 5, comprising:
 a second engaging section formed in the moving body,
 a second engaged section formed in the fixed body, and engaged with the second engaging section in a state where the moving body is present at a position where the second opening is sealed with the first seal, to regulate the movement of the moving body, and
 an abutment section for the moving body which is formed in the second member, and abuts on the second engaging section in a state where the second seal is in contact closely with the first seal, to move the second engaging section to a position where the second engaging section disengages from the second engaged section.

7. The connection equipment according to claim 6, wherein the moving body comprises a tubular head sleeve, and
 a stopper sleeve fixed to the head sleeve, and comprising a first arm as the second engaging section extending in an axial direction of the fixed body, a second arm as the first engaging section extending in the axial direction of the fixed body, and a coupling section that couples the first arm and the second arm, the first arm, the second arm and the coupling section being annularly arranged, and the first arm and the second arm being tiltable toward an axis of the head sleeve,
 the fixed body is formed in a tubular shape that stores the head sleeve and the stopper sleeve therein, and comprises, in an inner peripheral surface, a locking protrusion as the second engaged section that is abuttable on the first arm in an axial direction of the fixed body, and an unlocking protrusion that abuts on the second arm in a state where the second opening is sealed with the first seal, to tilt the second arm to a position where the second arm disengages from the first engaged section, and
 the abutment section for the moving body is formed in an outer peripheral surface of the second member, and in the outer peripheral surface, a locking recess as the first engaged section in which the second arm is engageable is formed.

8. An equipment connector comprising:
 a first connecting section that is connectable to equipment through which a fluid moves;
 a first liquid flow path that communicates with an interior of the equipment when the equipment is connected to the first connecting section; a first valve that is to open and close the first liquid flow path and that opens when pressed;
 a lock mechanism that locks a container connector in a state where the first valve is pressed by a second valve of the container connector, the first valve and the second valve are opened and the first liquid flow path is in communication with a second liquid flow path of the container connector, and that unlocks the container connector in a state where the first valve and the second valve are closed;
 a pressure adjustment section;
 a first gas flow path connected to the pressure adjustment section, wherein the first valve is to open and close the first liquid flow path and the first gas flow path; and
 the lock mechanism locks the container connector in a state where the first valve is pressed by the second valve of the container connector, the first valve and the second valve are opened, the first liquid flow path is in communication with the second liquid flow path of the container connector, and the first gas flow path is in communication with a second gas flow path of the container connector, and the lock mechanism unlocks the container connector in the state where the first valve and the second valve are closed;
 wherein:

the equipment connector includes a pressure adjustment section, and a first gas flow path connected to the pressure adjustment section;

the first valve is to open and close the first liquid flow path and the first gas flow path;

the container connector includes a second gas flow path that communicates with the interior of the container when the container is connected to the second connecting section;

the second valve is to open and close the second liquid flow path and the second gas flow path; and the lock mechanism locks the equipment connector and the container connector in a state where the first valve is pressed by the second valve, the first valve and the second valve are opened, the first liquid flow path is in communication with the second liquid flow path, and the first gas flow path is in communication with the second gas flow path, and the lock mechanism unlocks the connectors in a state where the first valve and the second valve are closed;

wherein:

the equipment connector comprises a fixed body in which the first connecting section is formed;

a needle fixed to the fixed body, formed with the first liquid flow path therein, and having a first opening on a tip side;

a first seal made of a resin and supported by the fixed body movably between a position to liquid-tightly seal the first opening of the needle and a position through which the needle extends; and a moving body storing the needle and the first seal therein, having a second opening that is air-tightly sealable with the first seal on the tip side of the needle, forming a part of the first gas flow path between the fixed body and the moving body, and supported by the fixed body movably in an axial direction of the needle between a position where the second opening is air-tightly sealed with the first seal and a position where the sealing of the second opening with the first seal is released in a state where the first opening of the needle is sealed with the first seal;

the first seal and the needle constitute the first valve;

the container connector comprises a first member formed with the second liquid flow path therein, and having a third opening that communicates with the second liquid flow path at a tip;

a tubular second member storing the first member therein, forming a part of the second gas flow path between a tip of the first member and the second member, and having a fourth opening at a tip; and a second seal made of a resin as the second valve, formed in a bottomed tubular shape having a bottom that seals the fourth opening of the second member, and including the first member fitted therein; and the lock mechanism comprises a first engaging section formed in the moving body; and a first engaged section formed in the second member, and engaged with the first engaging section in a state where the first seal is pressed by the second seal to move the first seal and the second seal and unseal the second opening and the fourth opening so that the first gas flow path communicates with the second gas flow path, the third opening is liquid-tightly sealed with the bottom, the needle extends through the first seal and the second seal and the first liquid flow path is in communication with the second liquid flow path, to fix the equipment connector and the container connector.

9. Connection equipment comprising:

an equipment connector comprising a first connecting section that is connectable to equipment through which a fluid moves, a first liquid flow path that communicates with an interior of the equipment when the equipment is connected to the first connecting section, and a first valve that is to open and close the first liquid flow path and that opens when pressed, a container connector comprising a second connecting section that is connectable to a container, a second liquid flow path that communicates with an interior of the container when the container is connected to the second connecting section, and a second valve that is to open and close the second liquid flow path and that opens when pressed by the first valve, and a lock mechanism that locks the equipment connector and the container connector in a state where the first valve is pressed by the second valve, the first valve and the second valve are opened and the first liquid flow path is in communication with the second liquid flow path, and that unlocks the connectors in a state where the first valve and the second valve are closed;

wherein:

the equipment connector comprises a pressure adjustment section, and a first gas flow path connected to the pressure adjustment section;

the first valve is to open and close the first liquid flow path and the first gas flow path;

the container connector comprises a second gas flow path that communicates with the interior of the container when the container is connected to the second connecting section;

the second valve is to open and close the second liquid flow path and the second gas flow path; and the lock mechanism locks the equipment connector and the container connector in a state where the first valve is pressed by the second valve, the first valve and the second valve are opened, the first liquid flow path is in communication with the second liquid flow path, and the first gas flow path is in communication with the second gas flow path, and the lock mechanism unlocks the connectors in a state where the first valve and the second valve are closed:

wherein:

the equipment connector comprises a fixed body in which the first connecting section is formed, a first needle fixed to the fixed body, formed with the first liquid flow path therein, and having an opening on a tip side, a second needle fixed to the fixed body, formed with the first gas flow path therein, and having an opening on a tip side, a first seal, and a moving body supported by the fixed body so that the first seal is movable in a axial direction of the first needle and the second needle between a position to liquid-tightly seal the opening of the first needle and air-tightly seal the opening of the second needle and a position through which the first needle and the second needle extend, the first seal, the first needle and the second needle constitute the first valve, the container connector comprises a first member having the second liquid flow path and the second gas flow path therein,
a second seal provided at an end portion of the first member to seal the second liquid flow path and the second gas flow path, and
a tubular second member that stores the first member and the second seal therein, and
the lock mechanism comprises a first engaging section formed in the moving body, and
a first engaged section formed in the second member, and engaged with the first engaging section in a state where the first seal is pressed by the second seal, to move the moving body so that the first needle extends through the first seal and the second seal and the first needle is disposed in the second liquid flow path, and the second needle extends through the first seal and the second seal and the second needle is disposed in the second gas flow path, to fix the equipment connector and the container connector.

10. The connection equipment according to claim 9, wherein the fixed body comprises an abutment section for the fixed body which abuts on the first engaging section in a state where the opening of the first needle and the opening of the second needle are arranged in the first seal, to move the first engaging section to a position where the first engaging section disengages from the first engaged section.

11. The connection equipment according to claim 9, wherein the pressure adjustment section comprises an air bag and an air bag storage section that stores the air bag.

12. The connection equipment according to claim 9, comprising:
a second engaging section formed in the moving body,
a second engaged section formed in the fixed body, and engaged with the second engaging section in a state where the opening of the first needle and the opening of the second needle are present in the first seal, to regulate the movement of the moving body, and
an abutment section for the moving body which is formed in the second member, and abuts on the second engaging section to move the second engaging section to a position where the second engaging section disengages from the second engaged section.

13. The connection equipment according to claim 12, wherein the moving body comprises a tubular head sleeve, and
a stopper sleeve fixed to the head sleeve, and comprising a first arm as the second engaging section extending in an axial direction of the fixed body, a second arm as the first engaging section extending in the axial direction of the fixed body, and a coupling section that couples the first arm and the second arm, the first arm, the second arm and the coupling section being annularly arranged, and the first arm and the second arm being tiltable toward an axis of the head sleeve,
the fixed body is formed in a tubular shape that stores the head sleeve and the stopper sleeve therein, and comprises, in an inner peripheral surface, a locking protrusion as the second engaged section that is abuttable on the first arm in the axial direction of the fixed body, and an unlocking protrusion that abuts on the second arm, to tilt the second arm to a position where the second arm disengages from the first engaged section, and
the abutment section for the moving body is formed in an outer peripheral surface of the second member, and in the outer peripheral surface, a locking recess as the first engaged section in which the second arm is engageable is formed.

14. An equipment connector comprising:
a first connecting section that is connectable to equipment through which a fluid moves,
a first liquid flow path that communicates with an interior of the equipment when the equipment is connected to the first connecting section,
a first valve that is to open and close the first liquid flow path and that opens when pressed, and
a lock mechanism that locks a container connector in a state where the first valve is pressed by a second valve of the container connector, the first valve and the second valve are opened and the first liquid flow path is in communication with a second liquid flow path of the container connector, and that unlocks the container connector in a state where the first valve and the second valve are closed;
a pressure adjustment section, and
a first gas flow path connected to the pressure adjustment section, wherein the first valve is to open and close the first liquid flow path and the first gas flow path, and
the lock mechanism locks the container connector in a state where the first valve is pressed by the second valve of the container connector, the first valve and the second valve are opened, the first liquid flow path is in communication with the second liquid flow path of the container connector, and the first gas flow path is in communication with a second gas flow path of the container connector, and the lock mechanism unlocks the container connector in the state where the first valve and the second valve are closed;
wherein:
the equipment connector comprises a fixed body in which the first connecting section is formed;
a first needle fixed to the fixed body, formed with the first liquid flow path therein, and having an opening on a tip side;
a second needle fixed to the fixed body, formed with the first gas flow path therein, and having an opening on a tip side;
a first seal; and
a moving body supported by the fixed body so that the first seal is movable in a axial direction of the first needle and the second needle between a position to liquid-tightly seal the opening of the first needle and air-tightly seal the opening of the second needle and a position through which the first needle and the second needle extend;
the first seal, the first needle and the second needle constitute the first valve;
the container connector comprises a first member having the second liquid flow path and the second gas flow path therein;
a second seal provided at an end portion of the first member to seal the second liquid flow path and the second gas flow path; and
a tubular second member that stores the first member and the second seal therein; and
the lock mechanism comprises a first engaging section formed in the moving body; and
a first engaged section formed in the second member, and engaged with the first engaging section in a state where the first seal is pressed by the second seal, to move the moving body so that the first needle extends through the first seal and the second seal and the first needle is disposed in the second liquid flow path, and the second needle extends through the first seal and the second seal and the second needle is disposed in the second gas flow path, to fix the equipment connector and the container connector.

* * * * *